(12) United States Patent
Dezawa et al.

(10) Patent No.: US 8,092,792 B2
(45) Date of Patent: *Jan. 10, 2012

(54) USE OF MATERIALS FOR TREATMENT OF CENTRAL NERVOUS SYSTEM LESIONS

(75) Inventors: Mari Dezawa, Kyoto (JP); Keita Mori, Cupertino, CA (US)

(73) Assignee: Sanbio, Inc., Mountain View, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/462,143

(22) Filed: Jul. 30, 2009

(65) Prior Publication Data

US 2010/0034790 A1 Feb. 11, 2010

Related U.S. Application Data

(63) Continuation of application No. 11/368,919, filed on Mar. 6, 2006, now abandoned, and a continuation-in-part of application No. 10/503,816, filed on May 24, 2005, now Pat. No. 7,682,825.

(60) Provisional application No. 60/659,335, filed on Mar. 7, 2005.

(51) Int. Cl.
*A61K 35/12* (2006.01)

(52) U.S. Cl. .................................................. 424/93.21

(58) Field of Classification Search ........................ None
See application file for complete search history.

(56) References Cited

U.S. PATENT DOCUMENTS

| | | | |
|---|---|---|---|
| 5,226,914 | A | 7/1993 | Caplan et al. |
| 5,780,300 | A | 7/1998 | Artavanis-Tsakonas et al. |
| 5,854,004 | A | 12/1998 | Czernilofsky et al. |
| 6,528,245 | B2 | 3/2003 | Sanchez-Ramos et al. |
| 6,555,374 | B1 | 4/2003 | Gimble et al. |
| 6,787,355 | B1 | 9/2004 | Miller et al. |
| 7,129,034 | B2 | 10/2006 | Yu et al. |
| 2002/0146821 | A1 | 10/2002 | Sanchez-Ramos et al. |
| 2003/0003090 | A1 | 1/2003 | Prockop et al. |
| 2003/0049837 | A1 | 3/2003 | Weiss et al. |
| 2003/0203484 | A1 | 10/2003 | Black et al. |
| 2004/0235165 | A1 | 11/2004 | Prockop et al. |
| 2006/0166362 | A1 | 7/2006 | Dezawa et al. |
| 2006/0251624 | A1 | 11/2006 | Dezawa |

FOREIGN PATENT DOCUMENTS

| | | |
|---|---|---|
| EP | 1479767 A1 | 11/2004 |
| WO | 99/56759 | 11/1999 |
| WO | WO 01/22978 | 4/2001 |
| WO | WO 03/066856 | 8/2003 |
| WO | WO03066856 * | 8/2003 |
| WO | WO 2005/100552 | 10/2005 |
| WO | WO 2006/055685 | 5/2006 |

OTHER PUBLICATIONS

Rempe et al. (Neurology. Aug 2002; 59(4): 486-487).*
Life Science Dictionary, citation for "stem cells".
Lindvall, et al., "Stem Cell Therapy for Human Neurodegenerative Disorders—How to Make it Work," *Nature Med* 10 Suppl S42-S50 (2004).
Longa, et al., "Reversible Middle Cerebral Artery Occlusion Without Craniectomy in Rats," *Stroke* 20:84-91 (1989).
Lu, et al., "Induction of Bone Marrow Stromal Cells to Neurons: Differentiation, Transdifferentiation, or Artifact?" *Journal of Neuroscience Research* 77:174-191 (2004).
Mahmood, et al., "Intracerebral Transplantation of Marrow Stromal Cells Cultured with Neurotrophic Factors Promotes Functional Recovery in Adult Rats Subjected to Traumatic Brain Injury," *J Neurotrauma* 12(12):1609-1617 (2002).
Mattson, "Stem Cells as Therapeutics for Neurodegenerative Dosrorder?" *Expert Rev. Neurotherapeutics* 1:267-273 (2001).
Mezey, et al., "Turning Blood into Brain:Cells Bearing Neuronal Antigens Generated in Vivo from Bone Marrow," *Science* 290:1779-1782 (2000).
Pereira, et al., "Cultured Adherent Cells from Marrow can Serve as Long-Lasting Precursor Cells for Bone, Cartilage, and Lung in Irradiated Mice," *PNAS USA* 22:4857-4861 (1995).
Pittenger, et al., "Multilineage Potential of Adult Human Mesenchymal Stem Cells," *Science* 284:143-147 (1999).
Prockop, "Marrow Stromal Cells as Stem Cells for Nonhematopoietic Tissues," *Science* 276:71-74 (1997).
Rempe, et al., "Using Bone Marrow Stromal Cells for Treatment of Stroke," *Neurology* 59(4):486-487 (2002).
Rickman, et at., "BDNF and CNTF Enhance the Neuronal Differentiation of Bone Marrow Stromal Cells," *Soc. Neurosci.Abstracts* 21:58 (2001).
Schroeder, et al., "Notch Signalling Via Rbp-J Promotes Myeloid Differentiation," *EMBO J* 19:2558-2568 (2000).
Stedman's Medical Dictionary 27$^{th}$ Edition, citation for :neural.
Vogel, et al., "Heterogeneity Among Human Bone Marrow-Derived Mesenchymal Stern Cells and Neural Progenitor Cells," *Hematopoietic Stem Cells* 88:126-133 (2003).
Wang, et al., "Glial Cell Line-Derived Neurotrophic Factor Protects Against Ischemia-Induced Injury in the Cerebral Cortex," *J Neurosci* 17:4341-4348 (1997).
Websters Third New International Dictionary, Unabridged (2002): Definition of "Facilitate" (p. 812).
Weissman, "Translating Stem and Progenitor Cell Biology to the Clinic: Barriers and Opportunities," *Science* 287:1442-1446 (2000).

(Continued)

*Primary Examiner* — Scott Long
(74) *Attorney, Agent, or Firm* — Dahna S. Pasternak; Sean M. Brennan

(57) ABSTRACT

Disclosed are methods and materials for treatment of central nervous system lesions. Preferred methods and materials comprise neuronal precursor cells and/or marrow adherent stem cell-derived neuronal cells.

19 Claims, 27 Drawing Sheets

OTHER PUBLICATIONS

Woodbury, et al.," Adult Rat and Human Bone Marrow Stromal Cells Differentiate Into Neurons," *Journal of Neuroscience Research* 61:364-370 (2000).

Zhao, et al., "Human Bone Marrow Stem Cells Exhibit Neural Phenotypes and Ameliorate Neurological Defecits After Grafting into the Ischemic Brain of Rats," *Exp Neurol* 184:11-20 (2002).

Altumbabic, et al., "Intracerebral Hemorrhage in the Rat," *Stroke* 29:1917-1922 (1998).

Barker, et al., "Neural Transplantation Therapies for Parkinson's and Huntington's Diseases," *Drug Discov Today* 6:575-582 (2001).

Bederson, et al., "Rat Middle Cerebral Artery Occlusion: Evaluation of the Model and Development of a Neurologic Examination," *Stroke* 17:472-476 (1986).

Borlongan, et al., "Locomotor and Passive Avoidance Deficits Following Occlusion of the Middle Cerebral Artery," *Physiol Behav* 58:909-917 (1995).

Borlongan, et al. "Transplantation of Cryopreserved Human Embryonal Carcinoma-Derived Neurons (NT2N Cells) Promotes Functional Recovery in Ischemic Ratsw,"*Exp Neurol* 149:310-321 (1998).

Borlongan, et al., "Early Assessment of Motor Dysfunctional Aids in Successful Occlusion of the Middle Cerebral Artery," *Neuroreport* 9:3615-3621 (1998).

Borlongan, et al., "Chronic Cyclosporine-A Injection in Rats with Damaged Blood—Brain Barrier Does Not Impair Retention of Passive Avoidance,"*Neurosci Res* 32:195-200 (1998).

Borlongan, et al., "Glial Cell Survival is Enhanced During Melatonin-Induced Neuroprotection Against Cerebral Ischemia," *FASEB J* 14:1307-1317 (2000).

Brazelton, et al., "From Marrow to Brain: Expression of Neuronal Phenotypes in Adult Mice," *Science* 290:1775-1779 (2000).

Conget, et al., "Phenotypical and Functional Properties of Human Bone Marrow Mesenchymal Progenitor Cells," *Journal of Cellular Physiology* 181:67-73 (1999).

Dahlstrand, et al., "Nestin Mma Expression Correlates With the Central Nervous System Progenitor Cell State in Many, but Not All, Regions of Developing Central Nervous System," *Developmental Brain Research* 84:109-129 (1995).

Database WPI Week, "Nervous System Progenitor Cells," Derwent Publications Ltd., London, GB; AN: 2004-344670 (2004).

Deng, et al., "In Vitro Differentiation of Human Marrow Stromal Cells Into Early Progenitors of Neural Cells by Conditions That Increase Intracellular Cyclic Amp," *Biochem Biophys Res Commun* 282:148-152 (2001).

De Ryck, et al., "Photochemical Stroke Model: Flunarizine Prevents Sensorimotor Deficits After Neocartal Infarcts in Rats," *Stroke* 20:1383-1390 (1989).

DeZawa, et al, "Specific Induction of Neuronal Cells from Bone Marrow Stromal Cells and Application for Autologous Transplantation," *J Clin Invest* 113(12):1701-1710 (2004).

Dixon et al., "A Fluid Percussion Model of Experimental Brain Injury in the Rat,"*J Neurosurg* 67:110-119 (1987).

Fukunaga, et al., "Differentiation and Angiogenesis of Central Nervous System Stern Cells Implanted With Mesenchyme into Ischemic Rat Brain," *Cell Transplant* 8:435-441 (1999).

Hofstetter, et al., "Marrow Stromal Cells From Guiding Strands in the Injured Spinal Cord and Promote Recovery," *PNAS* 22199-2204 (2002).

Isacson, "The Production and Use of Cells as Therapeutic Agents in Neurodegenerative Diseases," *Lancet Neurol*. 2:417-424 (2003).

Jin, et al., "Comparison of Ischemia-Directed Migration of Neural Precursor Cells After Intrastriatal, Intraventricular, or Intravenous Transplantation in the Rat," *Neurobiol Dis* 18:366-374 (2005).

Joshi, et al., "Neuronal Stem Cells," *Neurology India* 51(3):323-328 (2003).

Kennea, et al., "Perinatal Applications of Neural Stem Cells," *Best Practice & Research Clinical Obstetrics and Gynaecology* 18(6):977-994 (2004).

Koizumi, et al., "Experimental Studies of Ischemic Brain Edema 1. A New Experimental Model of Cerebral Embolism in Rats in Which Recirculation can be Introduced in the Ischemic Area," *Jpn J Stroke* 8:1-8 (1986) English Abstract.

Li, et al., "Human Marrow Stromal Cell Therapy for Stroke in Rat: Neurotrophins and Functional Recovery," *Neurology* 2:514-523 (2002).

Cotran, et al., "Robbins Pathologic Basis of Disease," Sixth Edition, Chapter 30, pp. 1306-1307 (1999).

Braunwald, et al., "Harrisons Principals of Internal Medicine," 15th Edition, pp. 2369-2370 (2001).

WebMD entry on Brain Lesions (2011).

\* cited by examiner

USE OF MATERIALS FOR TREATMENT OF CENTRAL NERVOUS SYSTEM LESIONS

CROSS-REFERENCE TO RELATED APPLICATIONS

This application is a continuation of U.S. patent application Ser. No. 11/368,919, filed Mar. 6, 2006, now abandoned which claims priority to U.S. Provisional Patent Application No. 60/659,335, filed Mar. 7, 2005. This application is also a Continuation-in-Part of U.S. patent application Ser. No. 10/503,816, filed May 24, 2005 now U.S. Pat. No. 7,682,825. All of the above-referenced applications are incorporated herein in their entireties.

FIELD OF THE INVENTION

The invention relates to treatment of central nervous system lesions, particularly to treatment of stroke.

BACKGROUND OF THE INVENTION

Lesions can form in central nervous system ("CNS") tissue for a number of reasons. One of the leading causes of CNS lesions is stroke. Stroke is characterized by the sudden loss of circulation to an area of the brain, resulting in a corresponding loss of neurologic function. Also called cerebrovascular accident or stroke syndrome, stroke is a nonspecific term encompassing a heterogeneous group of pathophysiologic causes, including thrombosis, embolism, and hemorrhage. Recent reports indicate an incidence exceeding 500,000 new strokes of all types per year. Stroke is a leading killer and disabler. Combining all types of stroke, it is the third leading cause of death and the first leading cause of disability. At current trends, this number is projected to jump to one million per year by the year 2050. When the direct costs (care and treatment) and the indirect costs (lost productivity) of strokes are considered together, strokes cost US society $43.3 billion per year. Strokes currently are classified as either hemorrhagic or ischemic. Acute ischemic stroke refers to strokes caused by thrombosis or embolism and accounts for 80% of all strokes.

The four major neuroanatomic ischemic stroke syndromes are caused by disruption of their respective cerebrovascular distributions.

Anterior cerebral artery occlusions primarily affect frontal lobe function, producing altered mental status, impaired judgment, contralateral lower extremity weakness and hypesthesia, and gait apraxia.

Middle cerebral artery (MCA) occlusions commonly produce contralateral hemiparesis, contralateral hypesthesia, ipsilateral hemianopsia (blindness in one half of the visual field), and gaze preference toward the side of the lesion. Agnosia is common, and receptive or expressive aphasia may result if the lesion occurs in the dominant hemisphere. Since the MCA supplies the upper extremity motor strip, weakness of the arm and face is usually worse than that of the lower limb.

Posterior cerebral artery occlusions affect vision and thought, producing homonymous hemianopsia, cortical blindness, visual agnosia, altered mental status, and impaired memory.

Vertebrobasilar artery occlusions are notoriously difficult to detect because they cause a wide variety of cranial nerve, cerebellar, and brainstem deficits. These include vertigo, nystagmus, diplopia, visual field deficits, dysphagia, dysarthria, facial hypesthesia, syncope, and ataxia. Loss of pain and temperature sensation occurs on the ipsilateral face and contralateral body. In contrast, anterior strokes produce findings on one side of the body only.

These occlusions may occur for a variety of reasons. Emboli may arise from the heart, the extracranial arteries or, rarely, the right-sided circulation (paradoxical emboli). The sources of cardiogenic emboli include valvular thrombi (e.g., in mitral stenosis, endocarditis, prosthetic valves); mural thrombi (e.g., in myocardial infarction [MI], atrial fibrillation, dilated cardiomyopathy); and atrial myxomas. MI is associated with a 2-3% incidence of embolic stroke, of which 85% occur in the first month after MI.

Lacunar infarcts account for 13-20% of all cerebral infarctions and usually involve the small terminal vasculature of the subcortical cerebrum and brainstem. Lacunar infarcts commonly occur in patients with small vessel disease, such as diabetes and hypertension. Small emboli or an in situ process called lipohyalinosis is thought to cause lacunar infarcts. The most common lacunar syndromes include pure motor, pure sensory, and ataxic hemiparetic strokes. By virtue of their small size and well-defined subcortical location, lacunar infarcts do not lead to impairments in cognition, memory, speech, or level of consciousness.

The most common sites of thrombotic occlusion are cerebral artery branch points, especially in the distribution of the internal carotid artery. Arterial stenosis (i.e., turbulent blood flow), atherosclerosis (i.e., ulcerated plaques), and platelet adherence cause the formation of blood clots that either embolize or occlude the artery. Less common causes of thrombosis include polycythemia, sickle cell anemia, protein C deficiency, fibromuscular dysplasia of the cerebral arteries, and prolonged vasoconstriction from migraine headache disorders. Any process that causes dissection of the cerebral arteries also can cause thrombotic stroke (e.g., trauma, thoracic aortic dissection, arteritis). Occasionally, hypoperfusion distal to a stenotic or occluded artery or hypoperfusion of a vulnerable watershed region between two cerebral arterial territories can cause ischemic stroke.

Turning to hemorrhagic stroke, the terms intracerebral hemorrhage (ICH) and hemorrhagic stroke are used interchangeably in this discussion and are regarded as a separate entity from hemorrhagic transformation of ischemic stroke. ICH accounts for approximately 20% of all strokes and is associated with higher mortality rates than cerebral infarctions. Patients with hemorrhagic stroke present with similar focal neurologic deficits but tend to be more ill than patients with ischemic stroke. Patients with intracerebral bleeds are more likely to have headache, altered mental status, seizures, nausea and vomiting, and/or marked hypertension; however, none of these findings distinguish reliably between hemorrhagic and ischemic strokes.

In ICH, bleeding occurs directly into the brain parenchyma. The usual mechanism is thought to be leakage from small intracerebral arteries damaged by chronic hypertension. Other mechanisms include bleeding diatheses, iatrogenic anticoagulation, cerebral amyloidosis, and cocaine abuse. ICH tends to be found in certain sites in the brain, including the thalamus, putamen, cerebellum, and brain stem. In addition to the area of the brain injured by the hemorrhage, the surrounding brain can be damaged by pressure produced by the mass effect of the hematoma. A general increase in intracranial pressure may occur. The 30-day mortality rate for hemorrhagic stroke is 40-80%. Approximately 50% of all deaths occur within the first 48 hours.

Other causes for CNS lesions are conventionally known, including trauma and various diseases of the CNS.

Treating CNS lesions implicates neurogenesis, i.e. the (re) generation of neurons in a region of a patient's tissue that is of interest, including but not limited to replacement of damaged neurons in a central nervous system lesion. Unfortunately, neuronal (CNS) tissue is well-known for its limited reparative/regenerative capacity. The generation of new neurons in the adult is largely restricted to two regions, the SVZ lining the lateral ventricles, and the subgranular zone of the dentate gyrus. Limited neuronal replacement has been demonstrated resulting from endogenous precursor stem cells that had migrated from the SVZ.

Some initial success has been reported with certain neurogenesis methods but these methods have not been clinically successful. Accordingly, what is needed are methods and compositions that overcome problems noted in the art for treatment of central nervous system lesions.

SUMMARY OF THE INVENTION

In an aspect, the invention relates to a method comprising: providing neuronal precursor cells; and administering the neuronal precursor cells to a patient suffering from a central nervous system lesion in an amount sufficient to facilitate functional recovery of the patient.

In another aspect, the invention relates to a graft forming unit comprising: neuronal precursor cells present in an amount sufficient to facilitate functional recovery of a patient suffering from a central nervous system lesion following administration of the neuronal precursor cells to the patient; and a pharmaceutically acceptable carrier.

In still another aspect, the invention relates to a method comprising: providing marrow-adherent stem cell-derived neuronal cells; and administering the marrow-adherent stem cell-derived neuronal cells to a patient suffering from a central nervous system lesion in an amount sufficient to facilitate functional recovery of the patient.

In yet another aspect, the invention relates to a graft forming unit comprising: marrow-adherent stem cell-derived neuronal cells present in an amount sufficient to facilitate functional recovery of a patient suffering from a central nervous system lesion following administration of the marrow-adherent stem cell-derived neuronal cells to the patient; and a pharmaceutically acceptable carrier.

DETAILED DESCRIPTION OF THE INVENTION

A. Introduction

Figure 1:
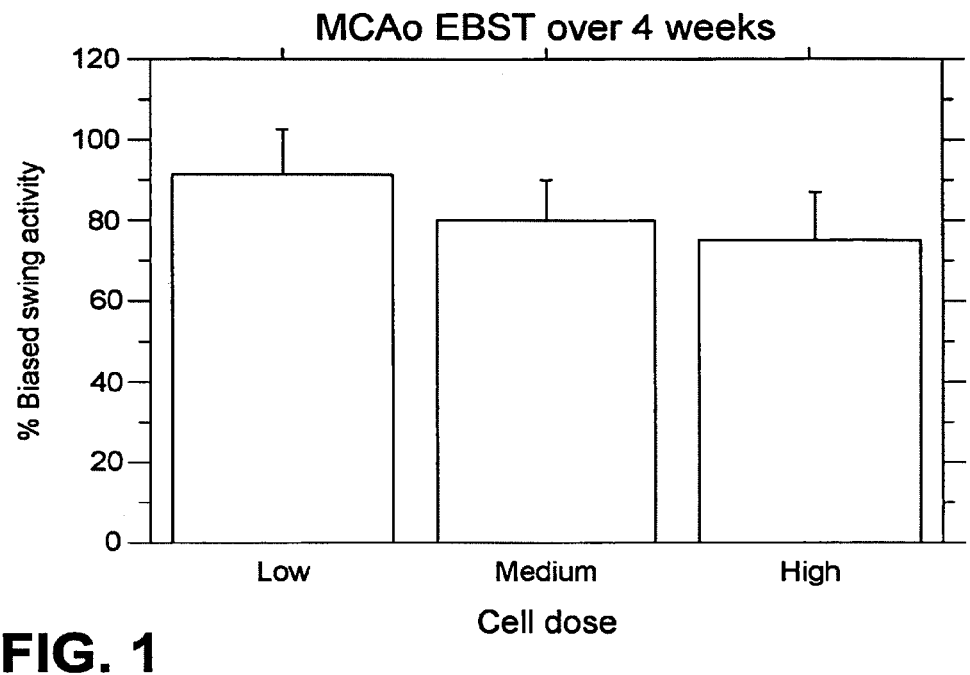
FIG. 1 shows results from the MCAo procedure.

The inventors have unexpectedly and surprisingly discovered that the problems and limitations noted above can be overcome by practicing the invention disclosed herein. In particular, the inventors have unexpectedly discovered that it is possible to provide NPCs and/or MNCs and administer those NPCs and/or MNCs to a patient suffering from a central nervous system lesion in an amount sufficient to facilitate functional recovery of the patient.

The approach disclosed herein has several advantages over the prior art. First, it provides for a dose-response relationship that can allow a physician to tailor the surgical procedure to repair the central nervous system lesion on a patient by patient basis. Second, it provides for an allogeneic approach to engraftment. This is useful for characterizing the NPCs and/or MNCs and/or graft forming units and providing GFU to GFU (or NPC to NPC, or MNC to MNC) consistency, both in terms of the cell batches and transplantation procedure. Further, use of NPCs allows for more precise reconstruction of the central nervous system, as compared to use of other multipotent cells. This is because a significant majority of neuronal precursor cells, more than other types of multi-potent cells, will adopt a cell fate of neuronal cells when differentiating, rather than differentiating into other cell types. This can be important when trying to provide control over transplantation outcome and limits the possibilities of undesirable (or undifferentiated) growth of transplanted cells. Additionally, use of MNCs is desirable because the cells are more differentiated multi-potent cells which may provide for improved functional recovery.

The present invention will now be described in more detail.

Definitions

All publications cited in this specification are hereby incorporated by reference for all purposes and in their entirety as if each individual publication were specifically and individually indicated to be incorporated by reference.

"Administering" means providing NPCs and/or inventive grafts to a patient.

"Area" means a region or defined volume. For instance, an area of the central nervous system would be a region or defined volume located in the central nervous system.

"Central nervous system ischemic event" or "CNS ischemic event" means any occurrence that results in a lack or physiologically significant reduction of blood flow to an area of the central nervous system of a patient. In a preferred embodiment, a CNS ischemic event comprises an ischemic stroke.

"Central nervous system lesion" or "CNS lesion" means an area of damaged, malfunctioning, or diseased neuronal central nervous system tissue, or a penumbra surrounding such damaged, malfunctioning, or diseased neuronal central nervous system tissue, damaged by a CNS ischemic event or by a hemorrhage (e.g., in a preferred embodiment, hemorrhagic stroke).

"Central nervous system tissue" means a tissue conventionally associated with the central nervous system. Brain tissue and spinal cord tissue are non-limiting examples of central nervous system tissue. Certain embodiments of the present invention concern central nervous system tissue, wherein the central nervous system tissue has been damaged by an ischemic event. Such damage may occur as conventionally understood, through oxygen deprivation, and other associated cascades and by-products of such deprivation and associated cascades.

"Functional recovery" means the recovery of CNS function with respect to a CNS lesion as determined either by measurement of neurobiological parameters characteristic of that function (i.e. CBF, EEG, cortical expansion, etc.), or by measurement of behavioral function (e.g. rearing or auditory startle in murine models, or other models disclosed herein or known in the art). Recovery is determined by the tendency of the measured variable to approximate the values observed in a normal or control population. Functional recovery can be complete, i.e. the recovery returns the value of the measured parameter to the value observed in the normal or control population, as determined by appropriate statistical methodology. Functional recovery can also be incomplete or partial. For instance, a patient can experience complete functional recovery of a measured parameter, or 75% recovery, or 50% recovery, etc.

"Functionally recovered area of the central nervous system" means to CNS tissue formerly involved in a lesion and subsequently functionally recovered through the practice of the present invention.

"Graft Forming Unit" or "GFU" means a composition that (1) comprises NPCs and/or MNCs together with a pharmaceutically acceptable carrier, (2) that is intended for administration to a patient. In a preferred embodiment, mixtures of NPCs and MNCs are expressed contemplated. In other preferred embodiments NPCs are present substantially without MNCs. In still other preferred embodiments MNCs are present substantially without NPCs.

"Marrow adherent stem cells" means a type of mitotic multi-potent cell that gives rise to a variety of cell types: bone cells (osteocytes), cartilage cells (chondrocytes), fat cells (adipocytes), and other kinds of connective tissue cells such as those in tendons.

"MASC-derived Neuronal Cells (MNCs)" means post-mitotic neurons that (1) are derived from marrow adherent stem cells, and (2) that express neuron markers immunohistochemically and exhibit neuron properties in electrophysiological analysis. Suitable methods of generating MNCs in vitro may be found in PCT/JP03/01260. MNCs produced using other techniques known in the art may also be used in the practice of this invention, so long as they meet the definition of MNCs set forth herein. In an embodiment, human MNCs are MAP-2+, neurofilament-M+, and beta tubulin III+ (i.e. TuJ-1+). These markers may be used to isolate MNCs using FACS following production of MNCs using the techniques disclosed in PCT/JP03/01260. Suitable methods of handling MNCs are known conventionally, including those methods disclosed, for example, in U.S. Pat. No. 6,833,269 to Carpenter.

"MCAo" means middle cerebral artery occlusion.

"MCAl" means middle cerebral artery ligation.

"Neurogenesis" means the (re)generation of neurons and neuronal tissue in a region of a patient's tissue that is of interest, including but not limited to replacement of damaged neurons in a central nervous system lesion.

"Neuronal Precursor Cells (NPCs)" means cells that are mitotic, express nestin and other cell markers specific for neural precursor/neural progenitor cells, and are derived from MASCs. NPCs can differentiate into neurons, glia, and oligodendrocytes, and precursors of any of the foregoing. In an embodiment, NPCs can be produced from marrow-adherent stem cells (MASCs) according to methods disclosed in PCT/JP03/01260. NPCs produced using other techniques known in the art may also be used in the practice of this invention, so long as they meet the definition of NPCs set forth herein. Preferably, NPCs comprise human NPCs, although NPCs of other mammalian species are also encompassed within the scope of this invention. In an embodiment, NPCs, preferably human NPCs are CD29+, CD90+, CD105+, CD31−, CD34− and CD45−. These markers may be used to isolate NPCs, preferably human NPCs, using FACS following production of NPCs using the techniques disclosed in PCT/JP03/01260. Suitable methods of handling NPCs are known conventionally, including those methods disclosed, for example, in published United States patent application 20020012903 to Goldman et al.

"Neuron(s)" means any of the impulse-conducting cells that constitute the brain, spinal column, and nerves, consisting of a nucleated cell body with one or more dendrites and a single axon. Biochemically, neurons are characterized by reaction with antibodies for Map, neurofilament-M, and beta-tubulin III (i.e. TuJ-1). Neural cells are also characterized by the presence of neurotransmitter synthetases or neurotransmitter-related proteins and by the secretion of neurotransmitters, for example neuropeptide Y and substance P.

"Neuronal" means neurons, glia, and oligodendrocytes, and precursors of any of the foregoing.

"Patient" means an animal, typically a mammal, and more typically, a human, in need of treatment for a disease or disorder.

"Pharmaceutically acceptable carrier" means any and all solvents, dispersion media, coatings, antibacterial agents, antifungal agents, cryoprotectants isotonic and absorption delaying agents, and the like, that are compatible with pharmaceutical administration of NPCs or of MNCs. The use of such media and agents is well known in the art. Except insofar as any conventional media or agent is incompatible with NPCs or with MNCs, use thereof in the inventive GFUs is contemplated.

"Systemically" means throughout, or throughout substantial portions of, the patient.

"Tissue" means a part of an organism consisting of an aggregate of cells having a similar structure and function. A preferred tissue, according to the invention, is nerve tissue.

"TGI" means transient global ischemia.

"Transplantation", which is used synonymously with "engraftment," means the placement of non-endogenous cells in an area of a patient. Transplantation may be allogeneic, or non-self cells being transplanted. Transplantation may also be autologous, or self cells being transplanted, e.g. from one tissue to another in the same patient.

"Transdifferentiated" means development of a cell along a lineage different from that classically associated with that cell type.

B. NPCs, and Pharmaceutical Compositions Thereof

In an embodiment, NPCs are used in the practice of this invention as part of GFUs that are transplanted into patients. The intent is that the NPCs grow and differentiate into neuronal cells that play a role in the functional recovery of a central nervous system lesion in the patient. For example, NPCs could differentiate into neurons that replace damaged endogenous neurons. Alternatively, NPCs could differentiate into glial cells or neurons that secrete growth factors. These growth factors may have a trophic activity on damaged neurons and aid their functional recovery. In that manner, treatment of central nervous system lesions is possible.

Preferred NPCs and preferred methods of providing such NPCs are disclosed in PCT/JP03/01260, to Dezawa et al., entitled Method of Differentiating/Inducing Bone Marrow Interstitial Cells Into Nerve Cells and Skeleton Muscle Cells by Transferring Notch Gene ("Dezawa"). In particular, the "neural precursor cells" of Dezawa, as described throughout Dezawa and in particular in Example 7, may be used as the NPCs of the present invention. Dezawa discloses that MASCs may be transdifferentiated into neural precursor cells that are then useful as the NPCs of the present invention.

In embodiments, GFUs may be useful in the practice of this invention. Pharmaceutically acceptable carriers useful in GFUs of the present invention can include: sterile isotonic buffers, FRS, isolyte, sterile diluents such as water, normal saline, fixed oils, polyethylene glycols, glycerine, propylene glycol, or other synthetic solvents; antibacterial or antifungal agents such as ascorbic acid, thimerosal, trimethoprim-sulfamethoxazole, nalidixic acid, methenamine hippurate or nitrofurantoin macrocrystals and the like; antioxidants such as ascorbic acid or sodium bisulfite; chelating agents such as EDTA; buffers such as acetates, citrates, or phosphates; and agents for the adjustment of tonicity such as sodium chloride or dextrose. pH can be adjusted with acids or bases, such as hydrochloric acid or sodium hydroxide.

In an embodiment, graft forming units suitable for use in the present invention comprise sterile compositions that comprise the NPCs. For intravenous administration, suitable pharmaceutically acceptable carriers may include physiological saline, normasol, isolyte, plasma-lyte, or phosphate buffered saline (PBS). In all cases, the GFU must be sterile (other than any NPCs or MNCs that are present) and should be fluid to the extent that easy syringability exists (proper fluidity can be maintained, for example, by using materials such as lecithin, by maintaining a certain particle size in the case of dispersion, and by including surfactants). The GFU must be stable under the conditions of manufacture and storage and must be preserved against the contaminating action of microorganisms such as bacteria and fungi, as described above. In certain cases, it will be preferable to include, for example, sugars, polyalcohols such as mannitol or sorbitol, sodium chloride, LiCl, Na butyrate, and sodium orthovanadate in the GFU. Generally, the inventive GFUs may be prepared by incorporating the NPCs into a sterile vehicle which contains a basic dispersion medium and optionally other ingredients from those enumerated above.

It is especially advantageous to formulate the GFUs of the invention in graft forming unit dosage forms for ease of administration and uniformity of dosage. Graft forming unit dosage form as used herein refers to physically discrete units suited as unitary dosages for the subject to be treated. In an embodiment each GFU dosage form contains a predetermined quantity of NPCs calculated to produce the desired therapeutic effect in association with the required pharmaceutical carrier. The specification for the graft forming unit dosage forms of the invention are dictated by and directly dependent on the unique characteristics of the NPCs, the particular therapeutic effect to be achieved, and the limitations inherent in the art of compounding NPCs for the treatment of individuals. The number of NPCs in each graft unit dosage form preferably can vary from about 1000 cells to about 1 billion cells, preferably from about 10,000 cells to about 100 million cells, more preferably from about 50,000 cells to about 50 million cells. The concentration of NPCs in each graft unit dosage form preferably can vary from about 100 cells/$\mu$L to about 100,000 cells/$\mu$L, and more preferably from about 1,000 cells/$\mu$L to about 50,000 cells/$\mu$L.

The GFUs can be included in a container, pack, or dispenser together with instructions for administration. The grafts are preferably stored at approximately 37° C.

In certain embodiments it may be desirable to label the NPCs prior to transplantation. This may be desirable in preclinical (i.e. non-human) models in order to track the migration of transplanted NPCs, differentiation of transplanted NPCs, survival of transplanted NPCs, and so on. Various cell labeling methods may be employed depending on the preclinical circumstances under which the labels are to be read. For instance, fluorescent proteins (green fluorescent protein, red fluorescent protein, etc.) may be used as in circumstances in which a detector can be suitably placed near the transplant site.

When analyzing engrafted brains in non-clinical situations, immunohistochemical analysis may be useful. In an embodiment, brain sections may be doubly-immunostained for green fluorescent protein (GFP) or other cell labels, $\beta$-tubulin III, NeuN (a neuron-specific protein), glial fibrillary acidic protein (GFAP), or O4 (an oligodendrocyte-specific protein) to identify neuronal, astrocytic, glial, or oligodendrocytic profiles. The number of positive profiles for a given antibody and the number of cells expressing GFP may be estimated according to the Abercrombie correction formula. The volume of distribution and total GFP (or other label) positive profiles may be calculated by determining the area of the brain containing at least 10% GFP-positive (or other label-positive) profiles in every fifth section and multiplying by the distance from the anterior aspects of the brain that contain GFP-positive (or other label-positive) profiles.

In an embodiment, when labeling NPCs using GFP, the following materials may be useful:

Materials: Cryo-preserved NPCs, PBS (Invitrogen 14190-136), HTS-FRS (BioLife Solutions 99-609-DV), GFP-Lentivirus stock suspension with a titer of approximately $10^7$/ml, Hexamidine Bromide (polybrene) (Sigma (H-9268)-1 or 2 frozen aliquots @ 10 mg/ml), Sterile Water, USP, Opti-MEM (Invitrogen), and Fetal Bovine Serum (Hyclone).

A GFP-Lentivirus stock suspension may be obtained commercially, or made using a commercially available kits such as the ViraPower Lentiviral Expression System (available from Invitrogen, Carlsbad Calif.). In particular, the pLenti6/V5 Gateway Vector may be combined with a GFP cassette, according to the manufacturer's directions, to eventually produce suitable GFP-lentivirus suspensions.

In an embodiment, labeling may be performed according to the transfection protocols available from the manufacturer, such as the Invitrogen system referred to above.

In another embodiment, when labeling NPCs using GFP, the following methods may be useful: Cell handling procedures, except the centrifugations steps, preferably are performed in a Biohazard Safety Cabinet Level-2. A polybrene stock solution may be prepared by dissolving 10 mg of polybrene in 1 ml of Sterile Water, USP, and filtering through a 0.25 micron filter. The resultant, filtered stock solution can be divided into aliquots and stored protected from light at $-20°$ C.

The day before viral infection, plate NPCs in a T225 flask containing 30 ml of the cell culture medium at a density of 2 million cells per flask; and culture cells in a 37° C./5% $CO_2$ incubator overnight On the day of viral infection, thaw the lentivirus stock at RT and the polybrene stock solution in a 37 Deg C. water bath. In a 50 ml falcon tube, add 45 ml of pre-warmed (37° C.) 10% FBS in alpha MEM and 5 ml of the thawed viral stock to obtain a medium with a MOI around 10. Add the thawed polybrene at a final concentration of 10 ug/ml (1,000× dilution). Remove the old medium from the T225 flask, and add the viral mixture into the flask and rock gently back and forth 34 times. Return the flask into the 37° C./5% $CO_2$ incubator.

On the following day, remove completely the viral medium from the flask. Wash 6×30 ml with 10% FBS in alpha MEM. Collect 5 ml from each wash for infectivity testing. Replace with fresh culture medium, and put the flask back into the incubator.

Next day, harvest viral infected cells, count and re-suspend them to a total volume of 360 ul in HTS-FRS and transferred to a 1.5 ml sterile, DNAse-free, RNAse-free, pyrogen-free microfuge tube. The infected cell concentration may be set to match an appropriate transplantation volume. The cells may then be held on wet ice until use for graft administration.

MNCs, and Pharmaceutical Compositions Thereof

In an embodiment, MNCs are used in the practice of this invention as part of grafts that are transplanted into patients. The intent is that the MNCs play a role in the functional recovery of a region of a patient's tissue that is of interest. In that manner, treatment of central nervous system lesions is possible.

Preferred MNCs and preferred methods of providing such MNCs are disclosed in PCT/JP03/01260, to Dezawa et al., entitled Method of Differentiating/Inducing Bone Marrow Interstitial Cells Into Nerve Cells and Skeleton Muscle Cells by Transferring Notch Gene ("Dezawa"). In particular, the "neural cells" of Dezawa, as described throughout Dezawa and in particular in Example 1, may be used as the MNCs of the present invention. Dezawa discloses that marrow-adherent stem cells may be transdifferentiated into neuronal cells that are then useful as the MNCs of the present invention.

In a preferred embodiment, MNCs may be produced from NPCs using neurotrophic agents. Useful neurotrophic agents include but are not limited to basic-fibroblast growth factor (bFGF), and ciliary neurotrophic factor (CNTF). Suitable methods of using neurotrophic agents with NPCs in vitro may be found in PCT/JP03/01260.

In embodiments, GFUs may be useful in the practice of this invention. Pharmaceutically acceptable carriers useful in GFUs of the present invention can include: sterile isotonic buffers, FRS, isolyte, sterile diluents such as water, normal saline, fixed oils, polyethylene glycols, glycerine, propylene glycol, or other synthetic solvents; antibacterial or antifungal agents such as ascorbic acid, thimerosal, trimethoprim-sulfamethoxazole, nalidixic acid, methenamine hippurate or nitrofurantoin macrocrystals and the like; antioxidants such as ascorbic acid or sodium bisulfite; chelating agents such as EDTA; buffers such as acetates, citrates, or phosphates; and agents for the adjustment of tonicity such as sodium chloride or dextrose. PH can be adjusted with acids or bases, such as hydrochloric acid or sodium hydroxide.

In an embodiment, graft forming units suitable for use in the present invention comprise sterile compositions that comprise MNCs. For intravenous administration, suitable pharmaceutically acceptable carriers may include physiological saline, Cremophor EL.™ (BASF; Parsippany, N.J.), normasol, isolyte, plasma-lyte, or phosphate buffered saline (PBS). In all cases, the GFU must be sterile (other than any NPCs or MNCs that are present) and should be fluid to the extent that easy syringability exists (proper fluidity can be maintained, for example, by using materials such as lecithin, by maintaining a certain particle size in the case of dispersion, and by including surfactants). The GFU must be stable under the conditions of manufacture and storage and must be preserved against the contaminating action of microorganisms such as bacteria and fungi, as described above. In certain cases, it will be preferable to include, for example, sugars, polyalcohols such as mannitol or sorbitol, sodium chloride, LiCl, Na butyrate, and sodium orthovanadate in the GFU. Generally, the inventive GFUs may be prepared by incorporating the NPCs into a sterile vehicle which contains a basic dispersion medium and optionally other ingredients from those enumerated above.

It is especially advantageous to formulate the GFUs of the invention in graft forming unit dosage forms for ease of administration and uniformity of dosage. Graft forming unit dosage form as used herein refers to physically discrete units suited as unitary dosages for the subject to be treated. In an embodiment each GFU dosage form contains a predetermined quantity of MNCs calculated to produce the desired therapeutic effect in association with the required pharmaceutical carrier. The specification for the graft forming unit dosage forms of the invention are dictated by and directly dependent on the unique characteristics of the MNCs, the particular therapeutic effect to be achieved, and the limitations inherent in the art of compounding MNCs for the treatment of individuals. The number of MNPs in each graft unit dosage form preferably can vary from about 1000 cells to about 1 billion cells, preferably from about 10,000 cells to about 100 million cells, more preferably from about 50,000 cells to about 50 million cells. The concentration of MNCs in each graft unit dosage form preferably can vary from about 100 cells/µL to about 100,000 cells/µL, and more preferably from about 1,000 cells/µL to about 50,000 cells/µL.

The GFUs can be included in a container, pack, or dispenser together with instructions for administration. The grafts are preferably stored at approximately 4° C.

In certain non-clinical embodiments it may be desirable to label the MNCs prior to transplantation. This may be desirable in order to track the migration of transplanted MNCs, further changes to transplanted MNCs, survival of transplanted MNCs, and so on. Various cell labeling methods may be employed depending on the circumstances under which the labels are to be read. For instance, fluorescent proteins (green fluorescent protein, red fluorescent protein, etc.) may be used as in circumstances in which a detector can be suitably placed near the transplant site. Labeling may be performed using conventional methods, such as the Invitrogen GFP-lentiviral system noted above.

When analyzing engrafted brains in non-clinical situations, immunohistochemical analysis may be useful. In an embodiment, brain sections may be doubly-immunostained for green fluorescent protein (GFP) or other cell labels, β-tubulin III, NeuN (a neuron-specific protein), glial fibrillary acidic protein (GFAP), or O4 (an oligodendrocyte-specific protein) to identify neuronal, astrocytic, glial, or oligodendrocytic profiles. The number of positive profiles for a given antibody and the number of cells expressing GFP may be estimated according to the Abercrombie correction formula. The volume of distribution and total GFP (or other label) positive profiles may be calculated by determining the area of the brain containing at least 10% GFP-positive (or other label-positive) profiles in every fifth section and multiplying by the distance from the anterior aspects of the brain that contain GFP-positive (or other label-positive) profiles. In an embodiment, MNCs may be fluourescenty labeled using retroviral infection via the pBabe neo-GFP vector. M. Dezawa et al., "Sciatic nerve regeneration in rats induced by transplantation of in vitro differentiated bone-marrow stromal cells." Eur J Neurosci. 2001; 14:1771-6. The procedure may be modified such that other fluorescent proteins may be incorporated into the vector.

C. NPC Transplantation

In an embodiment, NPCs and/or GFUs according to the invention may be administered using conventional protocols and routes of administration, and amounts of NPCs and/or GFUs to be administered to patients can be optimized using conventional dose ranging techniques. NPCs and/or GFUs according to the present invention may be administered alone or in combination with other substances or compositions. Routes of administration may be chosen from conventional routes of administration known to one of skill in the art.

It is contemplated that transplantation will be carried out by a variety of methods, including but not limited to infusion through an injection cannula, needle or shunt, or by implantation within a carrier, e.g., a biodegradable capsule, but other routes of administration, are also within the scope of the invention.

NPCs and/or GFUs according to the invention may be administered systemically to a patient, in which instance parenteral routes such as intravenous (i.v.), or intra-arterial (such as through internal or external carotid arteries) administration are preferred routes of systemic administration. Systemic administration techniques can be adapted from techniques used to administer precursor cells generally, such as those disclosed in D Lu et al., "Intraarterial administration of marrow stromal cells in a rat model of traumatic brain injury." J Neurotrauma. 2001 August; 18(8):813-9.

In embodiments, NPCs and/or GFUs according to the invention may be administered locally to a patient's central nervous system lesion. In a preferred embodiment, the NPCs and/or GFUs of the present invention may be administered through an intraparenchymal route. An advantage of administering the NPCs and/or GFUs locally to a patient's central nervous system lesion is that the patient's immune system may be less active inside the blood-brain barrier. Therefore, the chances of immunorejection of the NPCs by the host may be reduced, and the chances of graft survival may be increased even though immunosuppressants still may be required. Another advantage of local administration is more precise targeting of NPCs to the CNS lesion.

When transplanting into a central nervous system lesion, transplantation may be carried out using stereotactic surgical procedures. In such procedures, the patient is anesthetized. The patient's head is placed in an MRI compatible stereotactic frame and the micropositioner with micro-injector placed over the skull. Burr holes may be made in the patient's skull using a dental drill or other suitable instrument to expose areas of the dura just above the target sites.

In an embodiment, a needle pass using a 26-gauge needle and Hamilton micro-syringe (or other suitable size syringe) may be made, in which the needle is manually guided to the graft sites using MRI images to insure proper placement of the NPCs and/or GFU. Injections, preferably as bolus injections, may be made to the graft site(s). Infusions rates can vary, preferably infusion volumes are from about 0.1 to about 10 µL/min, more preferably from about 0.5 to about 5 µL/min, and still more preferably from about 1.0 to about 3.0 µL/min. In an embodiment, the needle may be left in place for a period of time, preferably ranging from about 1 to about 10 minutes, more preferably about 5 minutes, following infusion. Following the period wherein the needle is left in place, the needle may be raised a short distance, preferably about 1 mm to about 10 mm, more preferably about 2 mm and then held in place for an additional period of time, preferably ranging from about 5 minutes to about 30 minutes, more preferably about 15 minutes. The syringe may then be removed from the patient, the wound site can be closed in anatomical layers, and the patient monitored for recovery from anesthesia.

Analgesics, (e.g., buprenorphine) and antibiotics (e.g., Cephazolin, 50 mg/kg, IM, b.i.d.×5 days) may be administered, as needed, as part of the surgical/post-surgical procedures. Antibiotic treatment may be continued post-surgically for an extended period, preferably up to 30 days following surgery, to suppress opportunistic infection.

Additional techniques for implantation may be found in K S Bankiewicz et al., "Technique for bilateral intracranial implantation of cells in monkeys using an automated delivery system." Cell Transplantation, 9(5):595-607 (2000).

In certain embodiments, immunosuppressive agents may be administered together with the inventive grafts and/or NPCs. These agents may help to suppress rejection of the NPCs by the patient's immune system, particularly when the graft and/or NPCs are administered systemically. Examples of immunosuppressants useful in the practice of this invention include, but are not limited to antimetabolites such as azathioprine, alkylating agents such as cyclophosphamide, folic-acid antagonists such as methotrexate or mercaptopurine (6-MP), mycophenolate (CellCept), Cyclosporine-A and Tacrolimus (FK-506). A preferred immunosuppressive agent is CsA. CsA may obtained from a variety of sources, including as Sandimmune®, Injection; manufactured by Novartis Pharma AG, Basel, Switzerland for Novartis Pharmaceuticals Corporation (Novartis), East Hanover, N.J.

Immunosuppressants may be administered by a variety of routes, including oral, i.p., and i.v. Dosing of immunosuppressants may vary according to the nature of the immunosuppressant and the patient. In an embodiment, the immunosuppressant may be dosed two days prior to transplantation and continuing at suitable intervals thereafter. In an embodiment, the immunosuppressant may be dosed beginning on the day of grafting (approximately four hours post-procedure) and continuing at 24-hour intervals thereafter. Dosage ranges preferably may vary from about 0.5 mg/kg/day to about 100 mg/kg/day, more preferably from about 5 mg/kg/day to about 75 mg/kg/day, still more preferably from about 5 mg/kg/day to about 50 mg/kg/day. Intravenous injections may be administered as a bolus, at a rate ranging preferably from about 0.005 to about 0.100 mL/minute, more preferably at about 0.050 mL/minute.

NPCs and/or GFUs according to the invention may be administered using conventional protocols and routes of administration, and amounts of NPCs and/or GFUs to be administered to patients can be optimized using conventional dose ranging techniques. NPCs and/or GFUs according to the present invention may be administered alone or in combination with other substances or compositions. Routes of administration may be chosen from conventional routes of administration known to one of skill in the art.

It is contemplated that transplantation will be carried out by a variety of methods, including but not limited to infusion through an injection cannula, needle or shunt, or by implantation within a carrier, e.g., a biodegradable capsule, but other routes of administration, are also within the scope of the invention.

In embodiments, NPCs and/or GFUs according to the invention may be administered locally to a patient's central nervous system lesion. In a preferred embodiment, the NPCs and/or GFUs of the present invention may be administered through an intraparenchymal route. An advantage of administering the NPCs and/or GFUs locally to a patient's central nervous system lesion is that the patient's immune system may be less active inside the blood-brain barrier. Therefore, the chances of immunorejection of the NPCs by the host may be reduced, and the chances of graft survival may be increased even though immunosuppressants still may be required. Another advantage of local administration is more precise targeting of NPCs to the CNS lesion.

D. MASC-Derived Neuronal Cell Transplantation

In an embodiment, MNCs and/or GFUs according to the invention may be administered using conventional protocols and routes of administration, and amounts of MNCs and/or GFUs to be administered to patients can be optimized using conventional dose ranging techniques. MNCs and/or GFUs according to the present invention may be administered alone or in combination with other substances or compositions. Routes of administration may be chosen from conventional routes of administration known to one of skill in the art.

It is contemplated that transplantation will be carried out by a variety of methods, including but not limited to infusion through an injection cannula, needle or shunt, or by implantation within a carrier, e.g., a biodegradable capsule, but other routes of administration, are also within the scope of the invention.

In embodiments, MNCs and/or GFUs according to the invention may be administered locally to a patient's central nervous system lesion. In a preferred embodiment, the MNCs and/or GFUs of the present invention may be administered through an intraparenchymal route. An advantage of administering the MNCs and/or GFUs locally to a patient's central nervous system lesion is that the patient's immune system may be less active inside the blood-brain barrier. Therefore, the chances of immunorejection of the MNCs by the host may be reduced, and the chances of graft survival may be increased even though immunosuppressants still may be required. Another advantage of local administration is more precise targeting of MNCs to the CNS lesion.

When transplanting into a central nervous system lesion, transplantation may be carried out using stereotactic surgical procedures. In such procedures, the patient is anesthetized. The patient's head is placed in an MRI compatible stereotactic frame and the micropositioner with micro-injector placed over the skull. Burr holes may be made in the patient's skull using a dental drill or other suitable instrument to expose areas of the dura just above the target sites.

In an embodiment, a needle pass using a 26-gauge needle and Hamilton micro-syringe (or other suitable size syringe) may be made, in which the needle is manually guided to the graft sites using MRI images to insure proper placement of the MNCs and/or GFU. Injections, preferably as bolus injections, may be made to the graft site(s). Infusions rates can vary, preferably infusion volumes are from about 0.1 to about 10 µL/min, more preferably from about 0.5 to about 5 µL/min, and still more preferably from about 1.0 to about 3.0 µL/min. In an embodiment, the needle may be left in place for a period of time, preferably ranging from about 1 to about 10 minutes, more preferably about 5 minutes, following infusion. Following the period wherein the needle is left in place, the needle may be raised a short distance, preferably about 1 mm to about 10 mm, more preferably about 2 mm and then held in place for an additional period of time, preferably ranging from about 5 minutes to about 30 minutes, more preferably about 15 minutes. The syringe may then be removed from the patient, the wound site can be closed in anatomical layers, and the patient monitored for recovery from anesthesia.

Analgesics, (e.g., buprenorphine) and antibiotics (e.g., Cephazolin, 50 mg/kg, IM, b.i.d.×5 days) may be administered, as needed, as part of the surgical/post-surgical procedures. Antibiotic treatment may be continued post-surgically for an extended period, preferably up to 30 days following surgery, to suppress opportunistic infection.

Additional techniques for implantation may be found in K S Bankiewicz et al., Technique for bilateral intracranial implantation of cells in monkeys using an automated delivery system. Cell Transplantation, 9(5):595-607 (2000).

In certain embodiments, immunosuppressive agents may be administered together with the inventive grafts and/or MNCs. These agents may help to suppress rejection of the MNCs by the patient's immune system. Examples of immunosuppressants useful in the practice of this invention include, but are not limited to antimetabolites such as azathioprine, alkylating agents such as cyclophosphamide, folic-acid antagonists such as methotrexate or mercaptopurine (6-MP), mycophenolate (CellCept), Cyclosporine-A and Tacrolimus (FK-506). A preferred immunosuppressive agent is CsA. CsA may obtained from a variety of sources, including as Sandimmune®, Injection; manufactured by Novartis Pharma AG, Basel, Switzerland for Novartis Pharmaceuticals Corporation (Novartis), East Hanover, N.J.

Immunosuppressants may be administered by a variety of routes, including oral, i.p., and i.v. Dosing of immunosuppressants may vary according to the nature of the immunosuppressant and the patient. In an embodiment, the immunosuppressant may be dosed two days prior to transplantation and continuing at suitable intervals thereafter. In an embodiment, the immunosuppressant may be dosed beginning on the day of grafting (approximately four hours post-procedure) and continuing at 24-hour intervals thereafter. Dosage ranges preferably may vary from about 0.5 mg/kg/day to about 100 mg/kg/day, more preferably from about 5 mg/kg/day to about 75 mg/kg/day, still more preferably from about 5 mg/kg/day to about 50 mg/kg/day. Intravenous injections may be administered as a bolus, at a rate ranging preferably from about 0.005 to about 0.100 mL/minute, more preferably at about 0.050 mL/minute.

E. Experimental Observations and Advantages of NPCs

Although both autologous and allogeneic transplantation of NPCs, including pharmaceutical compositions that comprise NPCs, are contemplated by this invention, allogeneic transplantation (same species graft forming units) is preferable. In an embodiment, allogeneic transplantation mimics the clinical setting in which allogeneic transplantation of NPCs in patients suffering from central nervous system lesion may take place. Disclosed herein are the results from stereotaxically transplantation of NPCs, according to the invention, into the brains of adult male Sprague-Dawley rats that have been subjected to middle cerebral artery occlusion (MCAo), middle cerebral artery ligation (MCAl) or transient global ischemia (TGI). These models are useful in understanding the efficacy of the present invention in the treatment of central nervous system lesions. Further discussion of these models can be found in the literature, particularly C. Borlongan et al., "Transplantation of cryopreserved human embryonal carcinoma-derived neurons (NT2N cells) promotes functional recovery in ischemic rats." Exp Neurol. 1998; 149:310-21; and C. Borlongan et al., "Glial cell survival is enhanced during melatonin-induced neuroprotection against cerebral ischemia." FASEB J. 2000; 14:1307-17. Each stroke animal received a graft comprising one of three cell doses: about 40,000, 100,000 and 200,000 viable NPCs (these numbers are understood to be approximate as used hereinafter). Transplantation was carried out at about 6 weeks post-stroke, and animals were immunosuppressed daily with Cyclosporine-A (10 mg/kg, i.p.) throughout the post-transplantation survival time. Locomotor and cognitive performance of transplanted rats was characterized weekly over a period of 4 weeks post-transplantation, and again once at 12 weeks post-transplantation. Histological examination of the extent of cerebral ischemia and graft survival was examined in randomly selected animals at 5 weeks and 12 weeks post-transplantation.

The following tests were used in the outcome determination of both the stroke operation and transplantation procedures as set forth in more detail below. The manner of performing these tests is set forth elsewhere herein, and would also be understood by one of skill in the art.

TABLE 1

PARAMETERS OF NPC TRANSPLANT EFFICACY

| Test | Objective |
|---|---|
| EBST | Reveals locomotor deficits after stroke and recovery after transplantation |
| Neurological exam | Reveals sensory-motor abnormalities after stroke and recovery after transplantation |
| Morris water maze | Reveals cognitive deficits after stroke and recovery after transplantation |
| TTC histology | Reveals extent of cerebral infarction |
| GFAP | Reveals extent of cerebral infarction and host immune response to transplant |
| GFP viral vector | Reveals survival and migration of grafted NPCs |
| Neu-N | Reveals neuronal phenotypic expression of grafted NPCs |

Legend:
EBST, elevated body swing test;
TTC, triphenyltetrazolium chloride;
GFAP, glial fibrially acidic protein The data obtained in the Examples below revealed that, in the models studied, animals transplanted with NPCs displayed significant improvements in both locomotor and cognitive performance compared to their pre-transplantation baseline performance. The two higher doses of about 100,000 and about 200,000 cells promoted better behavioral effects compared to the lower cell dose of about 40,000 cells, thus suggesting a dose-response relationship. Robust recovery from stroke-induced behavioral deficits was seen as early as one week post-transplantation and sustained over the four weeks post-transplantation period. Significant improvements in motor performance (using the elevated body swing test and Bederson test) were observed in all three stroke types. In contrast, significant improvements in cognitive performance (using the Morris Water Maze) were more robust and stable in MCAo and TGI transplanted animals compared to MCAl transplanted animals. All stroke transplanted animals looked healthy and there were no observable overt adverse effects during the study period.

The type of stroke appears to be a factor in functional recovery, in that while all stroke animals displayed significant improvements in motor performance, MCAo and TGI transplanted animals showed better recovery in cognitive performance compared to MCAl transplanted animals. The demonstration of significant recovery of both motor and cognitive functions in MCAo and TGI transplanted animals suggests that these two stroke models which produced basal ganglia and hippocampal damage, respectively, are responsive to NPC transplantation. Extrapolating these observations to clinical application would indicate that patients with fixed basal ganglia and hippocampal stroke may benefit from NPC transplantation.

Histological results at 5 and 12 weeks post-transplantation indicate that NPC graft survival mediated the observed functional effects. The data suggest that transplanting 100,000 and 200,000 NPCs produced better behavioral recovery than the lower dose of 40,000 cells. The correlational analyses between graft survival and behavioral effects further support that surviving NPCs promoted the motor and cognitive recovery in stroke animals. Of note, graft survival was determined using the lentivirus labeling approach, and this strategy was shown to be reliable for marking grafted NPCs. Furthermore, with this method, NPC migration was easily tracked.

Depending on the stroke type, it appears that the more severe the brain damage, as seen in both MCAo and MCAl, the better the migration of NPCs. In contrast, the mild brain damage caused by TGI appears to have resulted in less migration of the cells. The observed ability of NPCs to travel long-distance to the site of injury indicates its potential to migrate to and exert reparative effects on specific stroke target sites. The results provided in the Examples below support the view that NPCs that migrate are more likely to differentiate into neuronal phenotypes. There are many factors that might have contributed to this preferential differentiation of migrated cells, including but not limited to host microenvironment and type of stroke (location and degree/type of cell death).

Experimental Observations and Advantages of MNCs

Although both autologous and allogeneic transplantation of MNCs, including pharmaceutical compositions that comprise MNCs, are contemplated by this invention, allogeneic transplantation (same species grafts forming units) is preferable. In an embodiment, allogeneic transplantation mimics the clinical setting in which allogeneic transplantation of MNCs in patients suffering from central nervous system lesions may take place. The results from animals trials of allogenic transplantation of MNCs in animal models of stroke are provide in Section J below. These models are useful in understanding the efficacy of the present invention in the treatment of central nervous system lesions.

The results in Section H suggest that the MNC group showed significant improvements in the behavioral assessment tests compared with the control and MASC group. In histological analysis, the infarct volume measured at 41 days after MCAo did not show significant difference among three groups. Compared with MASCs, MNCs demonstrated higher survival ratio and larger proportion of MNCs showed neuronal marker positivity and neurite extetion in the host brain.

The MASC group demonstrated slight improvements in behavioral assessment tests compared with control group, but not as much as the NMC group.

Another advantage of MNC transplantation according to the invention is the greater survival rate of MNC as compared, for instance, with the multipotent MASCs. One month following transplantation, approximately 30-45% of transplanted MNCs were detected while only 10-20% of transplanted MASCs were detected. The greater survival rate of MNCs may provide an advantage in functional recovery.

In the current study, some MNCs in the cortex, striatum and hippocampus demonstrated extension of neuritis in the host brain, which could not be observed in the MASC-group. Hence the significant behavioral improvements in the MNC group suggested that the transplanted MNCs maintained neuronal characteristics in the host brain, and contributed to the functional recovery in the MCAO rat model.

G. NPC Examples

The Examples set forth herein are meant to be illustrative, and in no way limiting, of the scope of the present invention.

Experimental procedures. All animals initially received MCAo, MCAl or TGI stroke surgery. At about six weeks after the surgery, animals were tested on elevated body swing test, Bederson test, and Morris water maze task. Only animals that displayed significant motor deficits were subsequently used for transplantation surgery and randomly assigned to one of the following treatments. Sample size for each arm of the study is given in Table 2.

TABLE 2

TREATMENT CONDITIONS
Total rats used in this study

| Graft type (Approx.) | Cell dose | Stroke Type | Sample size |
|---|---|---|---|
| NPC | 40,000 | MCAo | 8 |
|  |  | MCAl | 10 |
|  |  | TGI | 8 |
|  | 100,000 | MCAo | 10 |
|  |  | MCAl | 10 |

TABLE 2-continued

TREATMENT CONDITIONS
Total rats used in this study

| Graft type (Approx.) | Cell dose | Stroke Type | Sample size |
|---|---|---|---|
|  |  | TGI | 8 |
|  | 200,000 | MCAo | 10 |
|  |  | MCAl | 10 |
|  |  | TGI | 8 |

All animals underwent stroke surgery, received transplants of 3 needle passes (MCAo and MCAI) or 2 needle passes (TGI), and were treated with daily cyclosporine-A (10 mg/kg, i.p.).

The animals underwent weekly testing for the first 4 weeks post-transplant. Half of animals were euthanized at 5 weeks post-transplant for histological analyses of the cerebral infarction and graft survival, phenotypic expression, and migration. The rest of the animals were again tested behaviorally and thereafter euthanized at 12 weeks post-stroke in order to assess long-term behavioral and histological effects of NPCs. For clarity, a schematic diagram is provided below.

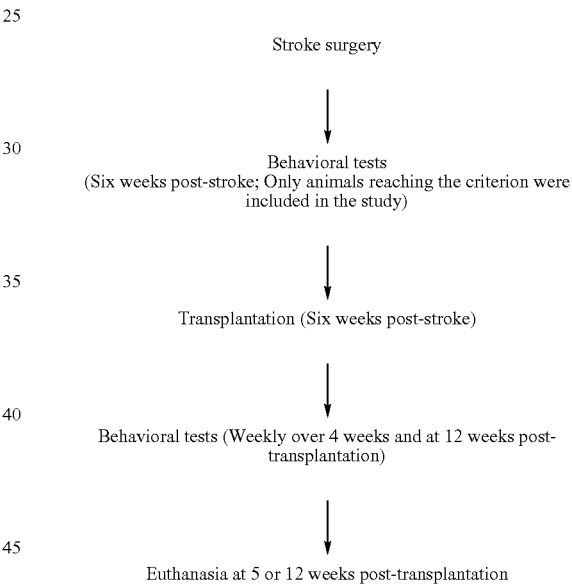

Cell Labelling Using GFP-Lentiviral vector system: The GFP-lentivirus system was supplied by Dr, Didier Trono of the University of Geneva (Geneva, Switzerland). NPCs were labeled using the following general scheme. Minor variations in method were tolerated.

Materials Needed 10 mg/mL polybrene stock solution/sterile filtered (Sigma)
Opti-MEM media (Gibco/Invitrogen)
1% Fetal Bovine serum with antibiotics (Penicillin/Streptomycin)
6 well plate approximately $1 \times 10^6$ San-Bio cells
Viral suspension Detailed Procedure 1. Warm cell media in 37° C. incubator.
2. Add polybrene to 10 μg/mL
   (Add 10 μL of a 10 mg/mL polybrene stock solution to 10 mL media. Mix well.)
3. In a separate tube, Add 1 mL viral suspension to 1 mL media containing polybrene.

4. Rapidly thaw a SanBio cell aliquot in a 37° C. water bath. Rinse vial with 70% Ethanol; wipe dry.
5. Add entire contents to a 15 mL centrifuge tube containing 10 mL pre-warmed PBS; mix gently and spin at 1000 RPMs on a low speed clinical centrifuge, room temperature, 5 minutes.
6. Gently pipet out the supernate and resuspend cell pellet in 2 mL prewarmed media containing virus. (from step 3)
7. Transfer contents to one well of a 6-well plate; place in the 37° C. incubator; Incubate for 3-hours
8. Wash cells in 10 mL prewarmed PBS, twice.
9. Resuspend cells in 20 µL PBS or media of choice. Transfer to a 1.5 mL Eppendorf tube. Keep on ice. Cells are ready for transplantation.

Behavioral tests: Animals were subjected to the following sensorimotor and cognitive behavioral measures in the pharmacology studies of NPCs according to the invention:

Elevated Body Swing Test (EBST)
Morris Water Maze (MWM)
Bederson Neurological Scale
Elevated Body Swing Test (EBST)

The elevated body swing test (EBST) measures basic postural reflexes and asymmetrical trunk function. The EBST test has been demonstrated to show a long lasting deficit following MCAo and MCAI ischemia in the rodent. C. Borlongan et al., "Locomotor and passive avoidance deficits following occlusion of the middle cerebral artery." Physiol Behav. 1995, 58:909-17. See also C. Borlongan et al., "Early assessment of motor dysfunctions aids in successful occlusion of the middle cerebral artery." Neuroreport. 1998b; 9:3615-21. It has also been evaluated in neural transplantation paradigms for chronic stroke. C. Borlongan et al., "Early assessment of motor dysfunctions aids in successful occlusion of the middle cerebral artery." Neuroreport. 1998; 9:3615-21.

EBST involves handling the animal by its tail and recording the direction of the swings. The test apparatus consisted of a clear Plexiglas box (40×40×35.5 cm). The animal was gently picked up at the base of the tail, and elevated by the tail until the animal's nose is at a height of 2 inches (5 cm) above the surface. The direction of the swing, either left or right, was counted once the animals head moved sideways approximately 10 degrees from the midline position of the body. After a single swing, the animal is placed back in the Plexiglas box and allowed to move freely for 30 seconds prior to retesting. These steps are repeated 20 times for each animal. Normally, intact rats display a 50% swing bias, that is, the same number of swings to the left and to the right. A 75% swing bias would indicate 15 swings in one direction and 5 in the other during 20 trials. Previous work with the EBST has noted that lesioned animals display >75% biased swing activity at one month after a nigrostriatal lesion; asymmetry is stable for up to six months Bederson Neurological Exam The Bederson Neurological scale measures sensorimotor tasks. J. Bederson et al., "Rat middle cerebral artery occlusion: evaluation of the model and development of a neurologic examination." Stroke. 1986; 17:472-6; M. Altumbabic, "Intracerebral hemorrhage in the rat: effects of hematoma aspiration." Stroke. 1998; 29:1917-22. Previous work has shown measurable deficit over time as measured by the Bederson model in both the MCAo and the MCAI stroke models in rat.

About one hour after the EBST, the Bederson Neurological exam is conducted following the procedures previously described. A neurologic score for each rat is obtained using 4 tests which include:

(a) observation of spontaneous ipsilateral circling, graded from 0 (no circling) to 3 (continuous circling);
(b) contralateral hindlimb retraction, which measures the ability of the animal to replace the hindlimb after it is displaced laterally by 2 to 3 cm, graded from 0 (immediate replacement) to 3 (replacement after minutes or no replacement);
(c) beam walking ability, graded 0 for a rat that readily traverses a 2.4-cm-wide, 80-cm-long beam to 3 for a rat unable to stay on the beam for 10 seconds; and
(d) bilateral forepaw grasp, which measures the ability to hold onto a 2-mm-diameter steel rod, graded 0 for a rat with normal forepaw grasping behavior to 3 for a rat unable to grasp with the forepaws.

The scores from all 4 tests, which are done over a period of about 15 minutes on each assessment day, are added to give a neurologic deficit score (maximum possible score, 12).

Morris Water Maze (MWM)

The Morris Water Maze assesses several aspects of cognitive functioning, including task acquisition and retention, search strategies, and perseveration. The water maze task is presumed to be sensitive to damage in several brain areas affected by MCAo including striatum and frontal cortex.

About one hour after the Bederson Neurological exam, animals are introduced to Morris water maze in order to assess spatial memory. The Morris water maze consists of an inflatable tank, 6 feet in diameter and 3 feet deep. The tank was filled with 12 cm of water and made opaque by adding 300 ml of milk. An 11-cm-tall platform made of clear Plexiglass with a circular surface 10 cm in diameter was placed into 1 of 4 positions in the pool. The platform is 1 cm below the surface of the water and thus hidden from the view of an animal in the water. The pool is divided into four quadrants of equal surface area. The test rat was placed in the pool facing the side of the tank and released at 1 of 4 starting positions (north, south, east, or west), which was randomly determined, and were located arbitrarily at equal distances on the pool rim. The platform was located in the middle of the south-west quadrant 25 cm from the pool rim. The start point was changed after each trial. The animal was given approximately 60 seconds to find the platform and allowed to rest on the platform for approximately 30 seconds and placed back in starting position, for a total of 3 tests from starting positions determined at random. If the rat failed to find the hidden platform within approximately 60 seconds, it was placed on the platform and allowed to rest on the platform for approximately 30 seconds. After the rest period, the rat was placed back in the tank and was tested again for 2 more trials. The training day consisted of 3 trials. The testing day was conducted on day 2 (for probe trial, see below). After each training trial and testing, the rat was then placed in a cage on top of a heating pad. The swim paths were monitored by a video camera connected to a computer through an image analyzer. Escape latency time to reach the platform and path length the animal swam to find the platform were used to assess acquisition of the water-maze task. Swimming speed=path length/escape latency was used to assess the motoric activity of rats in this task. To assess recall of the platform position, a 60-second probe trial with no platform in the pool was undertaken on day 2; the percentage of time spent in the former platform position was monitored.

MCAo stroke surgery: All surgical procedures were conducted under aseptic conditions. MCAo stroke procedures were taken from the literature, in particular from C. Borlongan et al., "Chronic cyclosporine-A injection in rats with damaged blood-brain barrier does not impair retention of passive avoidance." Neurosci Res. 1998, 32:195-200. Determination in each animal of successful occlusion was attained using a Laser Doppler that revealed significant (>75%) reduction in cerebral blood flow during the 1-hour occlusion. MCAo produced consistent striatal damage.

MCAI stroke surgery: The MCAI surgical procedure is described generally in Y. Wang et al., "Glial Cell-Derived Neurotrophic Factor Protects Against Ischemia-Induced Injury in the Cerebral Cortex." 1997, J. Neuroscience; 17 (11):4341-4348. The Laser Doppler was also used to verify arterial ligation. MCAI produces consistent cortical damage.

TGI stroke surgery: A 4-vessel occlusion technique was used. Under deep anesthesia, animals received a ventral midline cervical incision. The vertebral arteries were isolated through the alar foramina of the first cervical vertebra and microclips were used to ligate both common carotid arteries for 15 minutes. This technique has been shown to produce global cerebral ischemia, with consistent hippocampal damage.

Neuronal Precursor Cells: Neuronal Precursor Cells were provided by SanBio, Inc. (Mountain View Calif.). These cells were produced generally according to the teachings of PCT/JP03/01260.

Grafting Procedures: All surgical procedures were conducted under aseptic conditions. Under equithesin (3 ml/kg i.p.) anesthesia (animals checked for pain reflexes), the animals were implanted with NPCs directly into the striatum for MCAo, the cortex for MCAI or the hippocampus for TGI, using a 26-gauge implantation cannula. See generally Y. Wang et al., "Glial Cell-Derived Neurotrophic Factor Protects Against Ischemia-Induced Injury in the Cerebral Cortex" 1997, J. Neuroscience; 17 (11):4341-4348 and C. Borlongan et al., "Transplantation of cryopreserved human embryonal carcinoma-derived neurons (NT2N cells) promotes functional recovery in ischemic rats." Exp Neurol. 1998; 149:310-21. Cryopreserved NPCs were obtained using the methods disclosed herein. Viability cell counts, using Tryphan Blue exclusion method, were conducted prior to transplantation and immediately after the transplantation on the last animal recipient. The pre-determined cell doses (40,000, 100,000 and 200,000) referred to number of viable cells. Transplantation surgery were carried out within 2 hours after thawing the cells. Infusion rate was 1 ul of cell solution per minute. Following infusion, a 3-minute absorption period was allowed before the needle was retracted. A heating pad and a rectal thermometer maintained body temperature at about 37 Deg C. throughout surgery and until recovery from anesthesia.

Statistical analysis: Behavioral data were analyzed using repeated measures of ANOVA with statistical significance set at $p<0.05$. Posthoc tests included compromised t-tests to reveal significant differences ($p$'s$<0.05$) between treatment conditions.

Example 1

MCAo Results—Weekly for Four Weeks Post-Transplantation

The test animals underwent the MCAo procedure as described above, and were evaluated weekly for four weeks port-transplantation with the following results.

Figure 2:
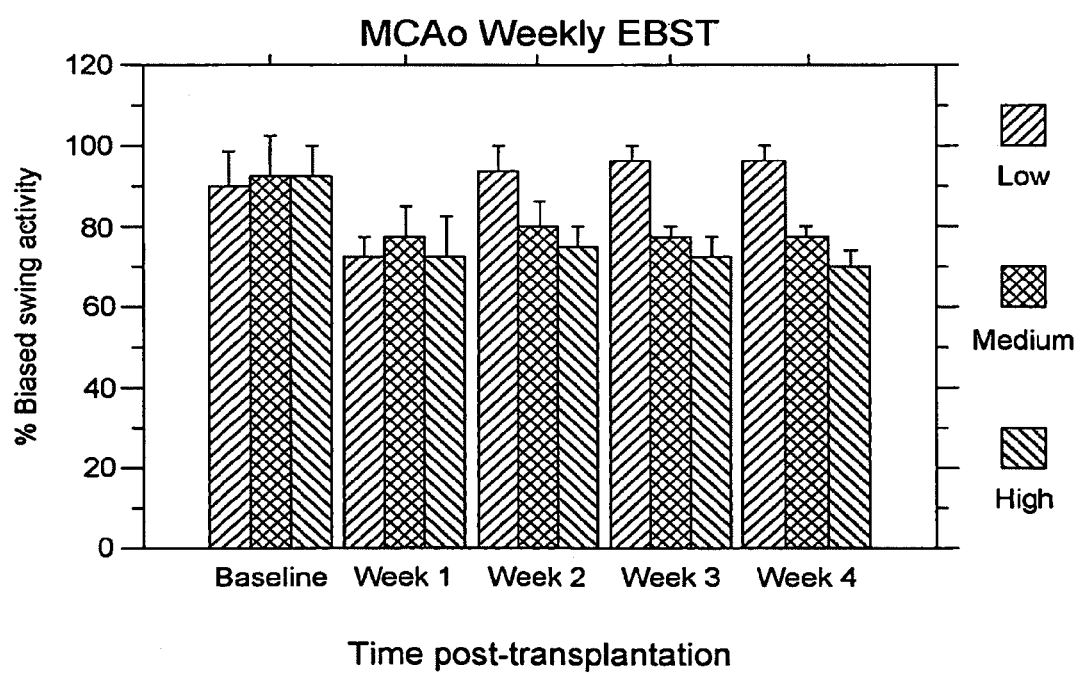
FIG. 2 shows results from the MCAo procedure.

EBST: For the weekly testing over the four weeks post-transplantation, overall ANOVA revealed significant main treatment effects ($F2,21=57.06$, $p<0.0001$) (FIG. 1). Dose-dependent significant effects (200,000>100,000>40,000) were also observed ($p$'s$<0.01$). The motor asymmetry was significantly reduced in each of the four weeks post-transplantation compared to baseline ($p$'s$<0.0001$), with the most robust recovery seen at one week post-transplantation ($p$'s$<0.0001$), and with stable recovery displayed for the subsequent three weeks post-transplantation. Posthoc tests revealed that the significant reduction in motor asymmetry at 1 week post-transplantation did not differ across the three cell doses, but dose-dependent effects were seen at 2, 3 and 4 weeks post-transplantation ($p$'s$<0.05$) (FIG. 2).

Figure 3:
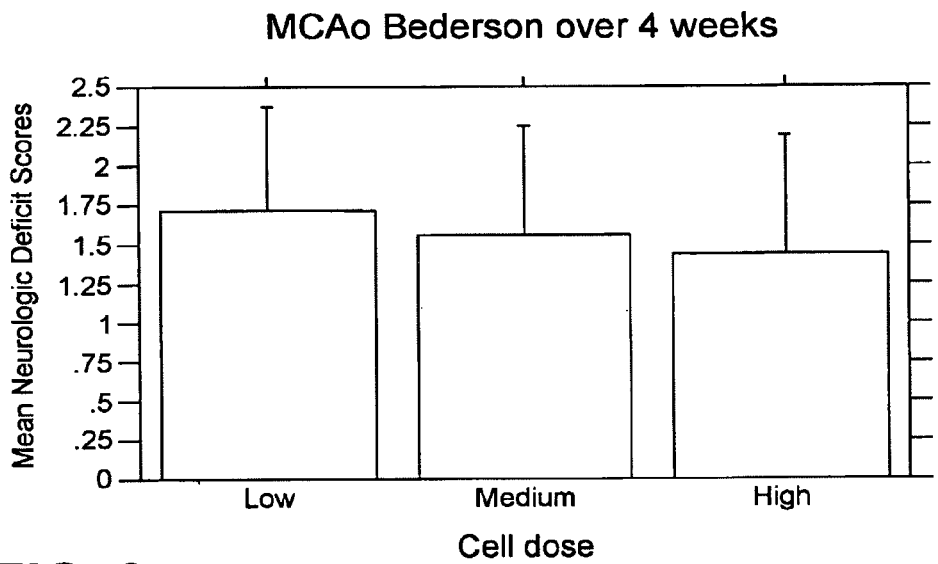
FIG. 3 shows results from the MCAo procedure.
Figure 4:
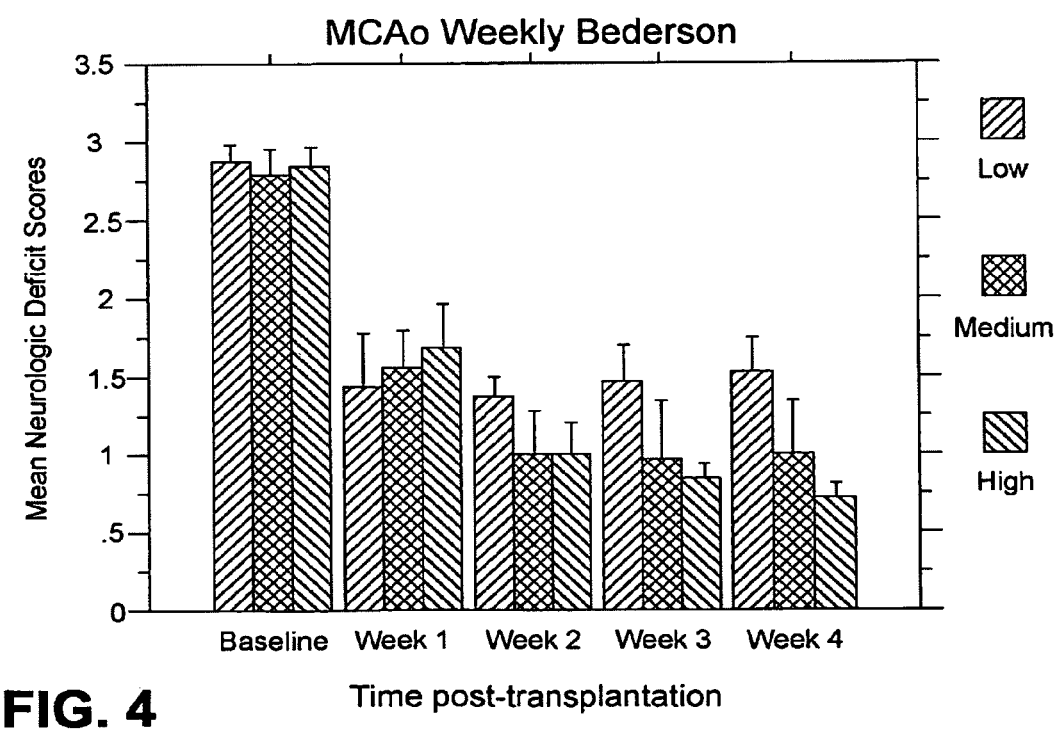
FIG. 4 shows results from the MCAo procedure.

Bederson test: For the weekly testing over the four weeks post-transplantation, overall ANOVA revealed significant main treatment effects ($F2,21=9.65$, $p<0.001$) (FIG. 3). The higher doses of 200,000 and 100,000 cells promoted better improvement in neurologic deficit scores than the low dose of 40,000 cells ($p$'s$<0.01$). Improvements in neurologic deficit scores were significantly reduced in each of the four weeks post-transplantation compared to baseline ($p$'s$<0.0001$), with a trend towards better improvement over time in that transplanted animals performed better at 2, 3 and 4 weeks post-transplantation compared to 1 week post-transplantation ($p$'s$<0.0001$). Posthoc tests revealed that the significant reduction in neurologic deficit scores at 1 week post-transplantation did not differ across the three cells doses, but the high doses 100,000 and 200,000 produced better recovery than the low dose 40,000 cells at 2 weeks ($p$'s$<0.05$), and dose-dependent effects (200,000>100,000>40,000) were seen at 3 and 4 weeks post-transplantation ($p$'s$<0.05$) (FIG. 4).

Figure 5:
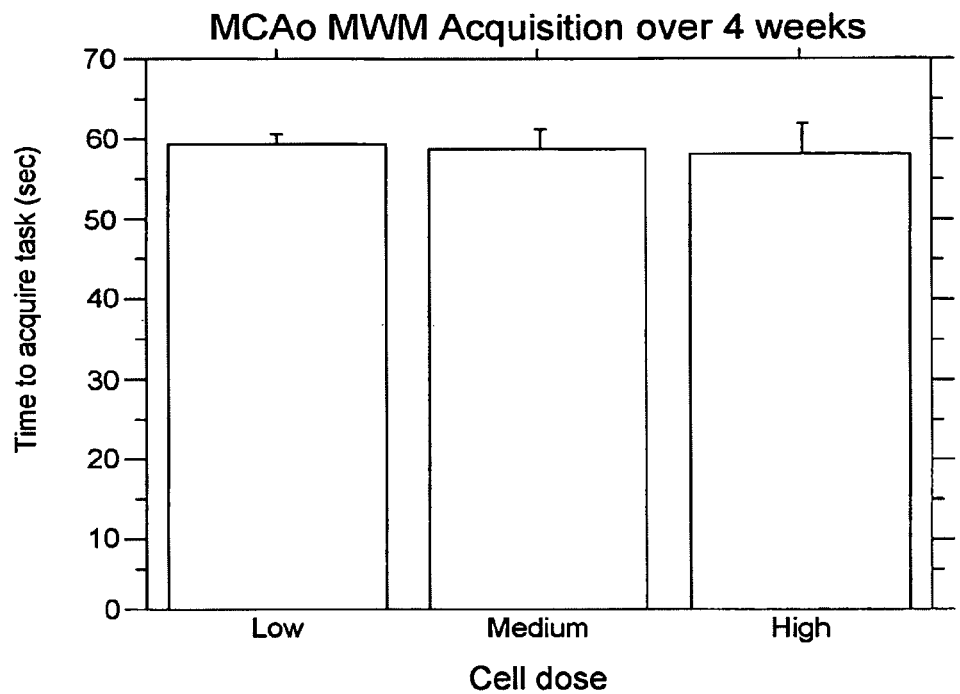
FIG. 5 shows results from the MCAo procedure.
Figure 6:
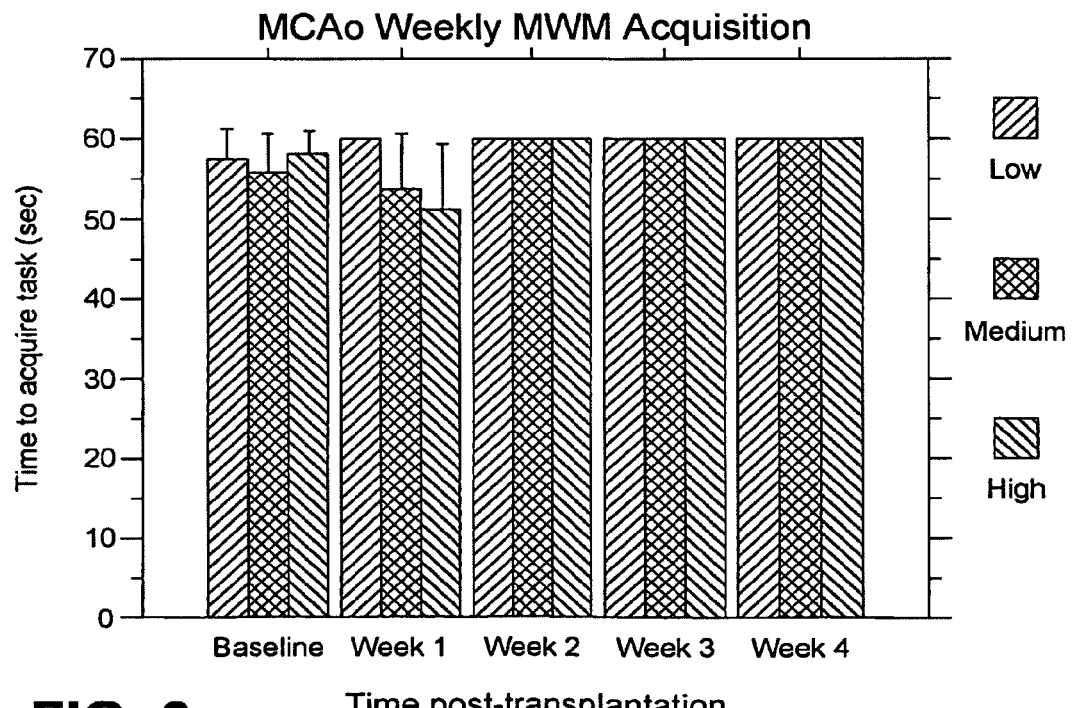
FIG. 6 shows results from the MCAo procedure.

MWM Acquisition: For the weekly testing over the four weeks post-transplantation, overall ANOVA revealed no significant main treatment effects ($F2,21=2.87$, $p=0.08$) (FIG. 5). There appears to be a trend towards longer MWM acquisition time over the 4 weeks post-transplantation period as revealed by longer acquisition times at 2, 3 and 4 weeks compared to baseline and 1 week post-transplantation ($p$'s$<0.01$) (FIG. 6).

Figure 7:
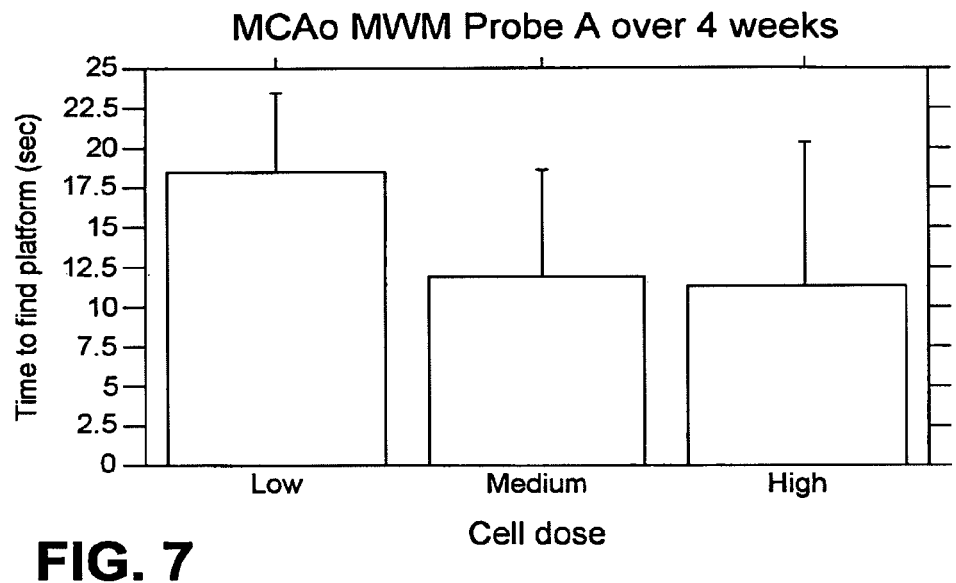
FIG. 7 shows results from the MCAo procedure.
Figure 8:
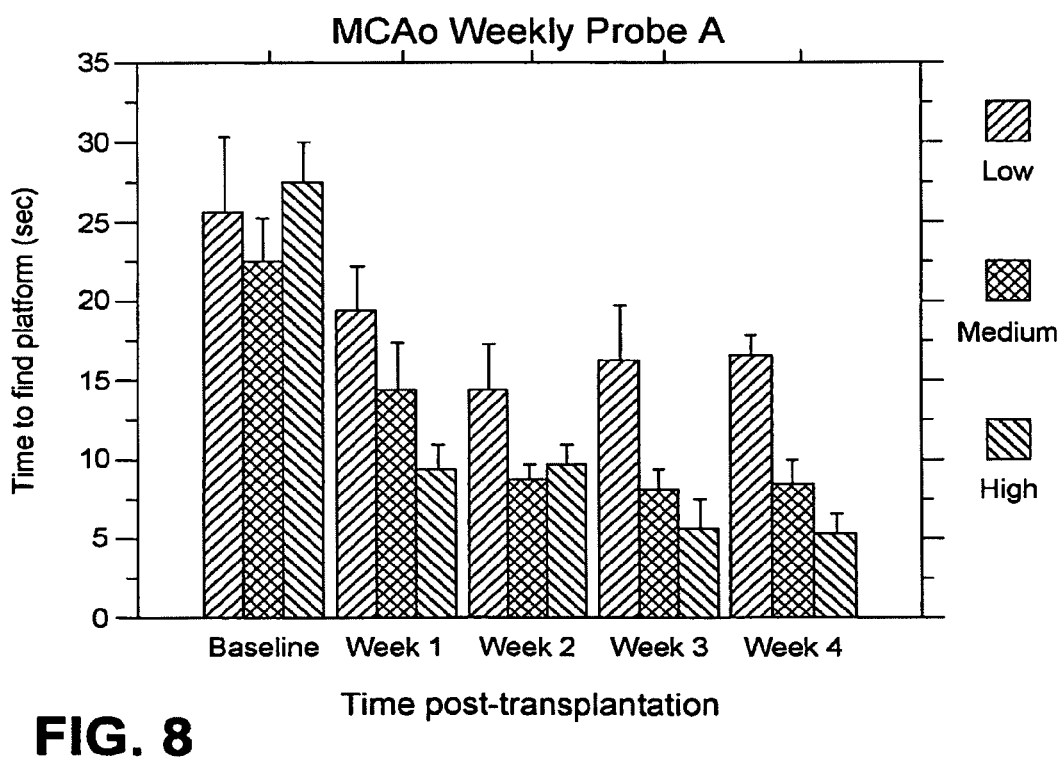
FIG. 8 shows results from the MCAo procedure.

MWM Probe test: Time to find the platform. For the weekly testing over the four weeks post-transplantation, overall ANOVA revealed significant main treatment effects ($F2, 21=61.33$, $p<0.0001$) (FIG. 7). The higher doses of 200,000 and 100,000 cells promoted significantly shorter time locating the platform than the low dose of 40,000 cells ($p$'s$<0.0001$). Improvements in the time to find the platform were significantly reduced in each of the four weeks post-transplantation compared to baseline ($p$'s$<0.0001$), with a trend towards better improvement over time in that transplanted animals performed better at 2, 3 and 4 weeks post-transplantation compared to 1 week post-transplantation ($p$'s$<0.0001$). Posthoc tests revealed that the higher doses of 200,000 and 100,000 produced significantly shorter times to find the platform than the low dose 40,000 cells across the 4-week post-transplantation period, with clear dose-dependent response (200,000>100,000>40,000) seen at 1 and 4 weeks post-transplantation ($p$'s c 0.05) (FIG. 8).

Figure 9:
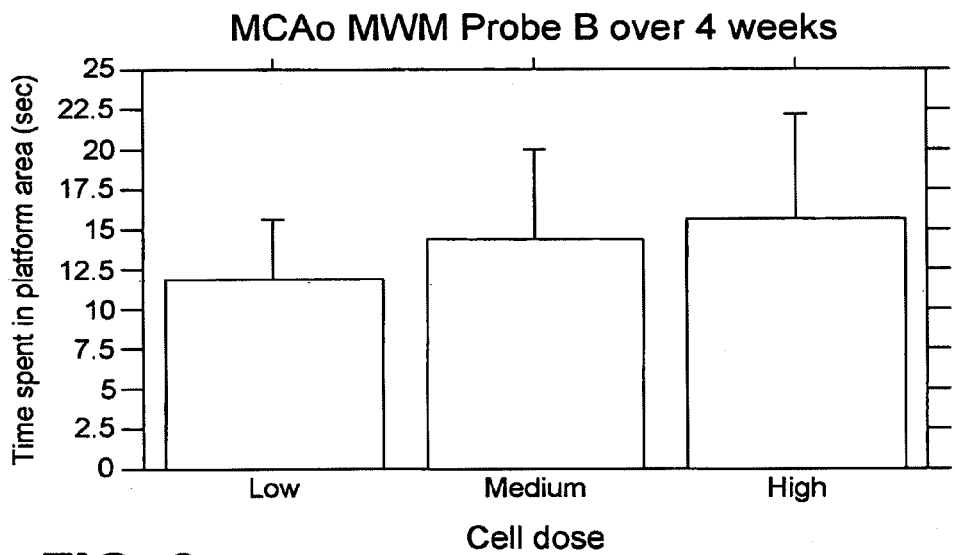
FIG. 9 shows results from the MCAo procedure.
Figure 10:
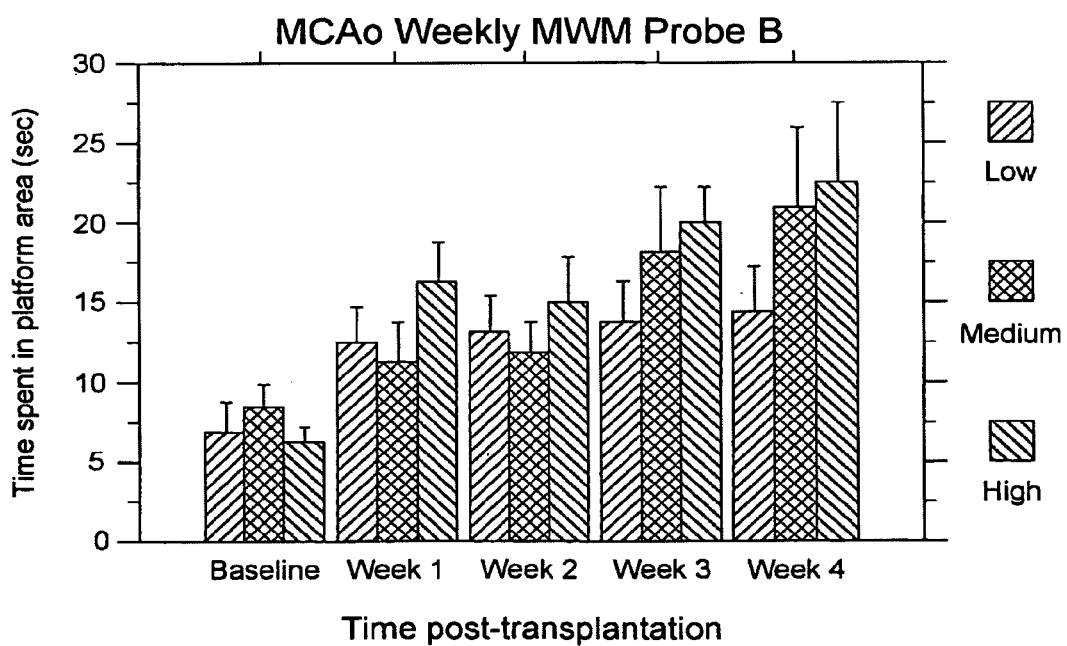
FIG. 10 shows results from the MCAo procedure.

MWM Probe test: Time spent on the platform area. For the weekly testing over the four weeks post-transplantation, overall ANOVA revealed significant main treatment effects ($F2, 21=15.19$, $p<0.0001$) (FIG. 9). The higher doses of 200,000 and 100,000 cells promoted significantly longer times spent in the platform area than the low dose of 40,000 cells ($p$'s$<0.01$). Times spent in the platform area were significantly increased in each of the four weeks post-transplantation compared to baseline ($p$'s$<0.0001$), with a trend towards better improvement over time in that transplanted animals performed better at 3 and 4 weeks post-transplantation compared to 1 and 2 weeks post-transplantation ($p$'s$<0.0001$). Posthoc tests revealed that the higher doses of 200,000 and 100,000 produced significantly longer times spent in the platform area than the low dose 40,000 cells across the 4-week post-transplantation period (p's<0.05) (FIG. 10).

Example 2

MCAI Results—Weekly for Four Weeks
Post-Transplantation

The test animals underwent the MCAI procedure as described above, and were evaluated weekly for four weeks post-transplantation with the following results.

Figure 11:
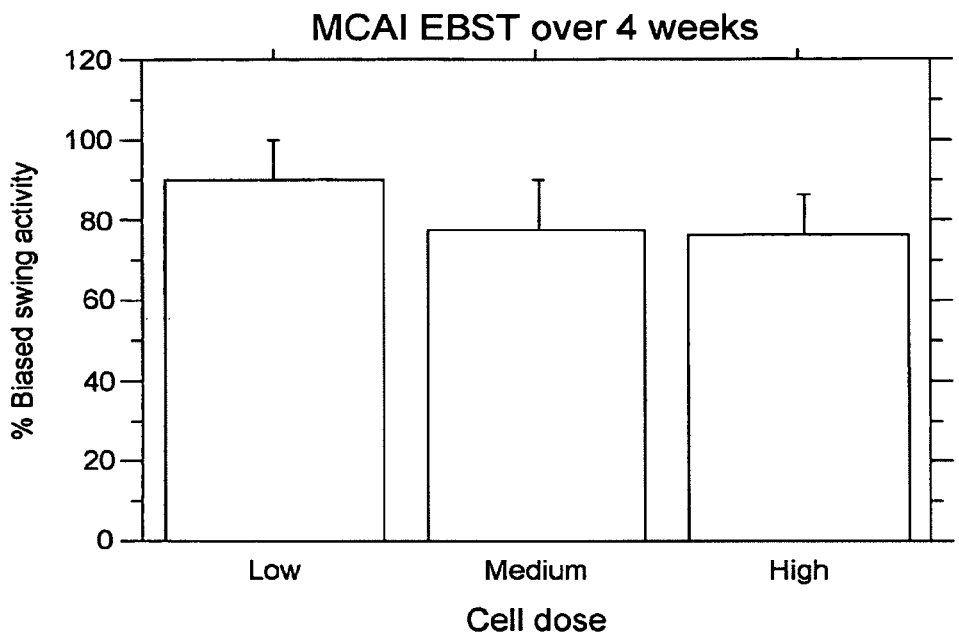
FIG. 11 shows results from the MCAI procedure.
Figure 12:
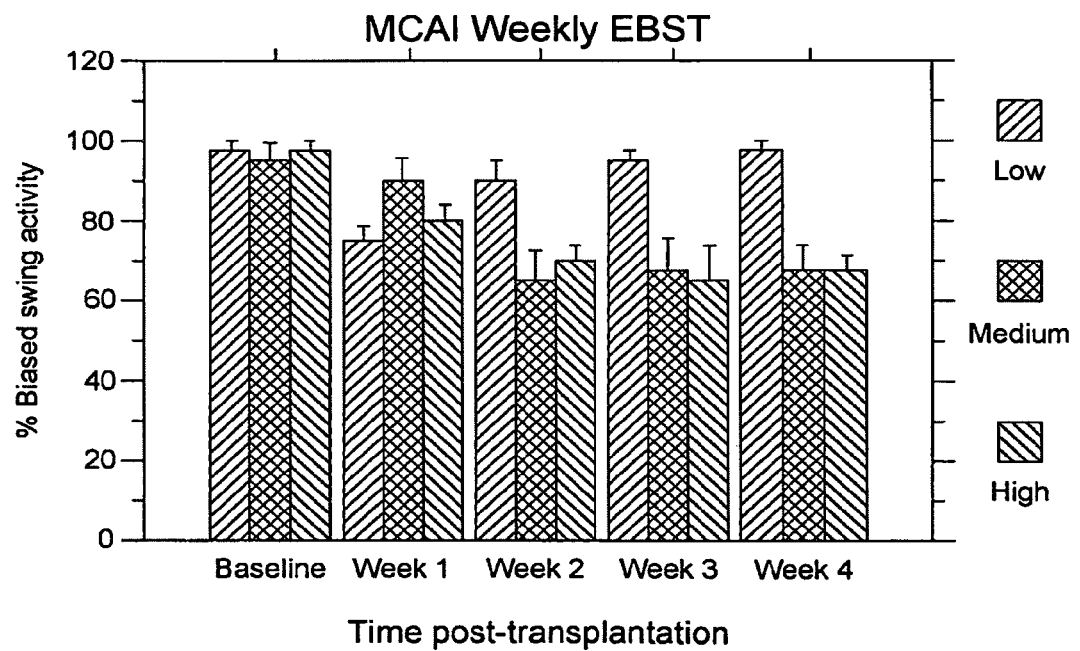
FIG. 12 shows results from the MCAI procedure.

EBST: For the weekly testing over the four weeks post-transplantation, overall ANOVA revealed significant main treatment effects ($F_{2,24}=76.30$, $p<0.0001$) (FIG. 11). The higher doses of 200,000 and 100,000 cells produced better recovery from motor asymmetry than the low dose of 40,000 cells (p's<0.0001). The motor asymmetry was significantly reduced in each of the four weeks post-transplantation compared to baseline (p's<0.0001), with better recovery displayed at 2, 3 and 4 weeks post-transplantation. Posthoc tests revealed that the higher cell doses significantly reduced motor asymmetry better than the low dose, with dose-dependent effects (200,000>100,000>40,000) seen at 1 week post-transplantation (p's <0.05) (FIG. 12).

Figure 13:
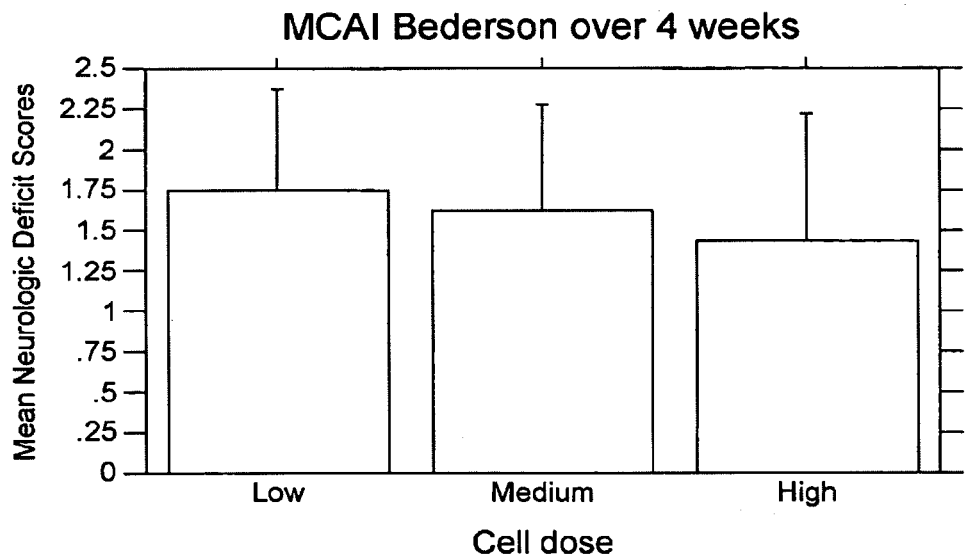
FIG. 13 shows results from the MCAI procedure.
Figure 14:
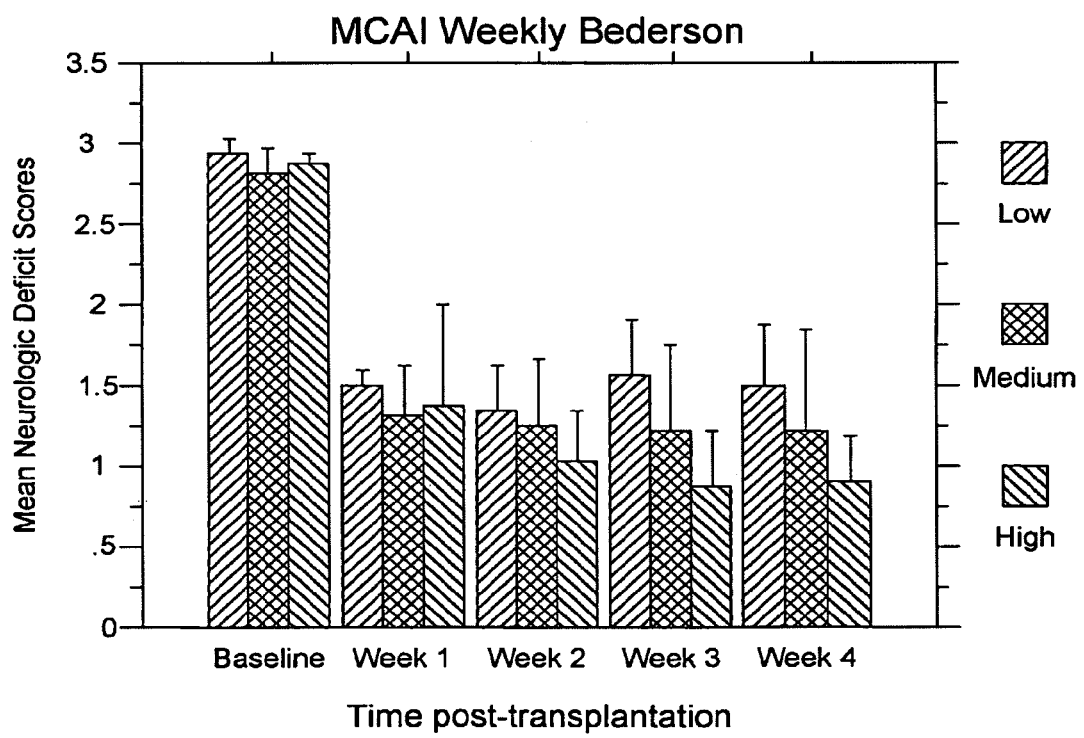
FIG. 14 shows results from the MCAI procedure.

Bederson test: For the weekly testing over the four weeks post-transplantation, overall ANOVA revealed significant main treatment effects ($F_{2,24}=3.65$, $p<0.05$) (FIG. 13). The highest dose of 200,000 cells promoted better improvement in neurologic deficit scores than the low dose of 40,000 cells (p's<0.05); no significant differences were found between the medium dose of 100,000 cells and the low dose of 40,000 cells. (FIG. 13) Improvements in neurologic deficit scores were significantly reduced in each of the four weeks post-transplantation compared to baseline (p's<0.0001), and stable over time as there were no significant differences between cell doses across the weekly neurologic scores (p's>0.005). Posthoc tests revealed that the highest dose of 200,000 cells produced better recovery than the low dose 40,000 cells at 3 and 4 weeks (p's<0.01); no other significant differences were found between cell doses at earlier time points post-transplantation (p's>0.05) (FIG. 14).

Figure 15:
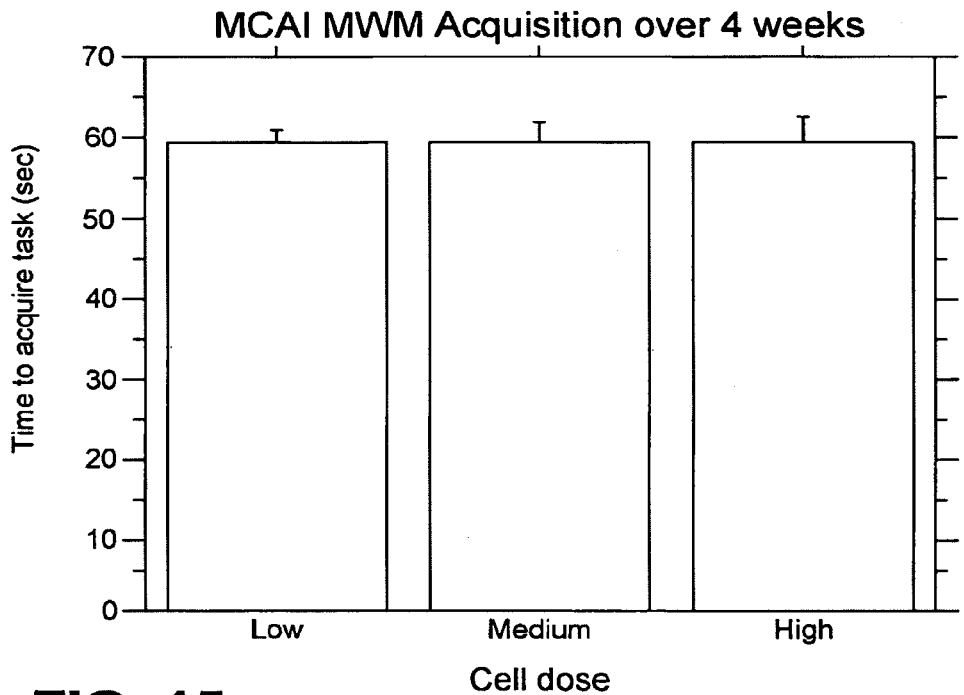
FIG. 15 shows results from the MCAI procedure.
Figure 16:
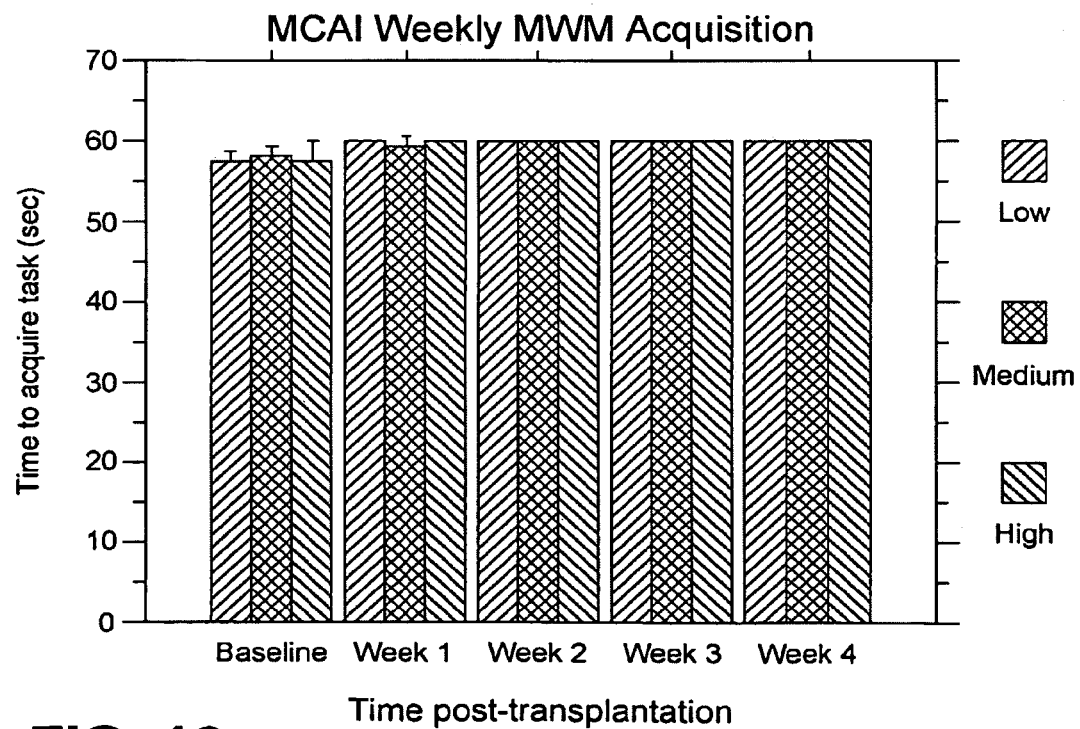
FIG. 16 shows results from the MCAI procedure.

MWM Acquisition: For the weekly testing over the four weeks post-transplantation, overall ANOVA revealed no significant main treatment effects ($F_{2,24}=5.78-16$, $p>0.05$) (FIG. 15). There appears to be a trend towards longer MWM acquisition time over the 4 weeks transplantation as revealed by longer acquisition times at 1, 2, 3 and 4 weeks post-transplantation compared to baseline (p's<0.0001) (FIG. 16).

Figure 17:
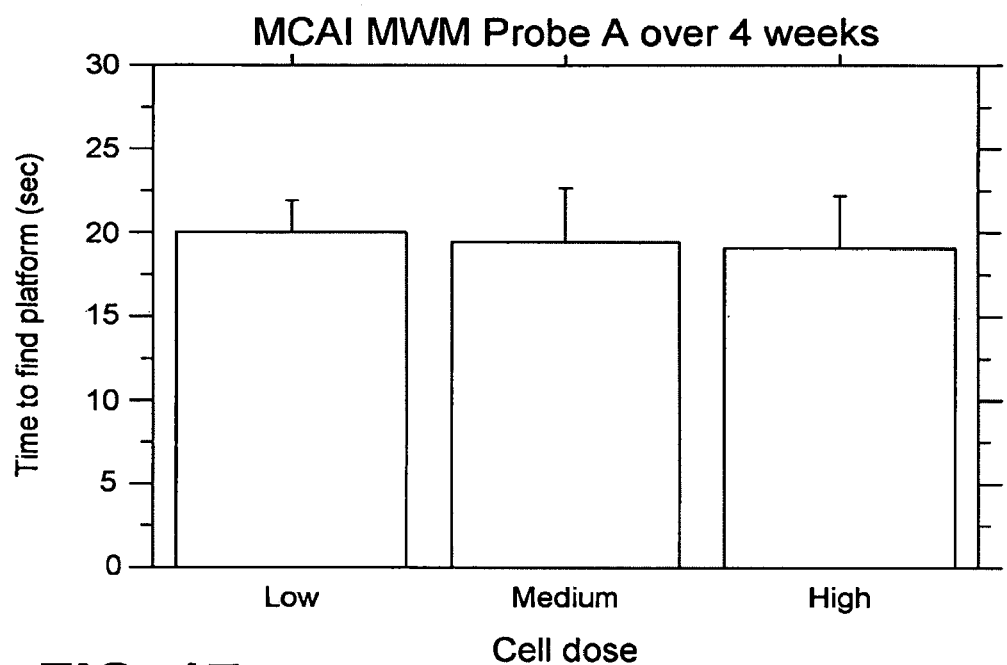
FIG. 17 shows results from the MCAI procedure.
Figure 18:
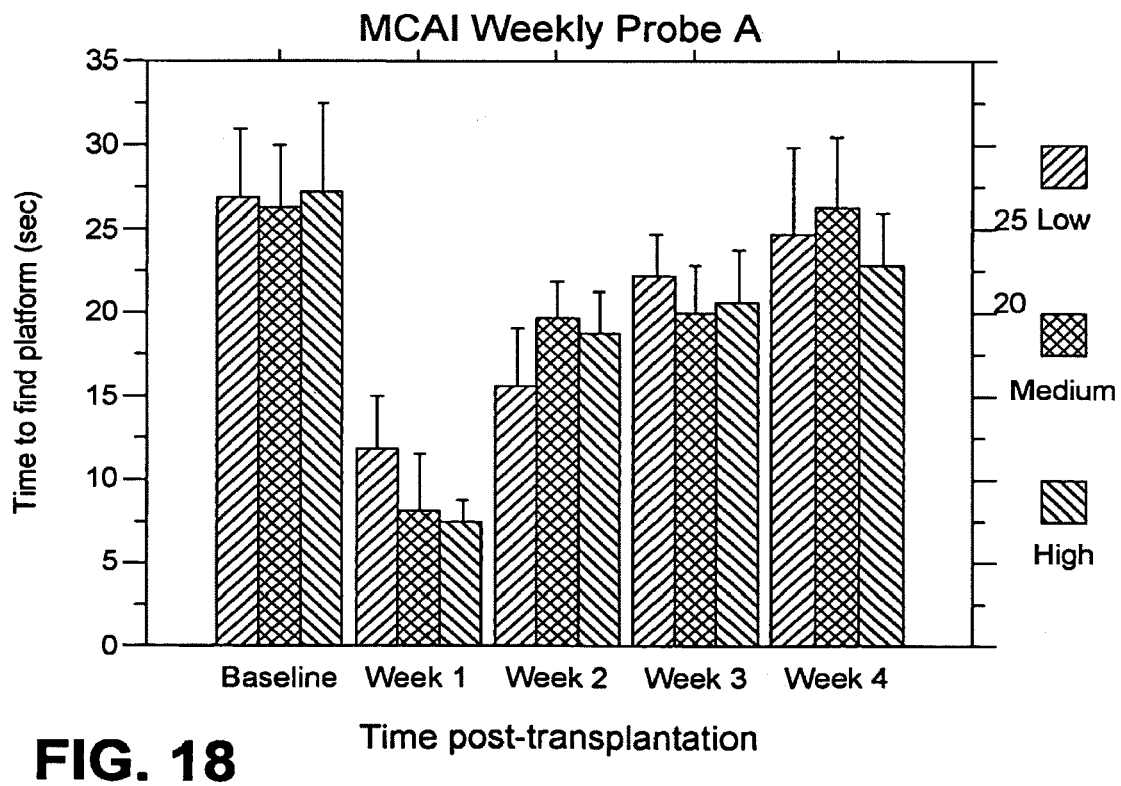
FIG. 18 shows results from the MCAI procedure.

MWM Probe test: Time to find the platform. For the weekly testing over the four weeks post-transplantation, overall ANOVA revealed no significant main treatment effects ($F_{2,24}=0.62$, $p=0.55$) (FIG. 17). Over time post-transplantation, significantly longer times in locating the platform were noted (p's<0.001) (FIG. 18).

Figure 19:
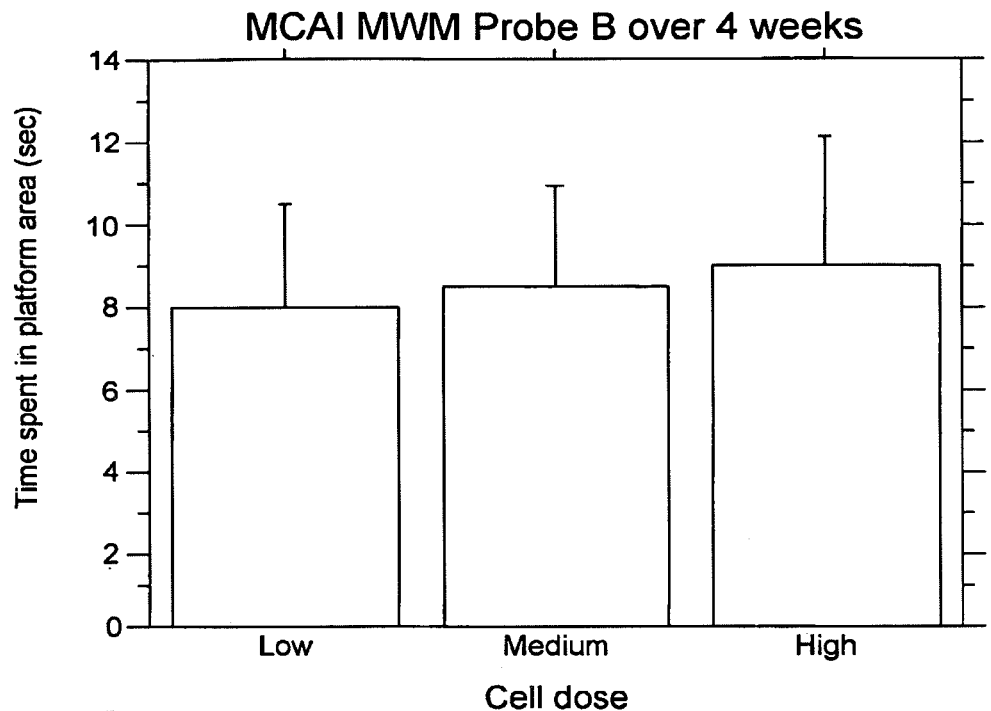
FIG. 19 shows results from the MCAI procedure.
Figure 20:
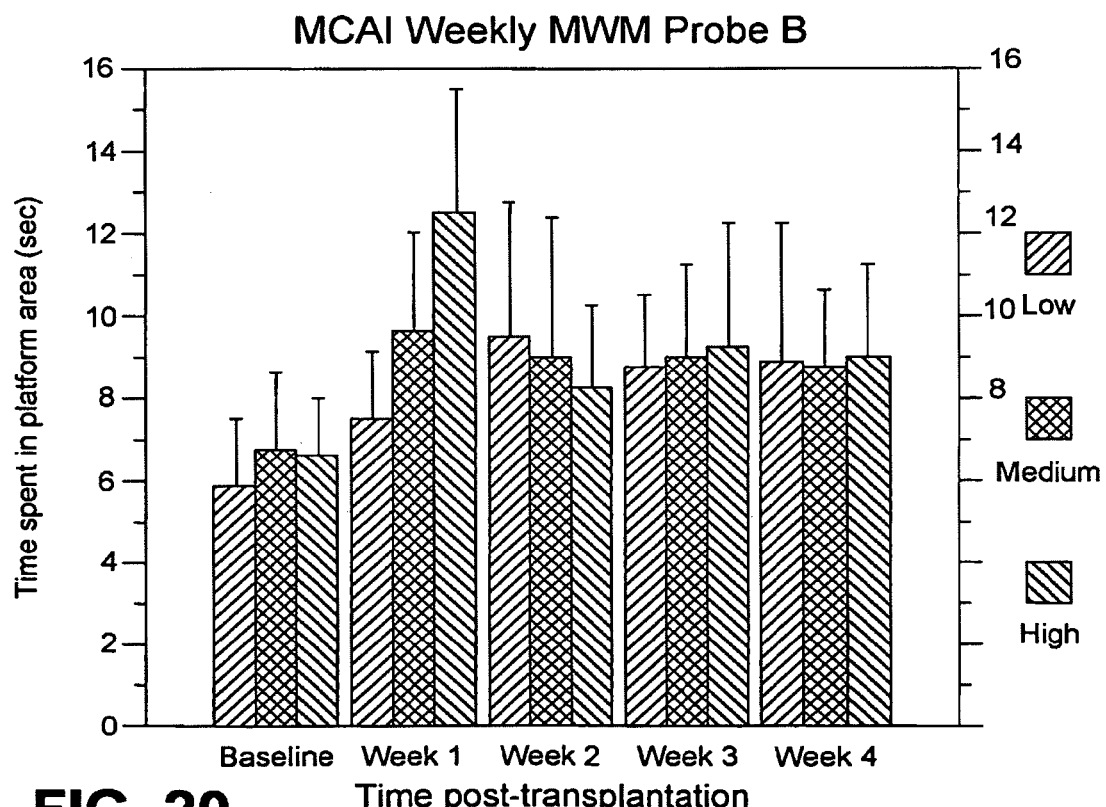
FIG. 20 shows results from the MCAI procedure.

MWM Probe test: Time spent on the platform area. For the weekly testing over the four weeks post-transplantation, overall ANOVA revealed no significant main treatment effects ($F_{2,24}=2.01$, $p=0.16$) (FIG. 19). Although a trend of longer times were spent in the platform area over the 4-week post-transplantation period compared to baseline (p's<0.001), transient dose-dependent effects were only seen at 1 week post-transplantation (p's<0.05), and not in the other weekly test time periods (p's >0.05) (FIG. 20).

Example 3

TGI Results—Weekly for Four Weeks
Post-Transplantation

The test animals underwent the TGI procedure as described above, and were evaluated weekly for four weeks port-transplantation with the following results.

Figure 21:
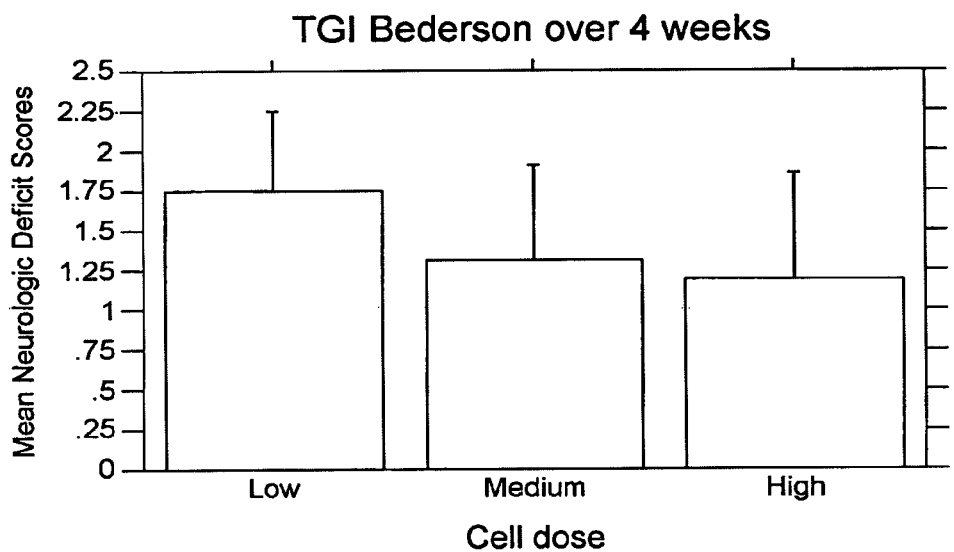
FIG. 21 shows results from the TGI procedure.
Figure 22:
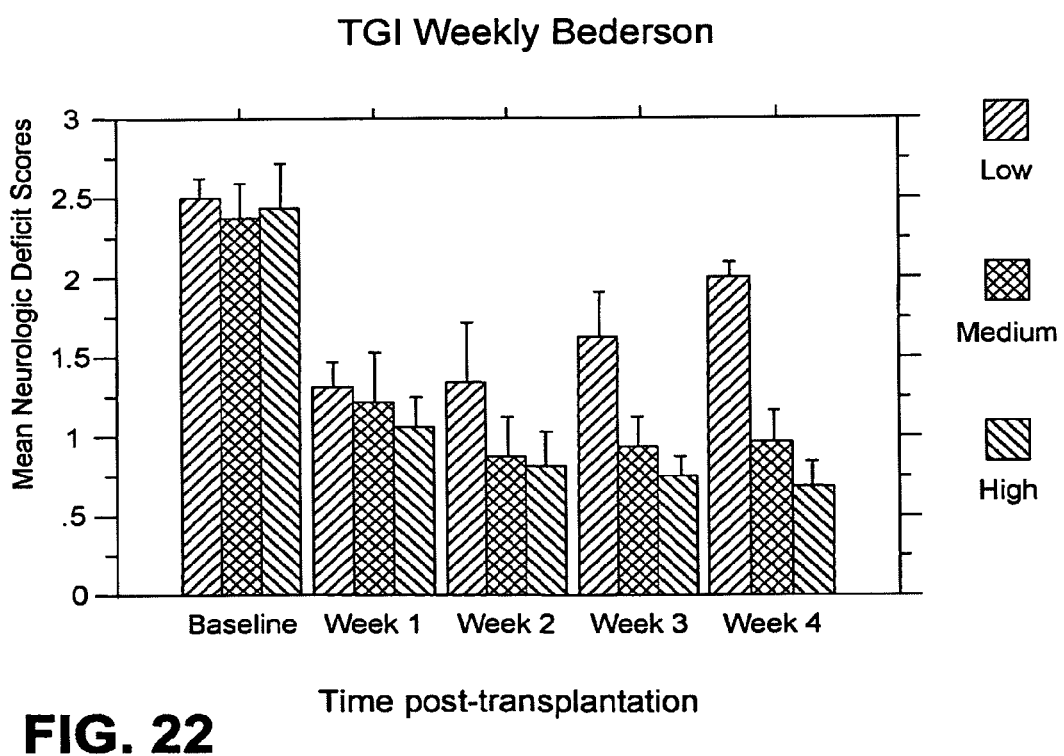
FIG. 22 shows results from the TGI procedure.

Bederson test: For the weekly testing over the four weeks post-transplantation, overall ANOVA revealed significant main treatment effects ($F_{2,23}=47.33$, $p<0.001$) (FIG. 21). The higher doses of 200,000 and 100,000 cells promoted better improvement in neurologic deficit scores than the low dose of 40,000 cells (p's<0.0001). Improvements in neurologic deficit scores were significantly reduced in each of the four weeks post-transplantation compared to baseline (p's<0.0001). Posthoc tests revealed that the significant reduction in neurologic deficit scores at 1 week post-transplantation did not differ across the three cell doses, but the high doses 100,000 and 200,000 produced better recovery than the low dose 40,000 cells at 2, 3 and 4 weeks (p's<0.005), and dose-dependent effects (200,000>100,000>40,000) were seen at 4 weeks post-transplantation (p's<0.05) (FIG. 22).

Figure 23:
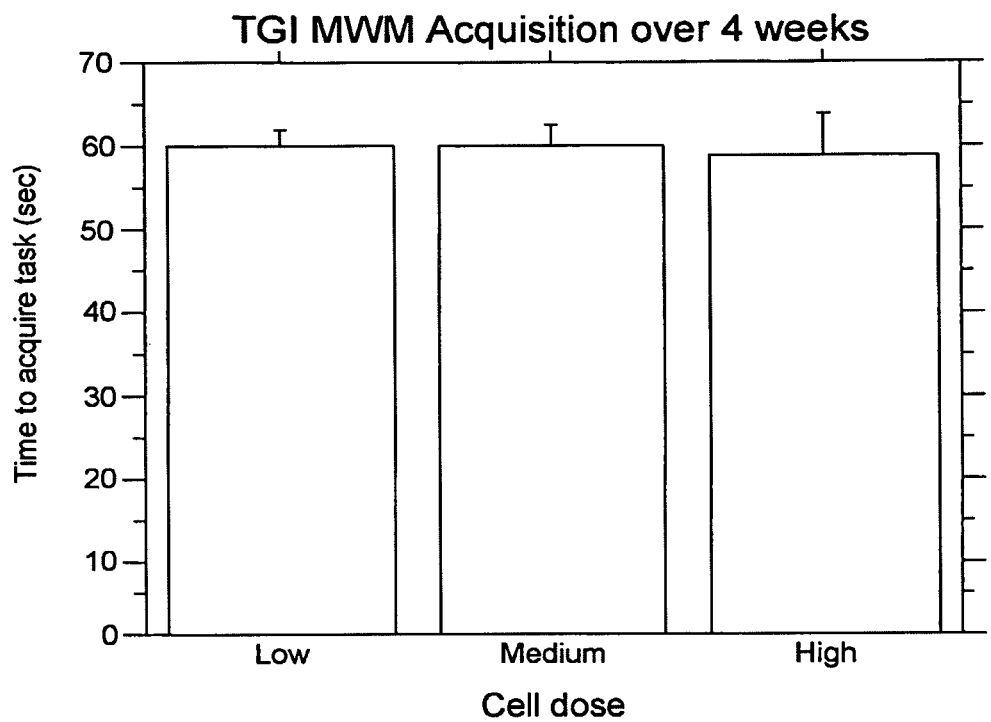
FIG. 23 shows results from the TGI procedure.
Figure 24:
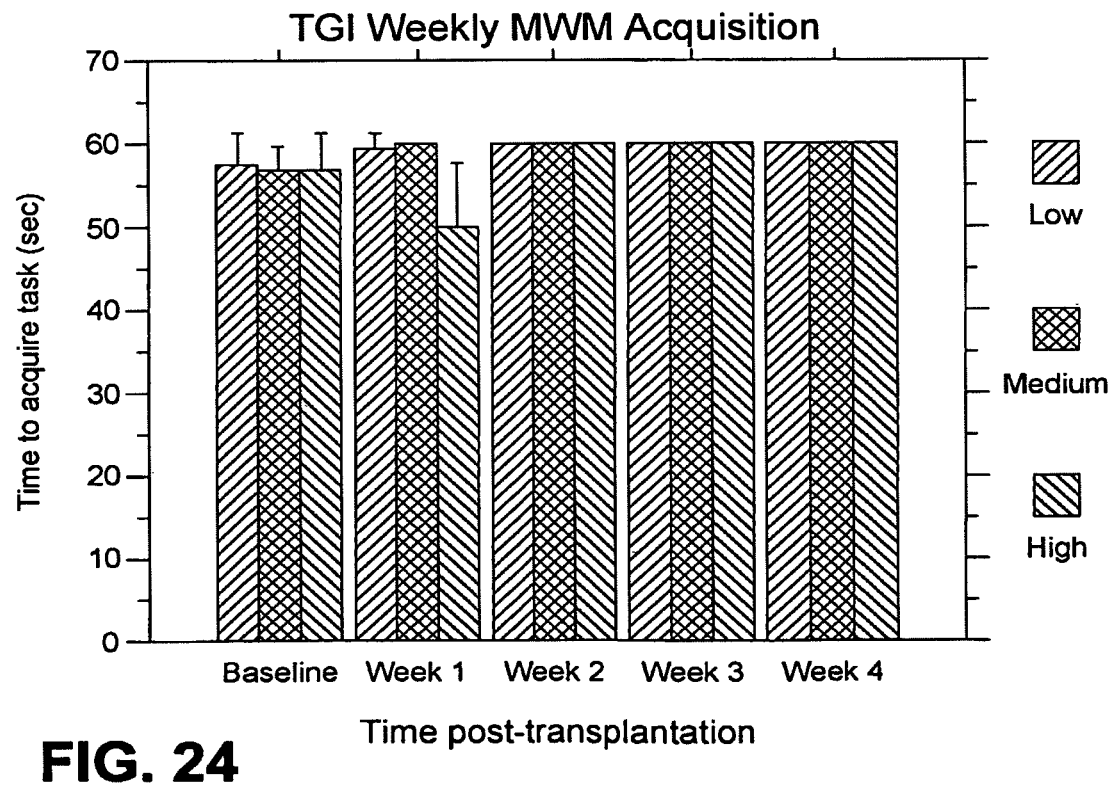
FIG. 24 shows results from the TGI procedure.

MWM Acquisition: For the weekly testing over the four weeks post-transplantation, overall ANOVA revealed significant main treatment effects ($F_{2,23}=9.88$, $p<0.001$) (FIG. 23). However, this significant treatment effect was achieved only because the highest dose of 200,000 cells produced a transient significant improvement in acquiring the task at 1 week post-transplantation compared to the two other doses of 100,000 and 40,000 cells (p's<0.005). Thereafter, longer acquisition times at 2, 3 and 4 weeks post-transplantation compared to baseline and 1 week post-transplantation were noted (p's<0.005) (FIG. 24).

Figure 25:
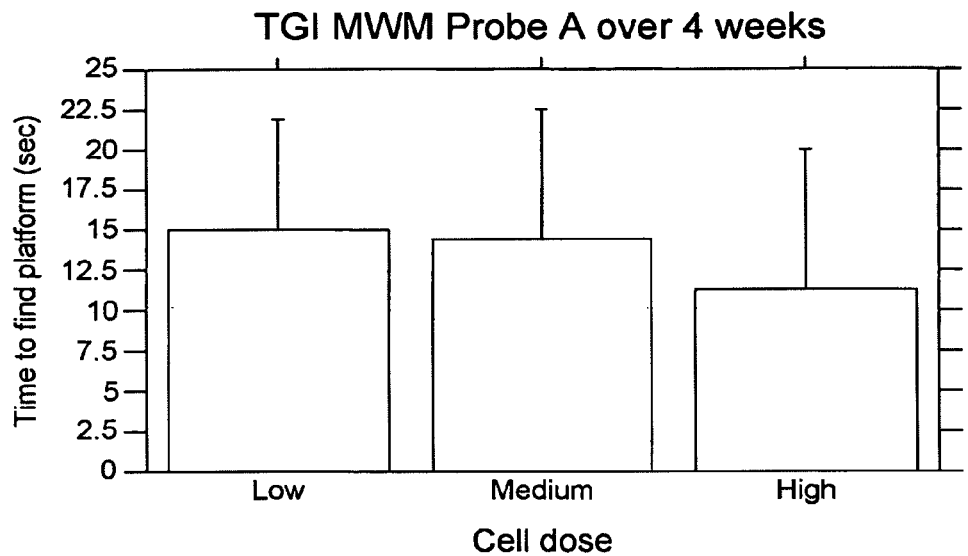
FIG. 25 shows results from the TGI procedure.
Figure 26:
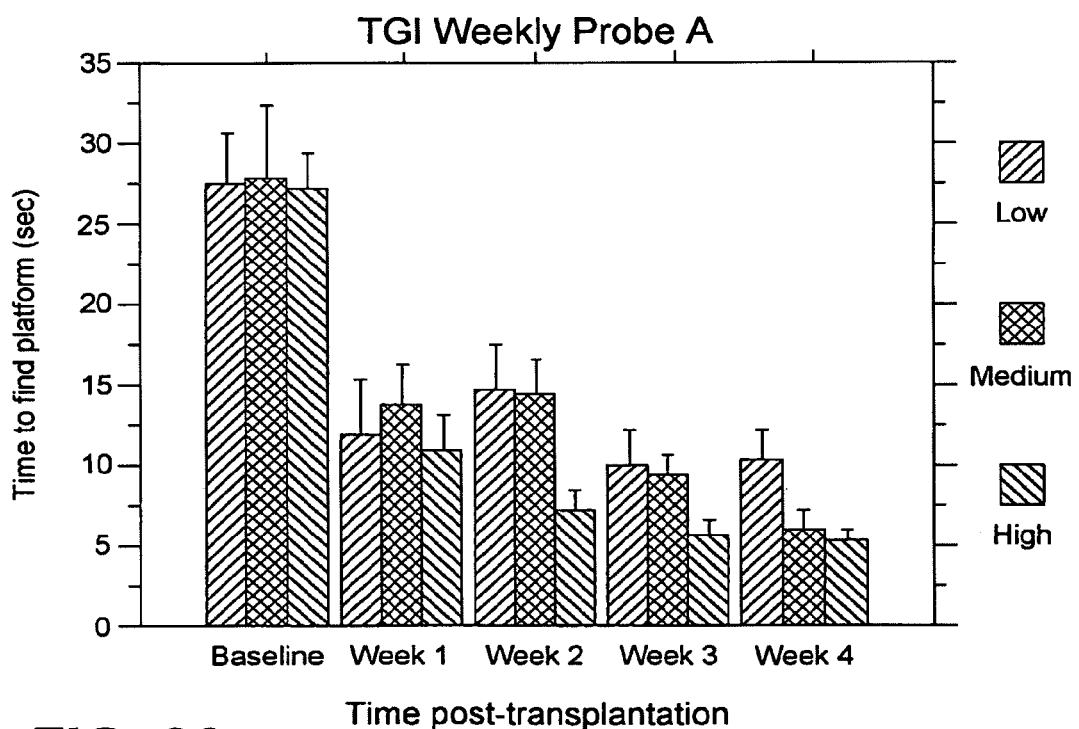
FIG. 26 shows results from the TGI procedure.

MWM Probe test: Time to find the platform. For the weekly testing over the four weeks post-transplantation, overall ANOVA revealed significant main treatment effects ($F_{2,23}=30.98$, $p<0.0001$) (FIG. 25). The higher doses of 200,000 and 100,000 cells promoted significantly shorter time locating the platform than the low dose of 40,000 cells (p's<0.0001). Improvements in the time to find the platform were significantly reduced in each of the four weeks post-transplantation compared to baseline (p's<0.0001), with a trend towards better improvement over time in that transplanted animals performed better at 3 and 4 weeks post-transplantation compared to 1 and 2 weeks post-transplantation (p's<0.0001). Posthoc tests revealed that the higher dose of 200,000 cells produced significantly shorter times to find the platform than the other two doses of 100,000 and 40,000 cells at 2 and 3 weeks post-transplantation period (p's<0.05), while the two higher doses exerted better improvement in finding the platform compared to the low cell dose at 4 weeks post-transplantation (p's<0.05) (FIG. 26).

Figure 27:
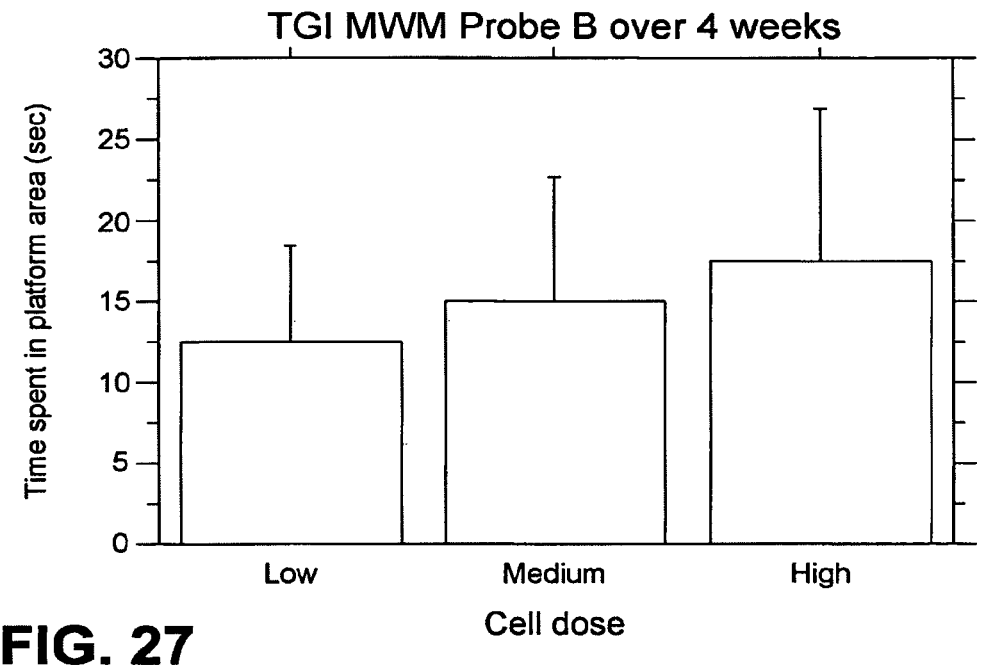
FIG. 27 shows results from the TGI procedure.
Figure 28:
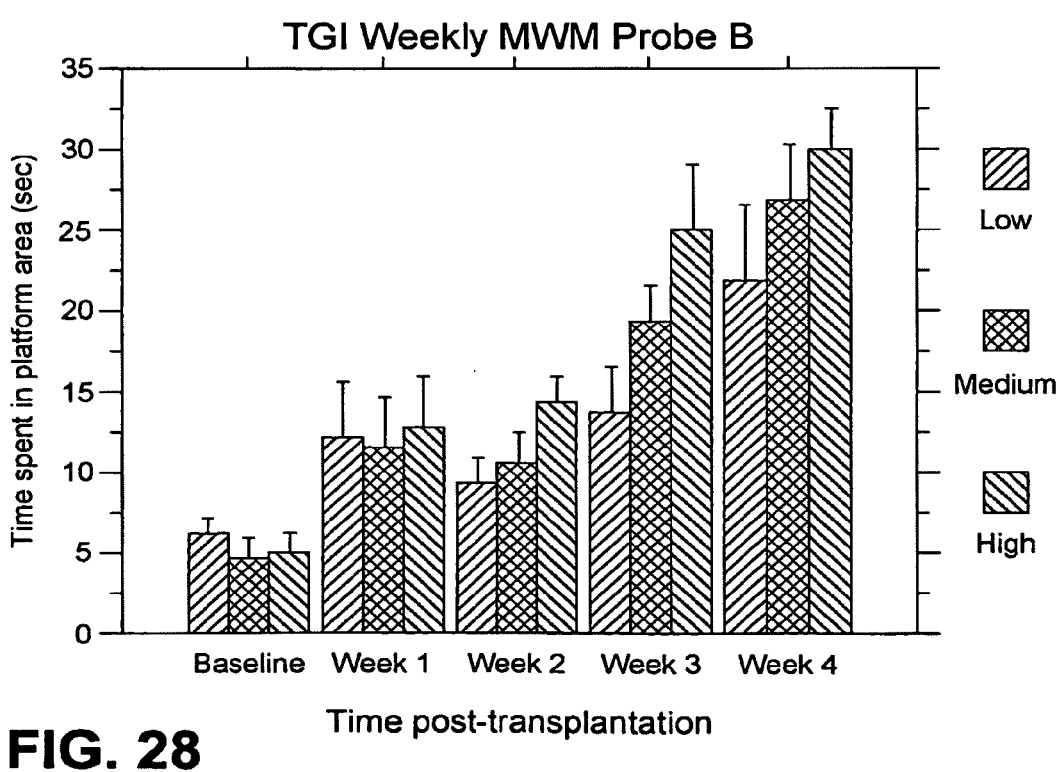
FIG. 28 shows results from the TGI procedure.

MWM Probe test: Time spent on the platform area. For the weekly testing over the four weeks post-transplantation, overall ANOVA revealed significant main treatment effects ($F_{2,23}=54.06$, $p<0.0001$) (FIG. 27). Significant dose-dependent effects (200,000>100,000>40,000) were seen over the 4-week post-transplantation period (p's<0.0001). In addition, over the 4-week post-transplantation period, longer times were spent in the platform area (p's<0.0001). Posthoc tests revealed that the higher doses of 200,000 and 100,000 produced significantly longer times spent in the platform area than the low dose 40,000 cells at 3 and 4 weeks post-transplantation period (p's<0.05). At 2 weeks post-transplantation, only the highest cell dose produced significantly longer time spent in the platform area compared to the other two cell doses (p's<0.05) (FIG. 28).

Example 4

Histological Examination at 5 Weeks Post-Transplantation

Randomly selected animals were euthanized at 5 weeks post-transplantation (see Table 3). Histological examinations were limited to 2-3 brain samples for each dose and stroke type. Accordingly, quantitative analyses could only be performed on graft survival and migration based on GFP epifluorescence. For the other histological parameters, specifically on using different antibody markers to detect phenotypic expression, only a general description is provided.

Figure 29:
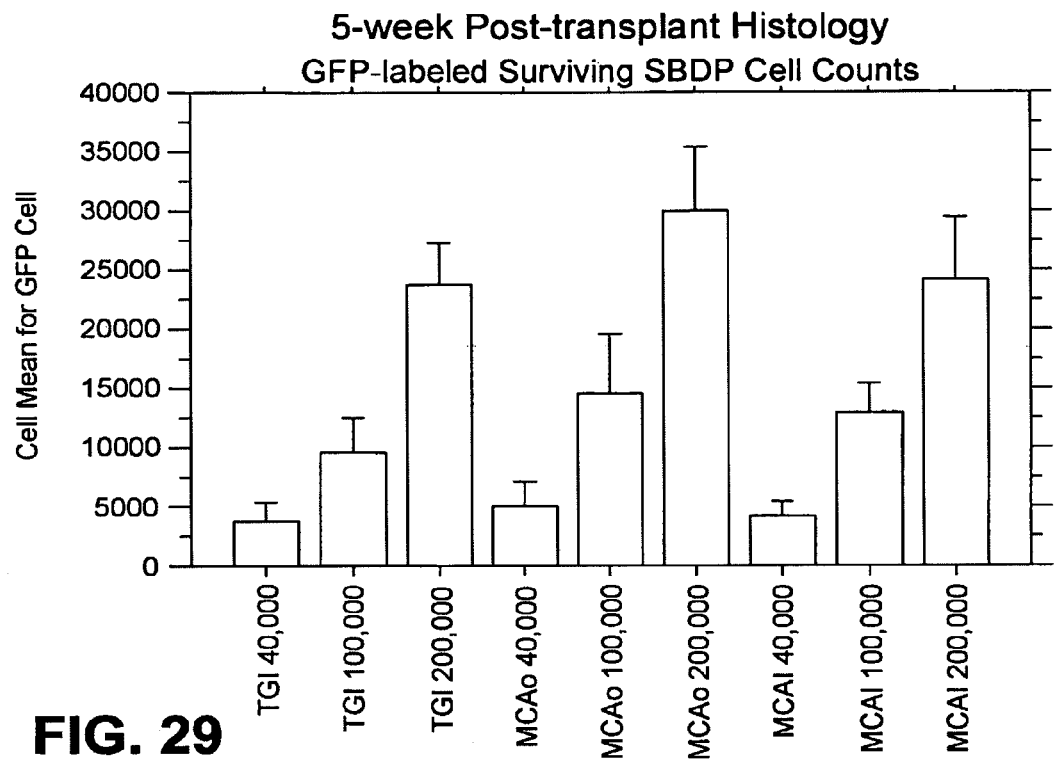
FIG. 29 shows histological results from the Examples.
Figure 30:
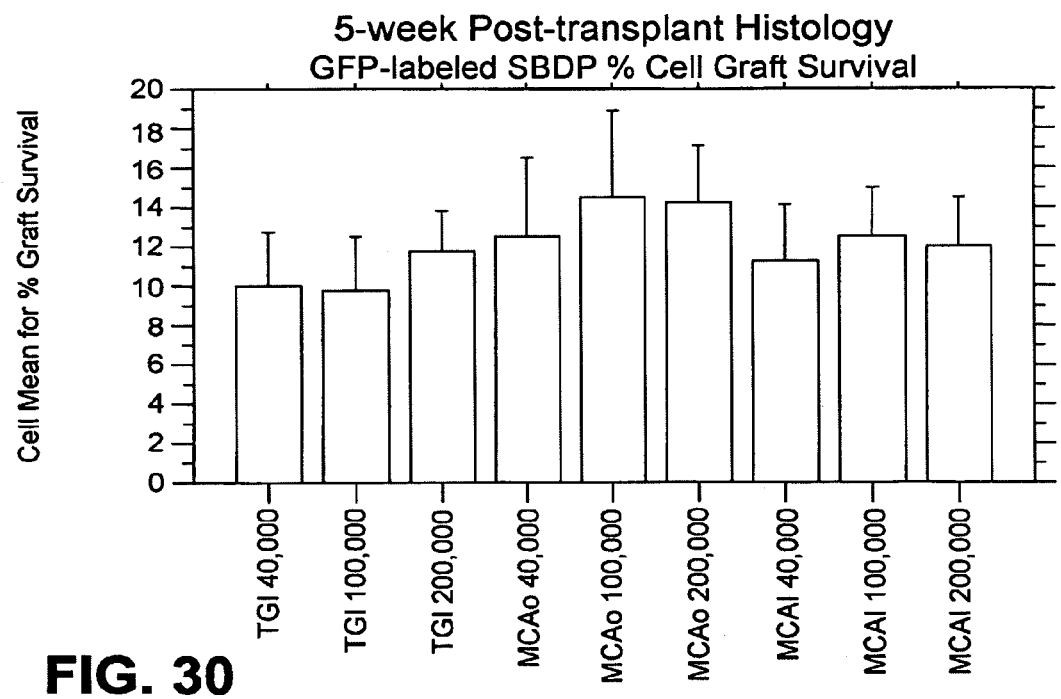
FIG. 30 shows histological results from the Examples.

NPC graft survival: GFP epifluorescence revealed dose-dependent graft survival (200,000>100,000>40,000) across all three stroke types (F8,32=33.9, p<0.0001) (FIG. 29). Mean cell counts of GFP-positive cells revealed that the lower dose of 40,000 cells resulted in low numbers of surviving GFP-positive grafts, while both higher doses of 100,000 and 200,000 resulted in higher numbers of surviving GFP-positive grafts. These observations were consistent for MCAo, MCAl and TGI transplanted animals. However, when percentages for each cell dose were calculated, no significant differences (F8,32=1.67, p>0.05) (FIG. 30) in the percent graft survival were obtained across the 3 doses.

TABLE 3

Five weeks post-transplant histology

| Graft type | Cell dose | Stroke Type | Sample size |
|---|---|---|---|
| NPC | 40,000 | MCAo | 4 |
|  |  | MCAl | 5 |
|  |  | TGI | 4 |
|  | 100,000 | MCAo | 5 |
|  |  | MCAl | 5 |
|  |  | TGI | 4 |
|  | 200,000 | MCAo | 5 |
|  |  | MCAl | 5 |
|  |  | TGI | 4 |

Figure 31:
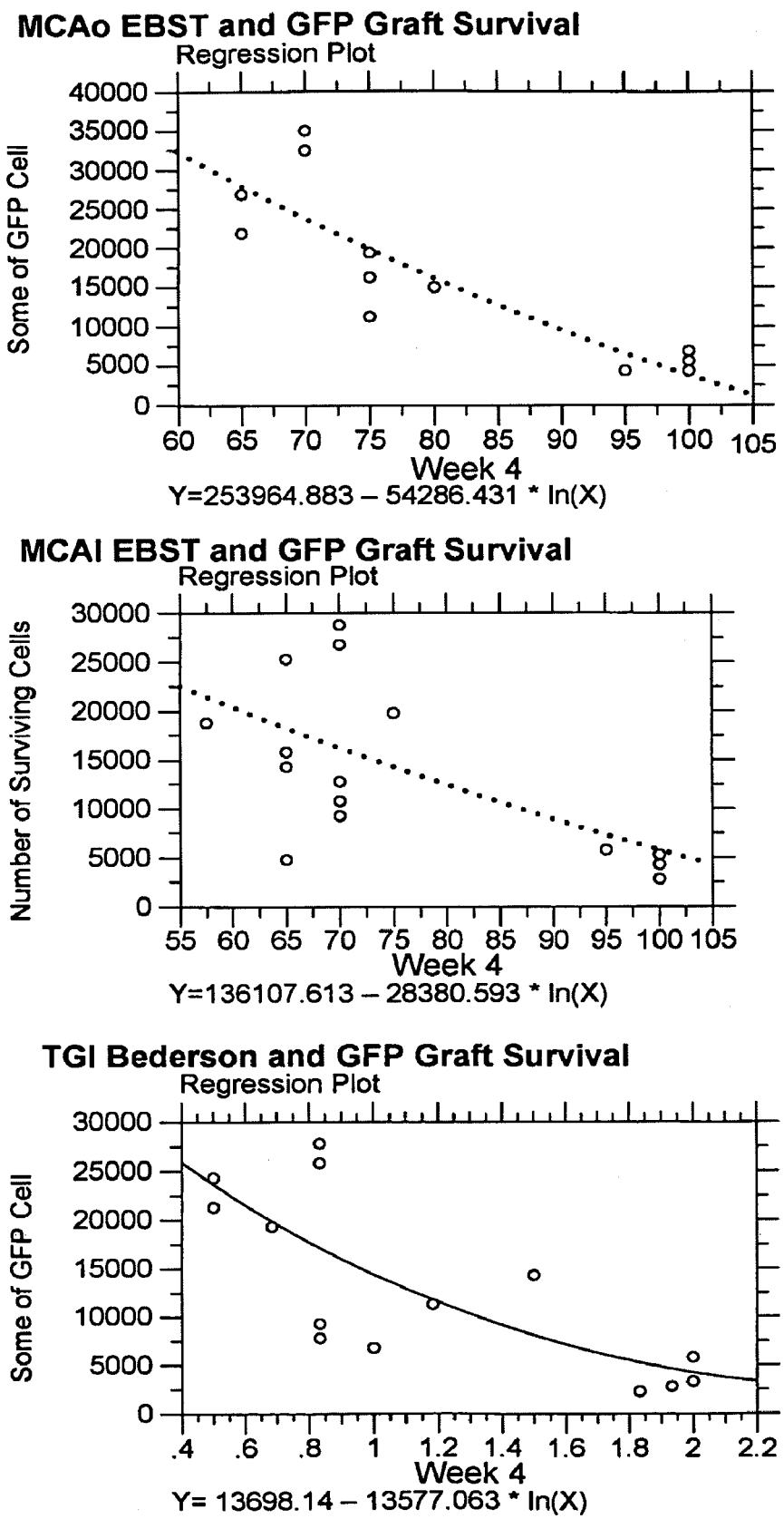
FIG. 31 illustrates functional recovery and graft survival.

Positive correlations between graft survival and functional recovery: Regression analyses revealed that the higher the number of surviving NPC grafts (200,000>100,000>40,000), the better the functional improvement (FIG. 31).

Figure 32:
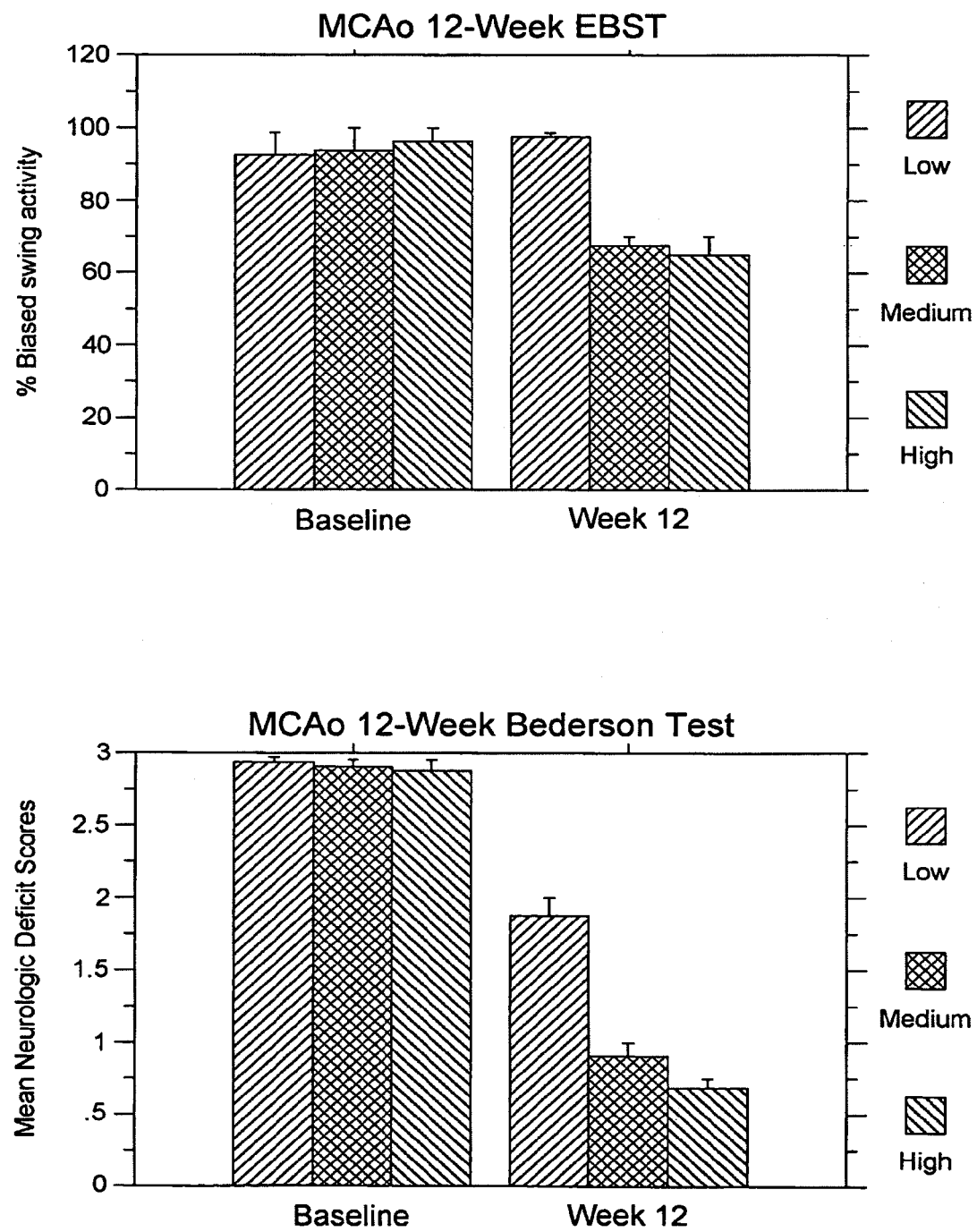
FIG. 32 shows results from the MCAo procedure.

NPC graft migration: GFP epifluorescence revealed that majority (approx. 55%-85%) of the transplanted cells remained within the original transplant site (FIG. 32). In MCAo transplanted animals, several GFP-positive cells could be easily identified within the original striatal transplant sites (62%); in MCAl transplanted animals, GFP-positive cells remained within the original cortical transplant sites (53%), and; in TGI transplanted animals, GFP-positive cells remained within the original hippocampal sites (86%). However, it appears that both MCAo and MCAl transplanted animals displayed more migration of grafted cells compared to TGI transplanted animals. Nonetheless, when migration was observed, the grafted cells remained within the general target area, in that graft migration in MCAo was observed within the striatum, in MCAl within the cortex, and in TGI within the hippocampus. Graft migration in both MCAo and MCAl was characterized by grafted cells lining the ischemic penumbra in the striatum and cortex, respectively. Furthermore for MCAo, a medial to lateral (1.8 mm) and dorsal to ventral (2.3 mm) migration of cells along the striatal ischemic penumbra was observed. For MCAl, a medial to lateral (4.4 mm) migration of cells was seen. For TGI transplanted animals, graft migration was characterized by GFP-positive SBDPs identified in the CA2 and CA3 regions (1.6 mm and 0.7 mm away, respectively, from the original CA1 transplant site).

NPC phenotypic expression: Grafted NPC cells were positive for GFAP (about 5%) and a very few cells (2-5 cells per brain) were also positive for NeuN. Both these markers co-localized with GFP. These observations were consistent for all doses and all three types of stroke.

Example 5

MCAo Results at Twelve Weeks Post-Transplantation

At twelve weeks following transplantation, the test animals that underwent the TGI procedure as described above were evaluated with the following results.

EBST: For the 12 weeks post-transplantation testing, overall ANOVA revealed significant main treatment effects (F2, 9=11.84, p<0.005) (FIG. 32). Posthoc test revealed significantly reduced motor asymmetry at 12 weeks post-transplantation compared to baseline (p<0.001).

Bederson test: For the 12 weeks post-transplantation testing, overall ANOVA revealed significant main treatment effects (F2,9=41.83, p<0.001) (FIG. 32). Posthoc testing revealed significantly reduced neurological deficits at 12 weeks post-transplantation compared to baseline (p<0.001).

Figure 33:
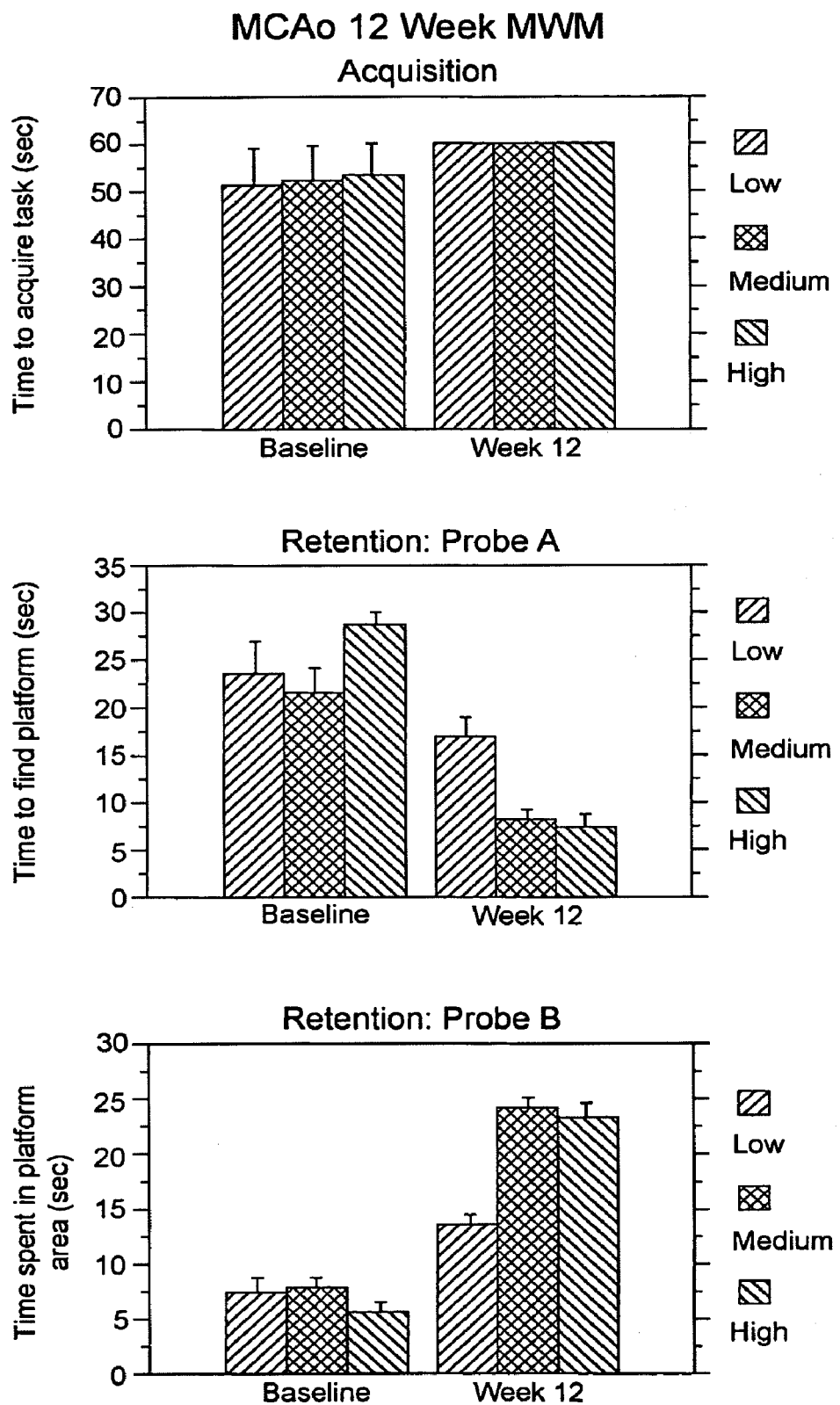
FIG. 33 shows results from the MCAo procedure.

MWM Acquisition: For the 12 weeks post-transplantation testing, overall ANOVA revealed no significant main treatment effects (F2,9=0.36, p=0.71) (FIG. 33). These results indicate no significant differences in MWM acquisition between baseline and 12 week post-transplantation.

MWM Probe test: Time to find the platform. For the 12 weeks post-transplantation testing, overall ANOVA revealed significant main treatment effects (F2,9=6.18, p<0.05) (FIG. 33). Posthoc test revealed significantly reduced time to find the platform at 12 weeks post-transplantation compared to baseline (p<0.001).

MWM Probe test: Time spent on the platform area. For the 12 weeks post-transplantation testing, overall ANOVA revealed significant main treatment effects (F2,9=6.18, p<0.05) (FIG. 33). Posthoc test revealed significantly increased time in the platform area at 12 weeks post-transplantation compared to baseline (p<0.001).

Example 6

MCAI Results at Twelve Weeks Post-Transplantation

At twelve weeks following transplantation, the test animals that underwent the MCAI procedure as described above were evaluated with the following results.

Figure 34:
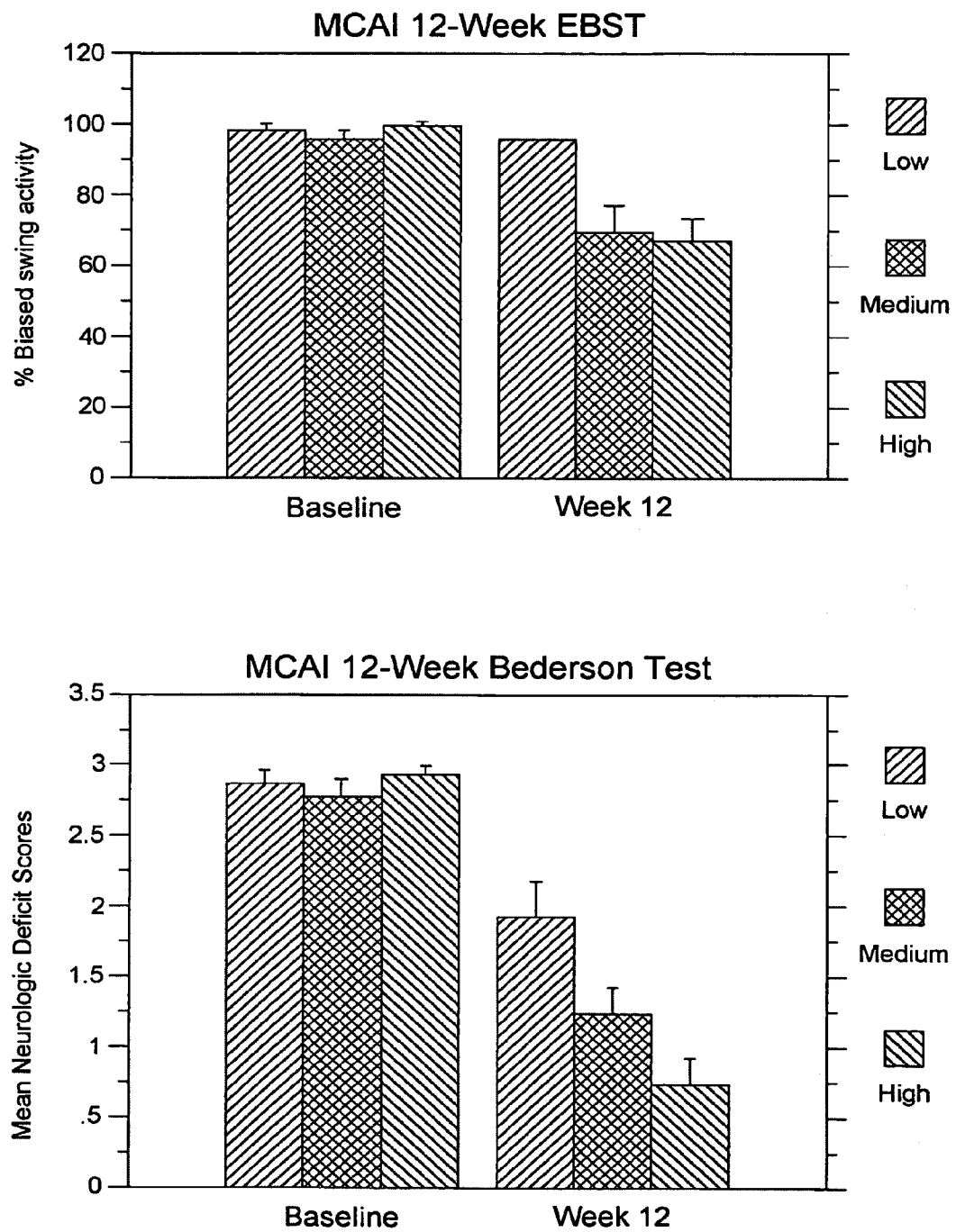
FIG. 34 shows results from the MCAI procedure.

EBST: For the 12 weeks post-transplantation testing, overall ANOVA revealed significant main treatment effects (F2, 9=23.02, p<0.0005) (FIG. 34). Posthoc test revealed significantly reduced motor asymmetry at 12 weeks post-transplantation compared to baseline (p<0.0001).

Bederson test: For the 12 weeks post-transplantation testing, overall ANOVA revealed significant main treatment effects (F2,9=9.29, p<0.01) (FIG. 34). Posthoc test revealed significantly reduced neurological deficits at 12 weeks post-transplantation compared to baseline (p<0.0001).

Figure 35:
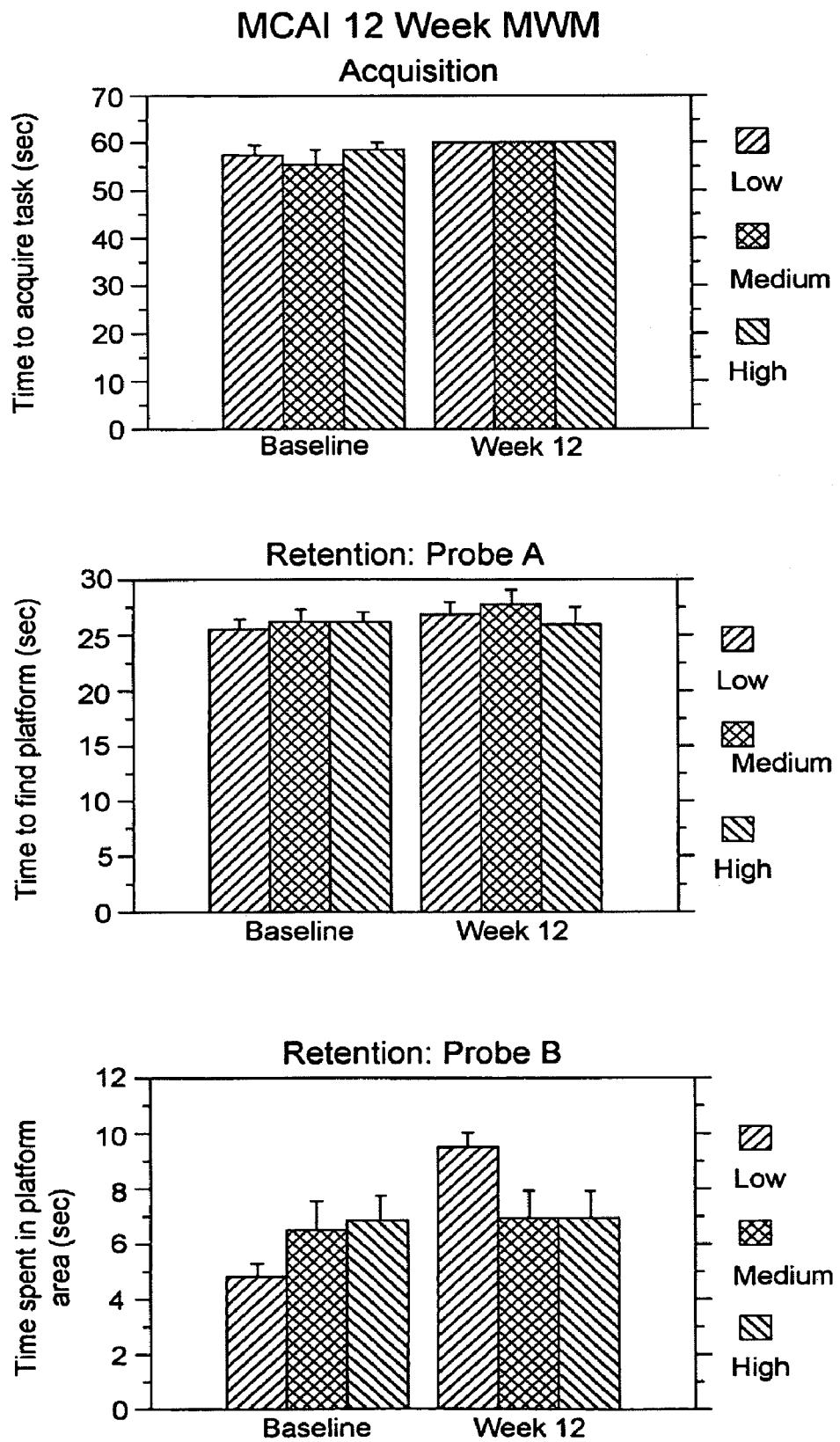
FIG. 35 shows results from the MCAI procedure.

MWM Acquisition: For the 12 weeks post-transplantation testing, overall ANOVA revealed no significant main treatment effects (F2,9=1.37, p=0.30) (FIG. 35). These results indicate no significant differences in MWM acquisition between baseline and 12 week post-transplantation.

MWM Probe test: Time to find the platform. For the 12 weeks post-transplantation testing, overall ANOVA revealed no significant main treatment effects (F2,9=0.26, p=0.78) (FIG. 35). These results indicate no significant differences in MWM probe test, i.e., with the platform available, between baseline and 12 week post-transplantation.

MWM Probe test: Time spent on the platform area. For the 12 weeks post-transplantation testing, overall ANOVA revealed no significant main treatment effects (F2,9=0.15, p=0.86) (FIG. 35). These results indicate no significant differences in MWM probe test, i.e., without the platform, between baseline and 12 week post-transplantation.

Example 7

TGI Results at Twelve Weeks Post-Transplantation

At twelve weeks following transplantation, the test animals that underwent the TGI procedure as described above were evaluated with the following results.

Figure 36:
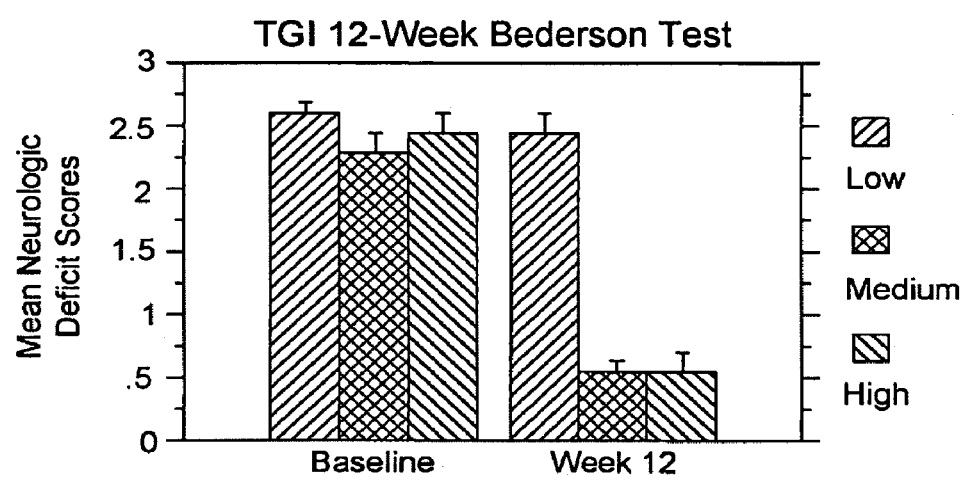
FIG. 36 shows results from the TGI procedure.

Bederson test: For the 12 weeks post-transplantation testing, overall ANOVA revealed significant main treatment effects (F2,9=184.02, p<0.0001) (FIG. 36). Posthoc test revealed significantly reduced neurological deficits at 12 weeks post-transplantation compared to baseline (p<0.0001).

Figure 37:
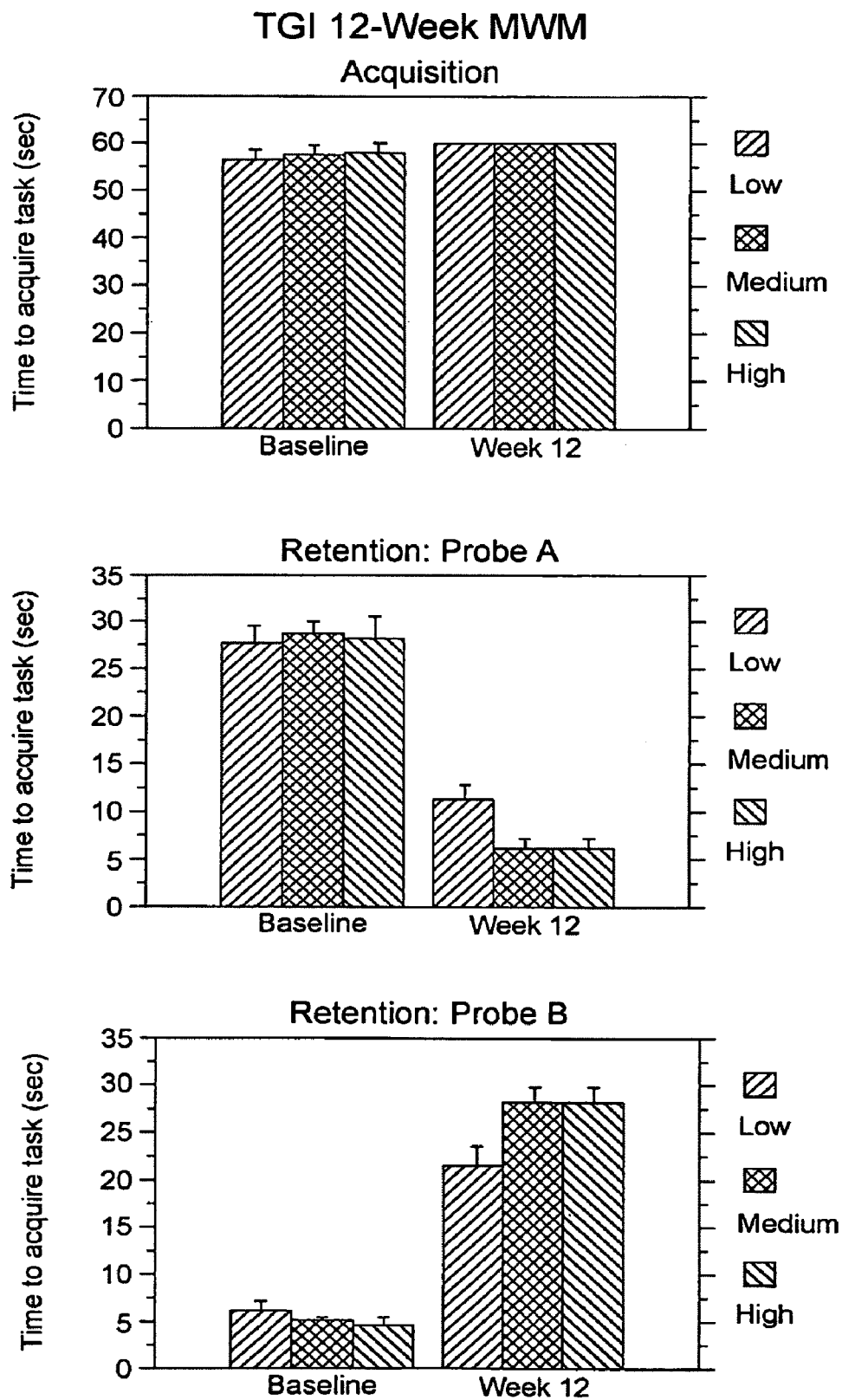
FIG. 37 shows results from the TGI procedure.

MWM Acquisition: For the 12 weeks post-transplantation testing, overall ANOVA revealed no significant main treatment effects (F2,9=0.31, p=0.74) (FIG. 37). These results indicate no significant differences in MWM acquisition between baseline and 12 week post-transplantation.

MWM Probe test: Time to find the platform. For the 12 weeks post-transplantation testing, overall ANOVA revealed significant main treatment effects (F2,9=5.14, p<0.05) (FIG. 37). Posthoc test revealed significantly reduced time to find the platform at 12 weeks post-transplantation compared to baseline (p<0.0001).

MWM Probe test: Time spent on the platform area. For the 12 weeks post-transplantation testing, overall ANOVA revealed significant main treatment effects (F2,9=4.39, p<0.05) (FIG. 37). Posthoc test revealed significantly increased time in the platform area at 12 weeks post-transplantation compared to baseline (p<0.0001).

Example 8

Histological Examination at 12 Weeks Post-Transplantation

All remaining animals were euthanized at 12 weeks post-transplantation (see Table 4). Quantitative analyses of graft survival and migration based on GFP epifluorescence and other immunohistochemical parameters, specifically on using different antibody markers to detect phenotypic expression, were conducted.

TABLE 4

Twelve weeks post-transplant histology

| Graft type (Approx.) | Cell dose | Stroke Type | Sample size |
|---|---|---|---|
| NPC | 40,000 | MCAo | 4 |
| | | MCAl | 4 |
| | | TGI | 4 |
| | 100,000 | MCAo | 4 |
| | | MCAl | 4 |
| | | TGI | 4 |
| | 200,000 | MCAo | 4 |
| | | MCAl | 4 |
| | | TGI | 4 |

Figure 38:
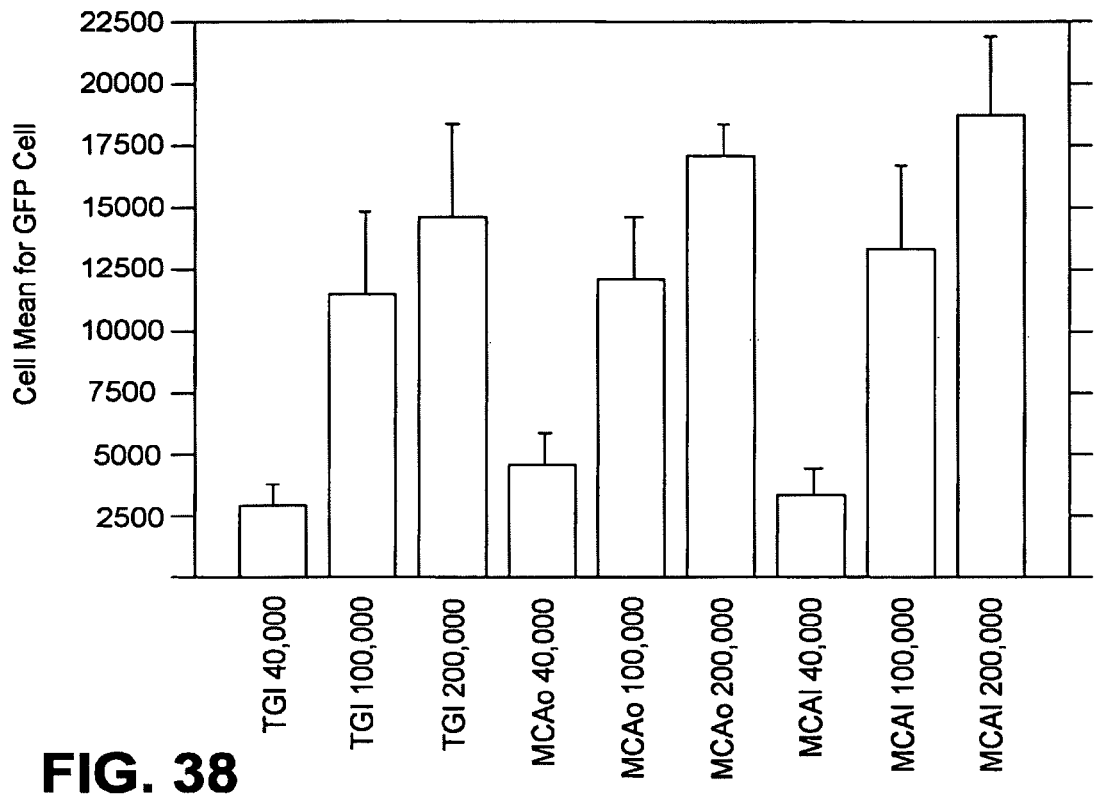
FIG. 38 illustrates graft survival.
Figure 39:
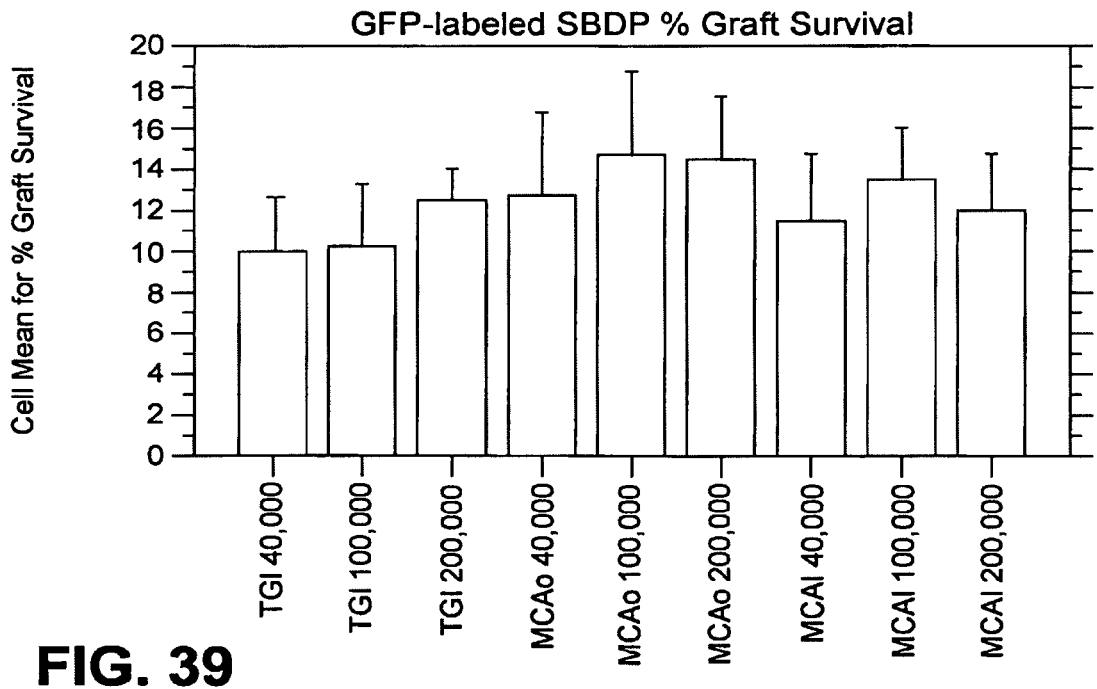
FIG. 39 illustrates graft survival.

NPC graft survival: GFP epifluorescence revealed partial dose-dependent graft survival (200,000=100,000>40,000) across all three stroke types (F8,27=14.88, p<0.0001) (FIG. 38). Mean cell counts of GFP-positive cells revealed that the lower dose of 40,000 cells resulted in low numbers of surviving GFP-positive grafts, while both higher doses of 100,000 and 200,000 resulted in higher numbers of surviving GFP-positive grafts. These observations were consistent for MCAo, MCAI and TGI transplanted animals. However, when percentages for each cell dose were calculated, no significant differences (F8,27=1.37, p>0.05) (FIG. 39) in the percent graft survival were obtained across the 3 doses. This suggests that percent graft survival in both low and high doses was maintained, potentially by CsA immunosuppression.

NPC graft migration: In agreement with the 5-week histology results, GFP epifluorescence revealed that majority (approx. 65%-90%) of the transplanted cells remained within the original transplant site. In MCAo transplanted animals, several GFP-positive cells could be easily identified within the original striatal transplant sites (72%); in MCAI transplanted animals, GFP-positive cells remained within the original cortical transplant sites (64%), and; in TGI transplanted animals, GFP-positive cells remained within the original hippocampal sites (91%). It appears that both MCAo and MCAI transplanted animals displayed more migration of grafted cells compared to TGI transplanted animals. Moreover, when migration was observed, the grafted cells remained within the general target area, in that graft migration in MCAo was observed within the striatum, in MCAI within the cortex, and in TGI within the hippocampus. In addition, graft migration in both MCAo and MCAI was characterized by grafted cells lining the ischemic penumbra in the striatum and cortex, respectively. Furthermore for MCAo, a medial to lateral (2.0 mm) and dorsal to ventral (2.5 mm) migration of cells along the striatal ischemic penumbra was observed. For MCAI, a medial to lateral (4.5 mm) migration of cells was seen. For TGI transplanted animals, graft migration was characterized by GFP-positive SBDPs identified in the CA2 and CA3 regions (1.6 mm and 0.8 mm away, respectively, from the original CA1 transplant site).

NPC phenotypic expression: Across stroke types and doses, the approximate survival rate is 15%. Within these original transplant sites, most of the cells retain their beady appearance, and are not positive for NeuN or GFAP. However, in MCAo transplanted animals, a few of these cells exhibit NeuN and GFAP. GFP positive cells were detected that migrated along the striatal penumbra, cortical penumbra and CA3 of MCAo, MCAI, and TGI transplanted animals, respectively. Indeed, NeuN immunostaining reveals that these cells express such marker for mature neurons. Overall, about 25% of surviving GFP positive cells are NeuN positive across stroke types and doses; in cells that have migrated away from the transplant site, about 60% are NeuN positive. These cells displayed neuronal morphology, characterized by elaborate and long processes, which are abundant in MCAo transplanted animals. Further GFP epifluorescence microscopy revealed the distinct neuronal morphology found in each stroke type, as well as NPC graft cell-to-cell contact. Some cells (about 5% overall and across stroke types and doses) exhibit the morphology of glial cell which was confirmed by GFAP staining. Most, if not all, GFAP positive cells were found near or within blood vessels.

Graft-host tissue pathology: There was no evidence of tumor formation using Nissl staining in striatum; cortex; or hippocampus.

Example 9

Additional NPC Testing in Stroke Models

The purpose of this study was to examine the therapeutic benefits of NPCs in stroke animals. Behavioral tests were used to reveal motor and neurological functions of transplanted stroke animals. Transplantation was carried out at 1 month post-stroke, and animals were immunosuppressed daily with Cyclosporin-A (CsA, 10 mg/kg, i.p.) throughout the one-month post-transplantation survival time. Locomotor and neurological performance of transplanted rats were characterized at days 7, 14 and 28 post-transplantation. Successful transplant outcome, as revealed by determination of an efficacious NPC dose range, was evaluated using locomotor behavior and neurological performance.

There were 3 treatment conditions: 0 (medium alone), low dose 90 k NPC, and high dose 180 k NPC. The number of animals for each treatment condition corresponded to a required sample size for statistical analyses (n=10 per group). Animals not reaching the criteria for behavioral deficits (75% biased swing activity and a score of 2.5 in neurological exam) were not included in the study. Thus, animals that reached these criteria and those exceeding these criteria were included in the study. Typically, most stroke animals reached such criteria, with at least 8 subjects needed to provide conclusive statistical analyses. All animals were immunosuppressed (10 mg/kg CsA, i.p., daily) throughout the study.

All animals initially received MCAo stroke surgery. At four weeks after the surgery, animals were tested with the EBST, followed an hour later by the Bederson neurological exam. Only animals that displayed significant motor and neurological deficits were subsequently used for transplantation surgery and randomly assigned to one of the following treatments:

TABLE 5

TREATMENT CONDITIONS

| GRAFT TYPE | CELL DOSE | STROKE TYPE | SAMPLE SIZE |
|---|---|---|---|
| NPC | 90,000 | MCAo | 10 |
| NPC | 180,000 | MCAo | 10 |
| Vehicle | 0 | MCAo | 10 |

Legend:
All animals underwent stroke surgery, received striatal (MCAo) transplants, and were treated with chronic CsA.

Animals were again introduced to the same battery of behavioral tests at days 7, 14 and 28 post-transplantation. For clarity, a schematic diagram is provided below.

TABLE 6

TIMELINE OF EXPERIMENTAL PROCEDURES

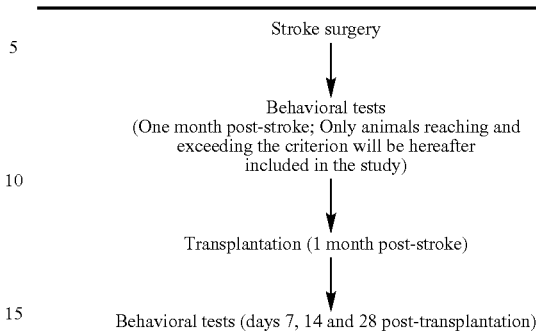

All surgical procedures were conducted under aseptic conditions. The animals were anesthetized with equithesin (300 mg/kg, i.p.) and checked for pain reflexes. Under deep anesthesia, animals underwent the MCA occlusion surgery. The MCA occlusion technique involves insertion of a suture filament through the carotid artery to reach the junction of the MCA, thus blocking the blood flow from the common carotid artery, as well as from the circle of Willis. The right common carotid artery was identified and isolated through a ventral midline cervical incision. The filament size was 4-0, made of sterile, non-absorbable suture (Ethicon, Inc.), with the diameter of the suture tip tapered to 24 to 26-gauge size using a rubber cement. About 15 to 17 mm of the suture filament was inserted from the junction of the external and internal carotid arteries to block the MCA. The right MCA was occluded for one hour; a one-hour occlusion of the MCA generally results in maximal infarction. In addition, the length and size of the tip of the embolus have been found to produce complete MCA occlusion in animals weighing between 250 to 350 g. A heating pad and a rectal thermometer promotes maintenance of body temperature within normal limits. To determine successful occlusion and reperfusion, a Laser Doppler was used. The Doppler probe was placed at the level of the dura directly above the expected infarct striatal region (AP: +2.0, ML: ±2.0, and DV: −4.0 mm) to measure cerebral blood flow before, during and after occlusion.

All surgical procedures were conducted under aseptic conditions. Under equithesin (3 ml/kg i.p.) anesthesia (animals checked for pain reflexes), the animals were implanted with NPCs or vehicle directly into the striatum (0.5 mm anterior to bregma, 2.8 mm lateral to midline and 5.0 mm below the dural surface) using a 28-gauge implantation cannula. Cryopreserved human NPCs were obtained from SanBio, Inc. and thawed just prior to transplantation surgery. Viability cell counts, using Trypan Blue exclusion method, were conducted prior to transplantation and immediately after the transplantation on the last animal recipient. The pre-determined cell dosages (90,000 and 180,000) were based on pilot studies demonstrating that these dosages are within therapeutically effective dosage range.

Transplantation surgery was carried out within 2 hours after thawing the cells. Infusion rate was 1 ul of cell solution per minute. Following infusion, a 3-minute absorption period was allowed before the needle was retracted. One needle pass was used, but there were 3 dorsoventral deposits, with each site receiving a 3-ul cell solution. A heating pad and a rectal thermometer allowed maintenance of body temperature at about 37° C. throughout surgery and following recovery from anesthesia.

The one-hour MCAo stroke surgery produced consistent behavioral impairments at one month post-stroke as revealed by significant biased swing activity and neurological deficits in EBST and Bederson exam, respectively, compared to pre-stroke performance of the animals in both tests. Pair-wise comparisons between pre-stroke and post-stroke performance of the animals revealed significant impairments in both tests (p's<0.0001) in all stroke animals included in this study.

Figure 44:
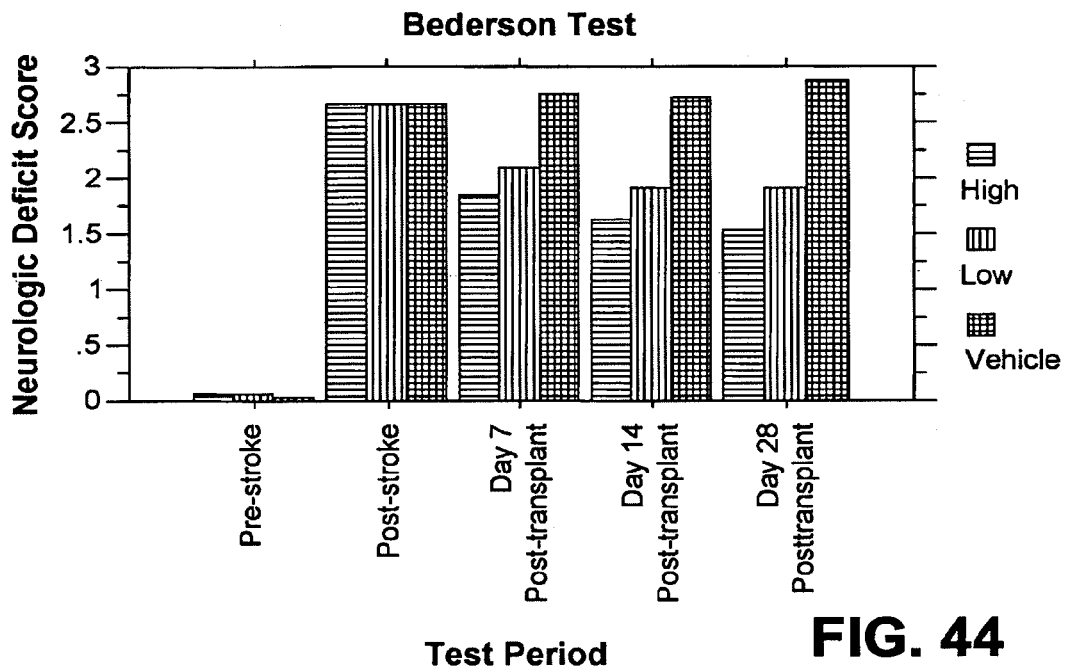
FIG. 44 shows results from Bederson testing performed in Example 9.
Figure 45:
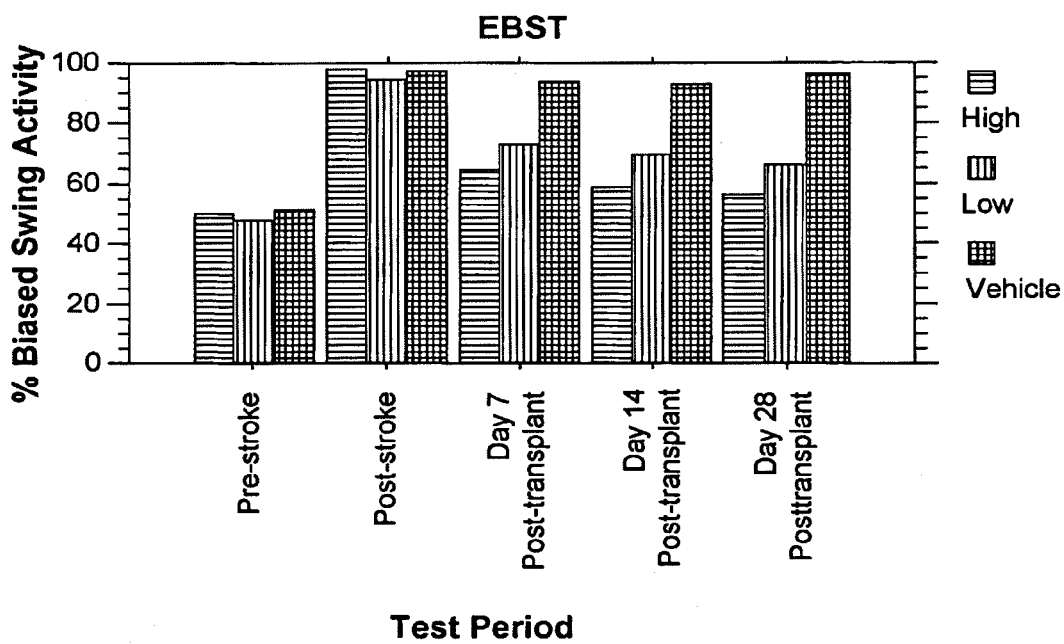
FIG. 45 shows results from EBST performed in Example 9.

Following random assignments of the stroke animals to either vehicle, low dose 90 k NPCs, or high dose 180 k NPCs, ANOVA revealed significant treatment effects for both tests (p's<0.0001). Pair-wise comparisons between treatment groups revealed that as early as day 7 post-transplantation, stroke animals that were transplanted with NPCs, regardless of the dose, exhibited significant amelioration of behavioral deficits compared to vehicle-treated stroke animals (p's<0.05). This behavioral recovery by NPC transplanted stroke animals was sustained at day 14 and day 28 post-transplantation, in that NPC GFUs again regardless of the dose promoted significant attenuation of both motor and neurological impairments compared to vehicle treatment (p's<0.0001). Closer examination of the two NPC doses revealed that the high dose 180 k produced significantly better amelioration of behavioral deficits compared to the low dose 90 k across all post-transplantation test days for EBST (p's<0.01), and at days 14 and 28 post-transplantation test days for Bederson (p's<0.0005). Results are shown in FIGS. 44-45.

The present behavioral data demonstrated the robust therapeutic benefits of NPCs in that behavioral recovery was detected as early as day 7 post-transplantation. Results further revealed that the positive outcome of NPC grafts was stable up to day 28 post-transplantation (the study cut-off period). Although both low and high dose of NPCs promoted functional benefits, the high dose provided significantly better behavioral recovery than the low dose.

All stroke animals in this study were immunosuppressed. As the vehicle-treated stroke animals did not display any observable behavioral recovery, this eliminated the possible confounding beneficial effects of the immunosuppressant CsA as seen previously in studies incorporating delivery of the drug at pre-stroke period, during or immediately after stroke. The observed behavioral recovery being limited to NPC transplanted stroke animals indicate that the source of the therapeutic effects is not likely from the immunosuppression per se, but from the grafted cells.

Hematoxylin and eosin (H&E) and Nissl staining was conducted to measure the maximum infarcted area in each animal using an NIH imaging system. To calculate infarct volume, the following formula was used=2 mm (thickness of the slice)×[sum of the infarction area in all brain slices (mm$^2$)].

At one month post-transplantation, randomly selected animals were euthanized for immunohistochemistry. Tissues were processed using standard ABC method using the following procedures. 20 μm cryostat sectioned tissues were be examined at 4× magnification and digitized using a PC-based Image Tools computer program. Brain sections were blind-coded and Abercrombie's formula was used to calculate the total number of immunopositive cells.

NPC survival following transplantation was assessed using monoclonal human specific antibody HuNu, human cell surface markers which do not cross react with rodent cell surface markers or other rodent proteins. To detect expression of neuronal, glial and oligodendrocyte phenotype in cell grafts, immunohistochemical analysis, Neu-N and GFAP, was used, respectively. These cell surface markers also revealed migration of engrafted NPCs.

Figure 46:
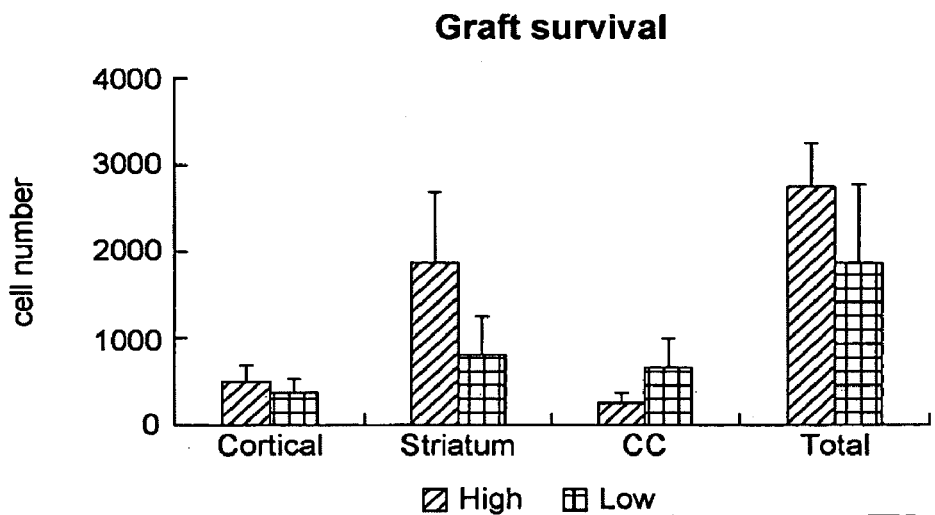
FIG. 46 illustrates graft survival according to Example 9.
Figure 47:
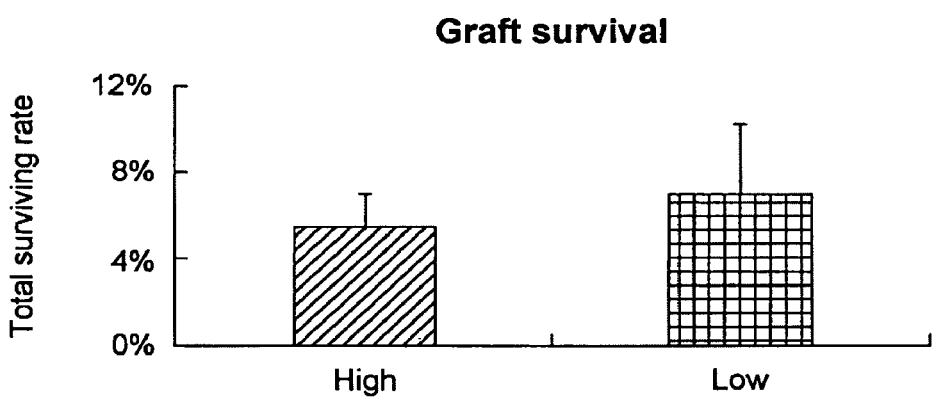
FIG. 47 shows graft survival according to Example 9.
Figure 48:
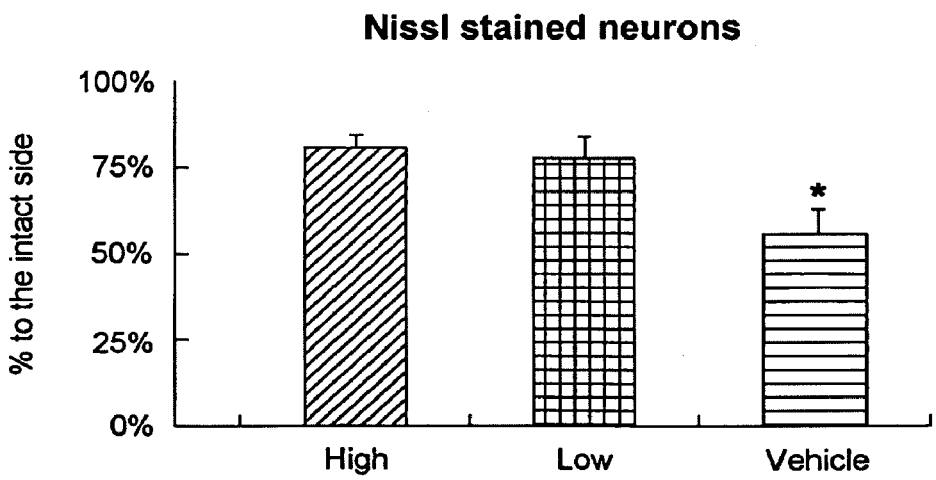
FIG. 48 shows the results of Nissl staining according to Example 9.

Generally, the NPCs survived well in the striatum with a few neurons positive for MAP2 expression at 1 month post-transplantation. The graft survival did not differ significantly between the two dose levels of NPCs. NPCs reduced the ischemic cell loss in the stroke penumbra. The two dose levels showed almost the same extent of neuro-rescue effects. Data from these analyses is presented in FIGS. 46-48.

H. MNC Examples

The Examples set forth below are meant to be illustrative, and in no way limiting, of the scope of the present invention.

Experimental Procedures.

Culturing of MASCs and Neuronal Induction

MASCs were isolated from Wistar rats generally as described previously in S. Azizi et al. "Engraftment and migration of human bone marrow stromal cells implanted in the brains of albino rats—similarities to astrocyte grafts." Proc Natl Acad Sci USA, 1998; 95:3908-13. The MASCs were labeled with green fluorescent protein (GFP) by retroviral infection using the pBabe neo-GFP vector generally as described in M. Dezawa et al., "Sciatic nerve regeneration in rats induced by transplantation of in vitro differentiated bone-marrow stromal cells." Eur J Neurosci. 2001; 14:1771-6.

Neuronal induction from MASCs is generally as described in M. Dezawa et al., "Specific induction of neuronal cells from bone-marrow stromal cells and application for autologous transplantation J Clin Invest. 2004; 113:1701-10. Briefly, a vector (pCI neo-NICD) containing the Notch intracellular domain (NICD) was transfected into MASCs using Lipofectamin2000 (Invitrogen Corp., Carlsbad, Calif.). Cells were selected by G418 after 11 days. For induction of MNCs, NICD-transfected MASCs were subcultured once (60-70% confluence) and were incubated in alpha-MEM containing 10% FBS, 5 μM FSK (Calbiochem, La Jolla, Calif.), 10 ng/ml bFGF (Peprotech, London, UK) and 10 ng/ml CNTF (R&D Systems, Minneapolis, Minn.). Five days later, cells were transplanted into the MCAO rat model. To characterize the induced MNCs in vitro, immunocytochemistry was performed. Anti-MAP-2ab (Sigma, St. Louis, Mo.), neurofilament-M (NF-M) (Chemicon, Temecula, Calif.) and beta-tubulin isotype 3 (β-tubulin3) (Sigma, St. Louis, Mo.) were used as neuronal markers, and 90-95% of MNCs were shown to be immunopositive for these markers.

MCAO Rat Model:

Male Wistar rats weighing 200-250 g were kept at room temperature (24° C.) with a 12-h light-dark cycle, and were given food and water freely. The MCAO procedure was a modification of the methods described in J. Koizumi et al., "Experimental studies of ischemic brain edema. 1. A new experimental model of cerebral embolism in rats in which recirculation can be introduced in the ischemic area." Jpn J Stroke. 1986; 8:1-8; and E. Longa et al., "Reversible middle cerebral artery occlusion without craniectomy in rats." Stroke. 1989; 20:84-91. Briefly, under deep anesthesia induced by a mixture of 1.0-1.5% halothane, 10% O2 and air, a midline cervical incision was performed, and the left carotid bifurcation was identified. A probe made of 4-0 Nylon thread with a silicon rubber-coated head of diameter 0.3 mm was inserted into the ligated external carotid artery and advanced into the internal carotid artery to a position 16-18 mm from the bifurcation. During the surgery, rectal temperature was maintained between 37.5-38.0° C. using a feedback-heating pad (BWT-100, Bio Research Center Co. Ltd., Tokyo, Japan).

Arterial blood gas analysis was performed and pO2 was maintained at 85-120 mmHg through control of the anesthetic device. Reperfusion was performed 4 hours after the occlusion through a 10 mm withdrawal of the probe.

Transplantation

On day 7 following the MCAO procedure, rats were anesthetized with intraperitoneal injection of 50 mg/kg sodium pentobarbital and placed onto a sterotaxic frame. In a preliminary experiment, the infarct area was produced in the lateral area from approximately 3.5 mm lateral to the midline. For transplantation into the non-necrotic brain parenchyma, the cell suspension, composed of 8000-16000 cultured cells in 3 μl of phosphate buffered saline (PBS, pH 7.4), was stereotaxically injected into the left forebrain from the following 3 locations: +2 mm, 0 mm and −2 mm anterior to the bregma, and 2 mm lateral to the midline and at 1.2 mm depth from the cortical surface in each case. Total numbers of transplanted cells were 24000-48000.

Three groups of animals were prepared; the control group, which received only PBS (without cell transplantation) (n=7), the MASC group, which underwent transplantation of non-treated intact MASCs (n=10), and the NMC group, into which MNCs were transplanted (n=10).

Behavioral Testing

The severity of neurological damage was evaluated using the following tests: beam balance test, limb placing test and Morris water maze test. Beam balance test and limb placing test were performed on day 7 gust before transplantation), 14, 21, 28 and 35 after MCAO. Morris water maze test was performed from day 36 to 40 following the MCAO procedure.

Beam Balance Test

The beam balance test is used to assess gross vestibulomotor function, and was carried out generally as described previously in C. Dixon et al., "A fluid percussion model of experimental brain injury in the rat." J Neurosurg. 1987; 67:110-9. Scoring was based on the following criteria: balancing with a steady posture with paws on the top of the beam: a score of 0; grasping the sides of the beam and/or shaky movement: 1; one or more paw(s) slipping off the beam: 2; attempting to balance on the beam, but falling off: 3; and falling off the beam with no attempt to balance or hang on: 4.

Limb Placing Test

The limb placing test examines sensorimotor integration in limb placing responses to visual, tactile and proprioceptive stimuli, and was performed generally as described previously in M. De Ryck et al. "Photochemical stroke model: flunarizine prevents sensorimotor deficits after neocortical infarcts in rats." Stroke, 1989; 20:1383-1390. A proprioceptive adduction test was also performed, again generally according to the procedures laid out in the De Ryck et al. article. For each test, scoring was based on the following criteria: immediate and complete placing of the limb: a score of 0; incomplete and/or delayed (>2 seconds) placing, including interspersed flailing: 1; and no placing: 2. Visual, forward tactile and lateral tactile, proprioceptive stimuli were given to right forelimb. Forward tactile and lateral tactile and proprioceptive stimuli were given to right hindlimb. Proprioceptive adduction test were performed in both forelimb and hindlimb. Total score ranges 0-18.

Morris Water Maze Test

The Morris water maze test is a useful method to assess cognitive function. Several modification of this test has been reported. A version of the test generally as reported in A. Fukunaga et al., "Differentiation and angiogenesis of central nervous system stem cells implanted with mesenchyme into ischemic rat brain." Cell Transplant. 1999; 8:435-41 was used. This test was performed from day 36 to day 40 after MCAO. A pool (diameter 150 cm, depth 35 cm) was prepared. An escape platform (diameter 10 cm) was located 1 cm beneath the surface of the water rendered opaque and milky white. Four starting points around the edge of the pool were designed as N, E, S and W. The platform was kept in the middle of a quadrant, equidistant from the center and the edge of the pool. A rat was released into the water from each starting point and allowed to swim until reaching the platform, and the time taken to reach the platform was recorded (maximum of 120 seconds). Rats were trained in the task using two sets of four trials on each of 5 consecutive days. After the first set on the fifth day, instead of the second set, a spatial probe trial was performed. This test is to estimate short memory retention. The platform was removed and the rat was allowed to swim for 60 seconds. The number of times each animal crossed the platform-located area was measured. The time spent in the platform-located quadrant was also measured.

Histological Analysis

On day 41, rats were sacrificed with administration of a pentobarbital overdose, and perfused transcardinally with 0.9% saline followed by periodate-lysine-paraformaldehyde fixative solution as generally described in 1. McLean et al., "Periodate-lysine-paraformaldehyde fixative. A new fixation for immunoelectron microscopy." J Histochem Cytochem. 1974; 22:1077-83. The brain was cut into coronal blocks of 2 mm thickness using Brain Matrix (BAS Inc. Warwickshire, UK). 10 μm-thick cryostat sections were made from each block. Sections were stained with hematoxylin and eosin (H&E) to evaluate the infarct area. The images of sections were captured using a 1× objective lens under a light microscope, and the lesion areas were traced using Scion Image (Scion Corporation, Frederick, Md.). The infarct volume was calculated generally as described previously in R. Swanson et al., "A semiautomated method for measuring brain infarct volume." J Cereb Blood Flow Metab. 1990; 10:290-29, and expressed as a percentage of the volume of the contralateral hemisphere.

For immunostaining, the sections were incubated with primary antibodies to MAP-2 (1:100, Boehringer Mannheim, Germany), β-tubulin3 (1:400, Sigma, Mo.), NF-M (1:200, Boehringer Mannheim, Germany), Tuj-1 (1:100, BAbCO, CA), or GFAP (1:400, Dako, Calif.) at 4° C. overnight. Alexa Fluor 546-conjugated anti-mouse IgG (Molecular Probes, Eugene, Oreg.) (for MAP-2) or anti-rabbit IgG (Molecular Probes, Eugene, Oreg.) (for β-tubulin3, NF-M, Tuj-1 and GFAP) was used as the secondary antibody. TOTO-3 was used for the nuclear staining. Specimens were inspected using confocal laser scanning microscopy (CLMS) (Radiance 2000, Bio-Rad, Hertfordshire, UK).

In each rat the total number of GFP-labeled cells in the whole forebrain was calculated. The number of GFP-labeled cells in the hippocampus also calculated in the same way.

Statistical Analysis

The behavioral evaluation data and infarct volume data were analyzed using a non-repeated measures ANOVA. When the results were significant ($p<0.05$), Student-Newman-Keuls post hoc procedure was used at a 95% significant level. The values are presented as mean±standard deviation, unless otherwise stated.

Example 10

Behavioral Testing

One week after MCAO was performed, and just before the transplantation, severe right side neurological deficits were apparent, and the mean score for each behavioral test showed no statistical differences among the three groups.

Beam Balance Test

Figure 40:
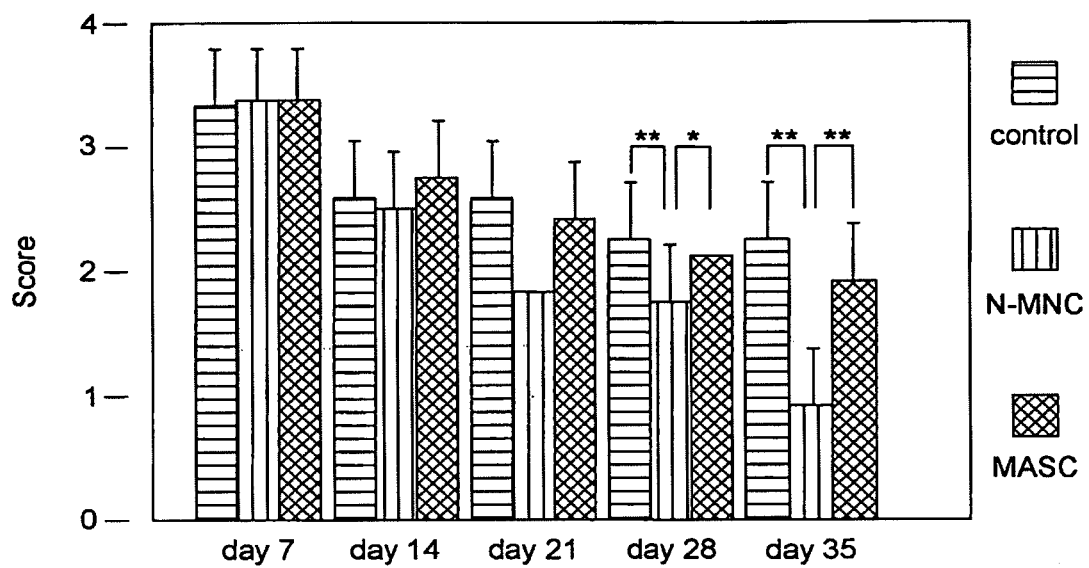
FIG. 40 shows the results of a beam balance test. On day 28 after transplantation, the mean score for the MNC group showed a significant improvement, compared with the MASC and control groups. *: $p<0.05$, **: $p<0.01$

From day 7 to day 21, the mean score was not statistically different among the three groups. On day 28 and 35, the mean score of the NMC group showed a significant improvement, compared with the control (day 28: p=0.0041, day 35: p=0.0001) and MASC groups (p=0.0471, 0.0007 respectively). Although MASC group showed slight improvement compared with the control, statistically significant difference could not be detected on day 28 and 35 (FIG. 40).

Limb Placing Test

Figure 41:
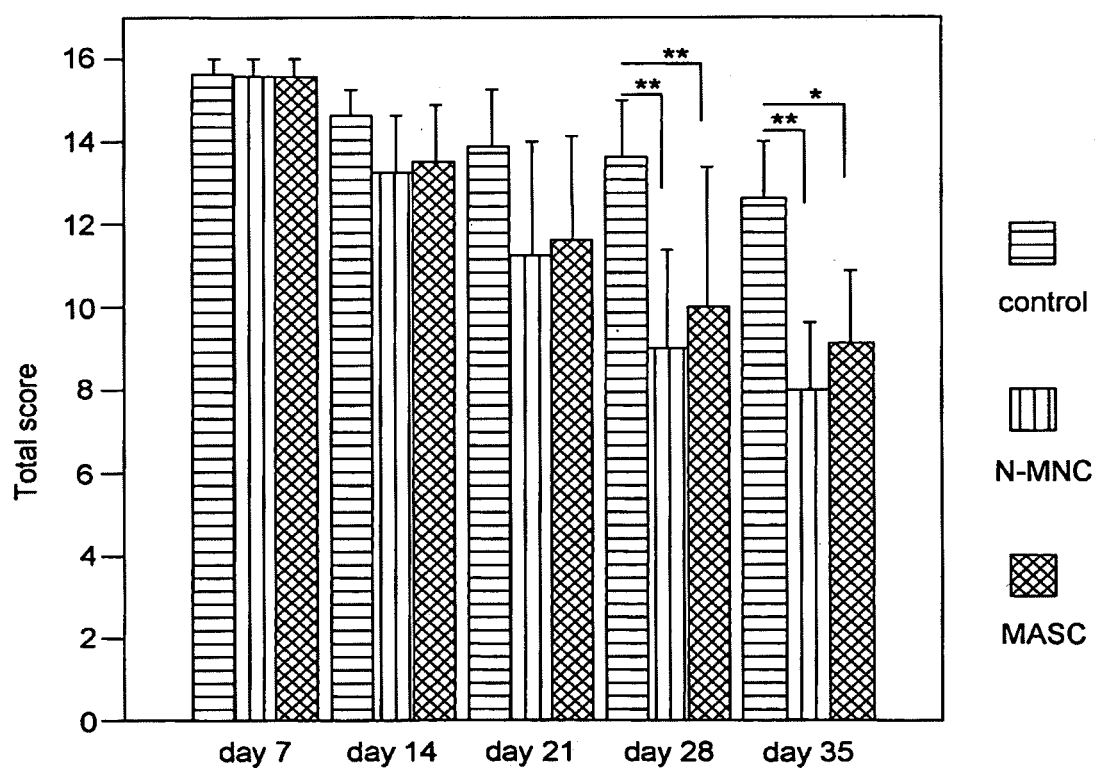
FIG. 41 shows the results of a limb placing test. The mean scores for the NMC group and the MASC group were significantly different to that of the control group on day 21 and day 28. There was no significant difference between the MNC and MASC groups. *: $p<0.05$, **: $p<0.01$

There were no statistical differences between the mean score of three groups from day 7 to day 21. On day 28 and 35, the NMC and MASC groups showed a significant improvement, compared with the control group (day28: p=0.0022 and 0.085, day35: p=0.0022 and 0.0211 respectively). However, the mean score showed no significant difference between the NMC and MASC groups throughout the entire period (FIG. 41).

Morris Water Maze Test

Figure 42:
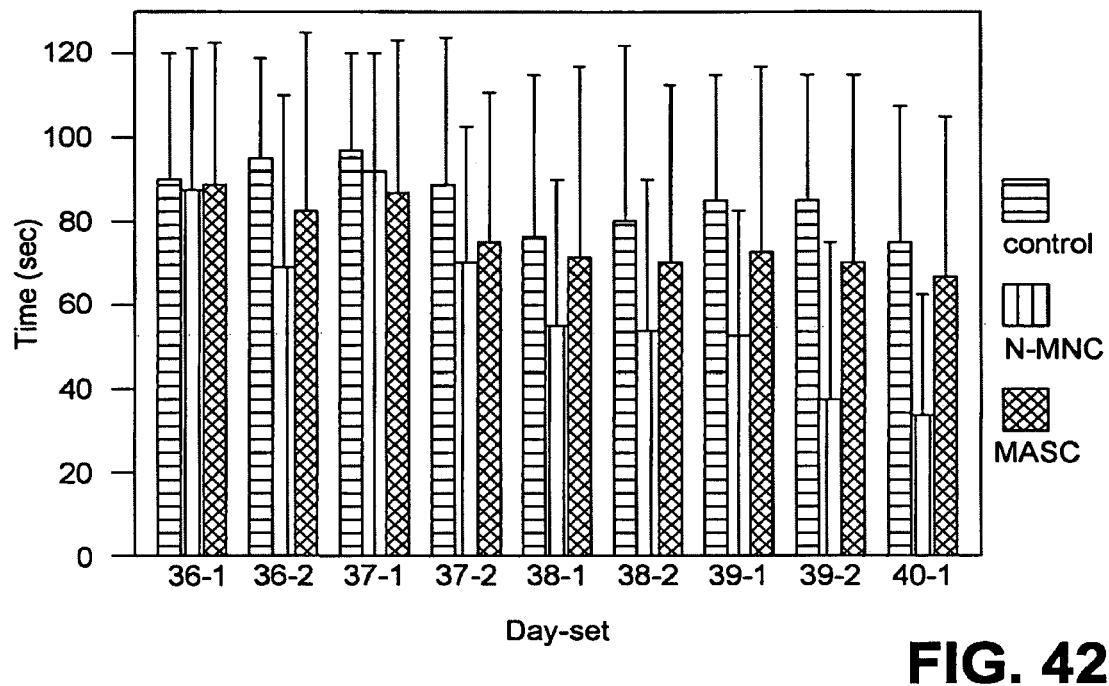
FIG. 42 shows the results of a Morris water maze test. For the final set, the mean latency time for the MNC group was significantly different to those for the MASC and control groups.

The mean latency time recorded in each set of four trials to locate the submerged escape platform is shown in FIG. 42 for each of the three groups. The NMC group showed the shortest latency time compared to the control and MASC group. The mean latency time for the second set on day 39 and the first set on day 40 demonstrated significant difference between the NMC and control groups (p=0.0339 and 0.0492 respectively) (FIG. 42). Although the NMC group showed a tendency to take shorter latency time to the escape platform than MASC group, a statistically significant difference did not exist.

Figure 43:
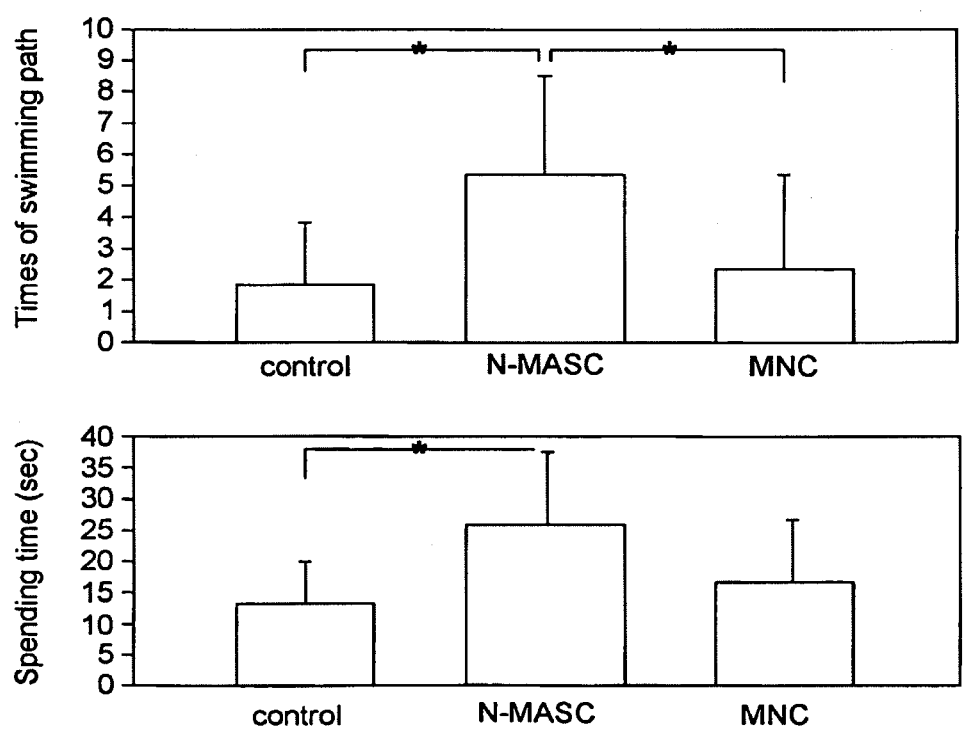
FIG. 43 shows the results of a water maze "spatial probe trial". Among the three groups, the best results were obtained for the MNC group, and statistical differences were obtained between the MNC group and the other groups. *: $p<0.05$, **: $p<0.01$

In the spatial probe trial, rats in the NMC group showed a significant improvement compared with the control (p=0.0419) and MASC group (p=0.0453) (FIG. 43). The mean time spent in the platform-located quadrant was the longest in NMC group among three groups. Significant difference existed between NMC and control (p=0.0339) (FIG. 43).

Example 11

Histological Study

The infarct area was located in the lateral half of the left hemisphere including cortex, striatum and hippocampus, and formation of cysts and scars was observed in most lesioned brains. The hippocampus of the lesion side was atrophic and showed partially irregular arrangement or loss of neurons compared with contralateral side. Infarct volumes were measured in all MCAO models. The mean infarct volume in the NMC, MASC and control groups on day 33 were 50.7±10.9%, 51.0±10.2% and 50.9±11.1% respectively. There was no statistically significant difference among the three groups.

Transplanted GFP-labeled MASCs and MNCs were located mainly at the boundary area between intact tissue and infarct area including the ipsilateral cortex, corpus callosum, striatum and hippocampus. The infiltration of inflammatory cells into the infarct focus was observed. There seemed to be no difference in the number of inflammatory cells that infiltrated inot the infarct locus between the MNC and MASC groups.

A large number of GFP-labeled MNCs were immunopositive for MAP-2 and showed neurite development in the host brain. They were also immunopositive for Tuj-1 and β-tubulin3. In the ipsilateral hippocampus, many cell bodies and neurites of GFP-labeled MNCs were also shown to be NF-M positive. A large fraction of GFP-labeled transplanted MNCs were positive for MAP-2 (84.0±8.1%), whereas only a small number of cells were positive for GFAP (1.0±0.2%).

In contrast, the large majority of MASCs in the host brain were negative for both neuronal (MAP-2, Tuj1, β-tubulin3 and NF-M) and glial (GFAP) markers. The percentages of MAP-2– and GFAP-positive cells among the GFP-labeled cells were 1.4±0.2% and 4.8±1.0%, respectively. The formation of neurites in MAP-2 positive MASC could not be found.

The mean number of MNCs and MASCs in the host forebrain were 13250±1126 and 5850±997. Approximately 30-45% of transplanted MNCs were detected and, on the other hand, 10-20% of transplanted MASCs were detected one month after the transplantation. The survival ratio of MNCs in the ischemic brain was substantially higher than MASCs. In the hippocampus, the mean number of MNCs was 790±160 and 89% of them were MAP2-positive. The mean number of MASCs, in contrast, was 470±66 and 0.6% were MAP2-positive, showing that most of transplanted MASCs were negative for both neuronal and glial markers.

In all groups, tumor formation was not observed in the brain parenchyma up to 41 days after MCAO.

REFERENCES

Aihara N, Mizukawa K, Koie K, Mabe H. Nishino H. Striatal grafts in infarct striatopallidum increase GABA release, recognize GABAa receptor and improve water maze learning in the rat. Brain Res. 1994; 33:483-488.

Altumbabic M, Peeling J, Del Bigio M R. Intracerebral hemorrhage in the rat: effects of hematoma aspiration. Stroke. 1998; 29:1917-22.

Azizi, S. A., Stokes, D., Augelli, B. J., DiGirolamo, C., Prockop, D. J. Engraftment and migration of human bone marrow stromal cells implanted in the brains of albino rats—similarities to astrocyte grafts. Proc Natl Acad Sci USA, 1998; 95:3908-13.

Bederson J B, Pitts L H, Tsuji M, Nishimura M C, Davis R L, Bartkowski H. Rat middle cerebral artery occlusion: evaluation of the model and development of a neurologic examination. Stroke. 1986; 17:472-6.

Bjorklund A, Lindvall O. Cell replacement therapies for central nervous system disorders. Nat Neurosci. 2000; 3:537-44.

Borlongan C V, Cahill D W, Sanberg P R. Locomotor and passive avoidance deficits following occlusion of the middle cerebral artery. Physiol Behav. 1995, 58:909-17.

Borlongan C V, Fujisaki T, Watanabe S. Chronic cyclosporine-A injection in rats with damaged blood-brain barrier does not impair retention of passive avoidance. Neurosci Res. 1998, 32:195-200.

Borlongan C V, Hida H, Nishino H. Early assessment of motor dysfunctions aids in successful occlusion of the middle cerebral artery. Neuroreport. 1998; 9:3615-21.

Borlongan C V, Tajima Y, Trojanowski J Q, Lee V M, Sanberg P R Transplantation of cryopreserved human embryonal carcinoma-derived neurons (NT2N cells) promotes functional recovery in ischemic rats. Exp Neurol. 1998; 149: 310-21.

Borlongan C V, Yamamoto M, Takei N, Kumazaki M, Ungsuparkorn C, Hida H, Sanberg P R, Nishino H. Glial cell survival is enhanced during melatonin-induced neuroprotection against cerebral ischemia. FASEB J. 2000; 14:1307-17

Brundin P, Widner H. Nilsson O G, Strecker R E, Bjorklund A. Intracerebral xenografts of dopamine neurons: the role of immunosuppression and the blood-brain barrier. Exp Brain Res. 1989; 75:195-207.

Butcher S P, Henshall D C, Teramura Y, Iwasaki K, Sharkey J. Neuroprotective actions of FK506 in experimental stroke: in vivo evidence against an antiexcitotoxic mechanism. J, Neurosci. 1997; 17:6939-46.

Butovas S, Lukkarinen J, Virtanen T, Jolkkonen J, Sivenius J. Differential effect of the alpha2-adrenoceptor antagonist, atipamezole, in limb-placing task and skilled forepaw use following experimental stroke. Restor Neurol Neurosci. 2001; 18:143-51.

Chen J, Li Y, Wang L, Lu M, Zhang X, Chopp M. Therapeutic benefit of intracerebral transplantation of bone marrow stromal cells after cerebral ischemia in rats. J Neurol Sci. 2000; 189:49-57.

Chen J, Sanberg P R, Li Y, Wang L, Lu M, Willing A E, Sanchez-Ramos J, Chopp M. Intravenous administration of human umbilical cord blood reduces behavioral deficits after stroke in rats. Stroke. 2001 November; 32(11):2682-8

Chen J, Li Y, Wang L, Zhang Z, Lu D, Lu M, Chopp M. Therapeutic benefit of intravenous administration of bone marrow stromal cells after cerebral ischemia in rats. Stroke. 2001; 32:1005-11.

Chopp M, Li Y. Treatment of neural injury with marrow stromal cells. Lancet Neurol. 2002; 1:92-100.

Chu, K, Manho Kim, Kyung-II Park, Sang-Wuk Jeong, Hee-Kwon Park, Keun-Hwa Jung, Soon-Tae Lee, Lami Kang, Kyungmi Lee, Dong-Kyu Park, Seung U. Kim and Jae-Kyu Roh. Human neural stem cells improve sensorimotor deficits in the adult rat brain with experimental focal ischemia. Brain Research, 2004 1016:145-153

Cicchetti F, Fodor W, Deacon T W, van Home C, Rollins S, Burton W. Costantini L C, Isacson O. Immune parameters relevant to neural xenograft survival in the primate brain. Xenotransplantation 2003; 10:41-9

Dezawa M, Takahashi I, Esaki M, Takano M, Sawada H. Sciatic nerve regeneration in rats induced by transplantation of in vitro differentiated bone-marrow stromal cells. Eur J Neurosci. 2001; 14:1771-6.

Dezawa M, Kanno H, Hoshino M, Cho H, Matsumoto N, Itokazu Y. Tajima N, Yamada H, Sawada H, Ishikawa H, Mimura T, Kitada M, Suzuki Y, Ide C. Specific induction of neuronal cells from bone marrow stromal cells and application for autologous transplantation. J Clin Invest. 2004; 113:1701-10.

De Ryck M, Van Reempts J, Borgers M, Wauquier A, Janssen P A J. Photochemical stroke model: flunarizine prevents sensorimotor deficits after neocortical infarcts in rats, Stroke, 1989; 20:1383-1390.

Ding Y, Li J, Luan X, Ding Y H, Lai Q, Rafols J A, Phillis J W, Clark J C, Diaz F G. Exercise pre-conditioning reduces brain damage in ischemic rats that may be associated with regional angiogenesis and cellular overexpression of neurotrophin. Neuroscience. 2004; 124(3):583-91.

Dixon C E, Lyeth B G, Povilshock J T, Findling R L, Hamm R J, Marmarou A, Young H F, Hayes R L. A fluid percussion model of experimental brain injury in the rat. J Neurosurg. 1987; 67:110-9.

Fahr A. Cyclosporin clinical pharmacokinetics. Clin Pharmacokinet. 1993 June; 24(6):472-95.

Ferrari G, Cusella-De Angelis G, Coletta M, Paolucci E, Stomaiuolo A, Cossu G, Mavilio F. Muscle regeneration by bone marrow-derived myogenic progenitors. Science. 1998; 279:1528-30.

Fukuda S, del Zoppo, G J. Models of focal cerebral ischemia in the nonhuman primate. ILAR J. 2003; 44(2):96-104.

Fukunaga A, Uchida K, Hara K, Kuroshima Y, Kawase T. Differentiation and angiogenesis of central nervous system stem cells implanted with mesenchyme into ischemic rat brain. Cell Transplant. 1999; 8:435-41.

Furuichi, Y. Masashi Maeda, Akira Moriguchi, Taiji Sawamoto, Akio Kawamura, Nobuya Matsuoka, Seitaro Mutoh, and Takehiko Yanagihara. Tacrolimus, a Potential Neuroprotective Agent, Ameliorates Ischemic Brain Damage and Neurologic Deficits After Focal Cerebral Ischemia in Nonhuman Primates. Journal of Cerebral Blood Flow & Metabolism. 23:1183-1194, 2003

Gharbawie O A, Gonzalez C L, Whishaw I Q. Skilled reaching impairments from the lateral frontal cortex component of middle cerebral artery stroke: a qualitative and quantitative comparison to focal motor cortex lesions in rats. Behav Brain Res. 2005; 156:125-37.

Gonzalez C L, Kolb B. A comparison of different models of stroke on behaviour and brain morphology. Eur J Neurosci. 2000; 18:1950-62.

Goto S, Yamada K, Yoshikawa M, Okamura A, Ushio Y. GABA receptor agonist promotes reformation of the striatonigral pathway by transplant derived from fetal striatal promordia in the lesioned striatum. Exp Neurol. 1997; 147:503-509.

Grabowski M, Johansson B B, Brundin P. Survival of fetal neocortical grafts implanted in brain infarcts of adult rats: the influence of postlesion time and age of donor tissue. Exp Neurol. 1994; 127:126-36.

Green R, Odergren T, Ashwood T. Animal models of stroke: do they have value for discovering neuroprotective agents? Trends Pharmacol Sci. 2003; 24:402-8.

Hartings J A, Williams A J, Tortella F C. Occurrence of nonconvulsive seizures, periodic epileptiform discharges, and intermittent rhythmic delta activity in rat focal ischemia. Exp Neurol. 2003; 179:139-49.

Huang, J MD; J. Mocco, MD; Tanvir F. Choudhri, MD; Alexander Poisik, MD; Sulli J. Popilskis, DVM; Ronald Emerson, MD; Robert L. DelaPaz, MD; Alexander G. Khandji, MD; David J. Pinsky, MD; E. Sander Connolly, Jr, MD. A Modified Transorbital Baboon Model of Reperfused StrokeStroke. 2000; 31:3054-63.

Jiang Y, Jahagirdar B N, Reinhardt R L, Schwartz R E, Keene C D, Ortiz-Gonzalez X R, Reyes M, Lenvik T, Lund T, Blanckstad M, Du J, Aldrich S. Lisberg A, Low W C, Largaespada D A, Verfaillie C M. Pluripotency of mesenchymal stem cells derived from adult marrow. Nature. 2002; 418:41-49.

Kaminska, B, Gaweda-Walerych, K, Zawadzka, M. Molecular mechanisms of neuroprotective action of immunosuppressants—facts and hypotheses. J Cell Mol Med. 2004; 8:45-58.

Koizumi J, Yoshida Y, Nakazawa T, Ooneda G, Experimental studies of ischemic brain edema. 1. A new experimental model of cerebral embolism in rats in which recirculation can be introduced in the ischemic area. Jpn J Stroke. 1986; 8:1-8.

Kohyama J, Abe H, Shimazaki T, Koizumi A, Nakashima K, Gojo S, Taga T, Okano H, Hata J, Umezawa A. Brain from bone: efficient "meta-differentiation" of marrow stroma-derived mature osteoblasts to neurons with Noggin or a demethylating agent. Differentiation. 2001; 68:235-44.

Kondziolka D, Wechsler L, Achim C. Neural transplantation for stroke. J Clin Neurosci. 2002; 9:225-30.

Kondziolka D, Wechsler L, Goldstein S, Meltzer C, Thulborn K R, Gebel J, Jannetta P, DeCesare S, Elder E M, McGrogan M, Reitman M A, Bynum L. Transplantation of cultured human neuronal cells for patients with stroke. NeuroLogy. 2000; 55:565-9.

Lemaire M, Pardridge W M, Chaudhuri G. Influence of blood components on the tissue uptake indices of cyclosporin in rats. J Pharmacol Exp Ther. 1988; 24:740-3.

Li Y, Chopp M, Chen J, Wang L, Gautam S C, Xu Y X, and Zhang Z. Intrastriatal transplantation of bone marrow non-hematopoietic cells improves functional recovery after stroke in adult mice. J Cereb Blood Flow Metab. 2000; 20:1311-19.

Lindner M D, Gribkoff V K, Donlan N A, Jones T A. Long-lasting functional disabilities in middle-aged rats with small cerebral infarcts. J Neurosci. 2003; 23:10913-22.

Lindvall O, Kokaia Z, Martinez-Serrano A. Stem cell therapy for human neurodegenerative disorders-how to make it work. Nat Med. 2004; 10 Suppl:S42-50.

Longa E Z, Weinstein P R, Carlson S, Cummins R. Reversible middle cerebral artery occlusion without craniectomy in rats. Stroke. 1989; 20:84-91.

Mack, W J, Ricardo J. Komotar, J Mocco, Alexander L. Coon, Daniel J. Hoh, Ryan G. King, Andrew F. Ducruet, Evan R. Ransom, Marcello Oppermann, Robert DeLaPaz and E. Sander Connolly Jr. Serial magnetic resonance imaging in experimental primate stroke: Validation of MRI for preclinical cerebroprotective trials. Neurological Research, 2003; 25:846-852.

Makino S, Fukuda K, Miyoshi S, Konishi F, Kodama H, Pan J, Sano M, Takahashi T, Hori S, Abe H, Hata J, Umezawa A, Ogawa S. Cardiomyocytes can be generated from marrow stromal cells in vitro. J Clin Invest. 1999; 103:697-705.

Markgraf C G, Green E J, Watson B, McCabe P M, Schneiderman N, Dietrich W D, Ginsberg M D. Recovery of sensorimotor function after distal middle cerebral artery photothrombotic occlusion in rats. Stroke. 1994; 25:153-9.

Marshall J W, Ridley R M. Assessment of cognitive and motor deficits in a marmoset model of stroke. ILAR J. 2003; 44:153-60.

Matsumoto S, Isshiki A, Watanabe Y, Wieloch T. Restricted clinical efficacy of cyclosporin A on rat transient middle cerebral artery occlusion. Life Sci. 2002; 72:591-600.

McLean I W, Nakane P K. Periodate-lysine-paraformaldehyde fixative. A new fixation for immunoelectron microscopy. J Histochem Cytochem. 1974; 22:1077-83.

Modo, M, R. Paul Stroemer, PhD; Ellen Tang, BSc; Sara Patel, PhD; Helen Hodges, PhD. Effects of Implantation Site of Stem Cell Grafts on Behavioral Recovery From Stroke Damage. Stroke. 2002; 33:2270-2278.

Modo, M, R. P. Stroemer, E. Tang, T. Veizovic, P. Sowniski, H. Hodges. Neurological sequelae and long-term behavioural assessment of rats with transient middle cerebral artery occlusion. Journal of Neuroscience Methods 2000; 194:99-109.

Morris R G M. Spatial localization does not require the presence of local cues. Learn Motiv. 1981; 12:239-260.

Nikkhah G, Rosenthal C, Hedrich H J, Samii M. Differences in acquisition and full performance in skilled forelimb use as measured by the 'staircase test' in five rat strains. Behav Brain Res. 1998; 92:85-95

Nishino H and Borlongan C V. Restoration of function by neural transplantation in the ischemic brain. Prog Brain Res. 2000; 127:461-76.

Nudo R J, Larson D, Plautz E J, Friel K M, Barbay S, Frost S B. A squirrel monkey model of poststroke motor recovery. ILAR J. 2003; 44:161-74.

Orlic D, Kajstura J, Chimenti S, Jakoniuk I, Anderson S M, Li B, Pickel J, McKay R, Nadal-Ginard B, Bodine D M, Leri A. Anversa P. Bone marrow cells regenerate infarcted myocardium. Nature. 2001; 410:701-5.

Pakzaban P, Isacson O. Neural xenotransplantation: reconstruction of neuronal circuitry across species barriers. Neuroscience. 1994; 62:989-1001.

Pedersen E B, Zimmer J. Finsen B. Triple immunosuppression protects murine intracerebral, hippocampal xenografts in adult rat hosts: effects on cellular infiltration, major histocompatibility complex antigen induction and blood-brain barrier leakage. Neuroscience. 1997; 78:685-701.

Plautz, E J, Barbay, S, Frost, S B, Friel, K M, Dancause, N, Zoubina, E V, Stowe, A M, Quaney, B M and R J Nudo. Post-infarct cortical plasticity and behavioral recovery using concurrent cortical stimulation and rehabilitative training: A feasibility study in primates. Neurological Research, 2003, 25:801-810

Roitberg, B. Transplantation for stroke. Neurol Res. 2004; 26:256-64.

Roitberg, B., Khan, N., Tuccar, E., Kompoliti, K., Chu, Y, Alperin, N., Kordower, J H, and M E Emborg. Chronic ischemic stroke model in cynomologous monkeys: Behaviral, neuroimaging and anatomical study. Neurological Research, 2003, 25:68-78.

Roof R L, Schielke G P, Ren X, Hall E D. A comparison of long-term functional outcome after 2 middle cerebral artery occlusion models in rats. Stroke. 2001; 32:2648-57.

Sanchez-Ramos, JR. Neural cells derived from adult bone marrow and umbilical cord blood. J Neurosci Res. 2002; 69:880-893.

Sorensen J C, Grabowski M, Zimmer J, Johansson B B. Fetal neocortical tissue blocks implanted in brain infarcts of adult rats interconnect with the host brain. Exp Neurol. 1996; 138:227-35.

Stroke Therapy Academic Industry Roundtable (STAIR). Recommendations for Standards Regarding Preclinical Neuroprotective and Restorative Drug Development. Stroke. 1999; 30:2752-2758.

Sullivan P G, Rabchevsky A G, Hicks R R, Gibson T R, Fletcher-Turner A, Scheff S W. Dose-response curve and optimal dosing regimen of cyclosporin A after traumatic brain injury in rats. Neuroscience. 2000; 101:289-9

Swanson R A, Morton M T, Tsao-Wu G, Savalos R A, Davidson C, Sharo F R. A semiautomated method for measuring brain infarct volume. J Cereb Blood Flow Metab. 1990; 10:290-293

Szentirmai O, Carter B S. Neurosurgery. Genetic and cellular therapies for cerebral infarction. 2004; 55:283-6.

Takamatsu, H, Hideo Tsukada, Akihiro Noda, Takeharu Kakiuchi, Shingo Nishiyama, Shintaro Nishimura, and Kazuo Umemura. FK506 Attenuates Early Ischemic Neuronal Death in a Monkey Model of Stroke. J Nucl Med 2001; 42:1833-1840

Toda H, Takahashi J, Iwakami N, Kimura T, Hoki S, Mozumi-Kitamura K, Ono S. Hashimoto N. Grafting neural stem cells improved the impaired spatial recognition in ischemic rats. Neurosci Lett. 2001 Dec. 4; 316(1):9-12

Umezawa A, Maruyama T, Segawa K, Shadduck R K, Waheed A, Hata J. Multipotent marrow stromal cell line is able to induce hematopoiesis in vivo. J Cell Physiol. 1992; 151:197-205.

Vachon P. Beaudry F, Marier J F, Ste-Marie L, Montgomery J. Cyclosporin A in blood and brain tissue following intracarotid injections in normal and stroke-induced rats. Brain Res. 2002; 943:1-8.

Woodbury, D., Schwarz, E. J., Prockop, D. J. and Black, I. B. 2000. Adult rat and human bone marrow stromal cells differentiate into neurons. J. Neurosci. Res. 61: 364-370.

Zhang K and Terrence J. Sejnowski. A universal scaling law between gray matter and white matter of cerebral cortex. PNAS, 2000, 10: 5621-5626.

Zhang R L, Zhang Z G, Zhang L, Chopp M. Proliferation and differentiation of progenitor cells in the cortex and the subventricular zone in the adult rat after focal cerebral ischemia. Neuroscience. 2001; 105(1):3341.

Zhao L R, Duan W M, Reyes M, Keene C D, Verfaillie C M, Low W C. Human bone marrow stem cells exhibit neural phenotypes and ameliorate neurological deficits after grafting into the ischemic brain of rats. Exp Neurol. 2002; 174:11-20.

What is claimed is:

1. A method for treating ischemic or hemorrhagic stroke, the method comprising:
   administering neuronal precursor cells to a patient suffering from ischemic or hemorrhagic stroke;
   wherein the neuronal precursor cells are obtained by transfecting marrow adherent stem cells with a vector comprising sequences encoding a Notch intracellular domain.

2. The method of claim 1, wherein the neuronal precursor cells are administered locally.

3. The method of claim 2, wherein the neuronal precursor cells are administered to the central nervous system.

4. The method of claim 1, wherein the neuronal precursor cells are administered intraparenchymally.

5. The method of claim 1, wherein the neuronal precursor cells comprise human neuronal precursor cells.

6. The method of claim 1, further comprising allowing the neuronal precursor cells to migrate from a site of administration to one or more other locations in the patient.

7. The method of claim 6, wherein another location in the patient comprises the site of ischemic or hemorrhagic stroke.

8. The method of claim 1, further comprising administering an immunosuppressive agent to the patient.

9. The method of claim 1, wherein the neuronal precursor cells are allogeneic with respect to the patient.

10. A method for treating ischemic or hemorrhagic stroke, the method comprising:
    administering marrow-adherent stem cell-derived neuronal cells to a patient suffering from ischemic or hemorrhagic stroke;
    wherein the marrow adherent stem cell-derived neuronal cells are obtained by:
    (a) transfecting marrow adherent stem cells with a vector comprising sequences encoding a Notch intracellular domain; and
    (b) further differentiating the cells of step (a) into post-mitotic neuronal cells by culture in the presence of one or more trophic factors.

11. The method of claim 10, wherein the marrow-adherent stem cell-derived neuronal cells are administered locally.

12. The method of claim 11, wherein the marrow-adherent stem cell-derived neuronal cells are administered to the central nervous system.

13. The method of claim 10, wherein the marrow-adherent stem cell-derived neuronal cells are administered intraparenchymally.

14. The method of claim 10, wherein the marrow-adherent stem cell-derived neuronal cells comprise human marrow-adherent stem cell-derived neuronal cells.

15. The method of claim 10, wherein the further differentiating comprises:
    culturing the cells of step (a) in alpha-MEM containing 10% fetal bovine serum (FBS), 5 uM forskolin (FSK), 10 ng/ml basic fibroblast growth factor (bFGF) and 10 ng/ml ciliary neurotrophic factor (CNTF).

16. The method of claim 10, further comprising administering an immunosuppressive agent to the patient.

17. The method of claim 10, wherein the marrow-adherent stem cell-derived neuronal cells are allogeneic with respect to the patient.

18. The method of claim 10, further comprising allowing the marrow-adherent stem cell-derived neuronal cells to migrate from a site of administration to one or more other locations in the patient.

19. The method of claim 18, wherein another location in the patient comprises the site of ischemic or hemorrhagic stroke.

* * * * *